(12) United States Patent
Andres Gil et al.

(10) Patent No.: US 12,338,243 B2
(45) Date of Patent: Jun. 24, 2025

(54) P2X7 MODULATORS

(71) Applicant: JANSSEN PHARMACEUTICA NV, Beerse (BE)

(72) Inventors: Jose Ignacio Andres Gil, Madrid (ES); Christa C. Chrovian, La Jolla, CA (US); Michael A. Letavic, San Diego, CA (US); Jason C. Rech, San Diego, CA (US); Dale A. Rudolph, San Diego, CA (US); Akinola Soyode-Johnson, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 137 days.

(21) Appl. No.: 17/650,155

(22) Filed: Feb. 7, 2022

(65) Prior Publication Data
US 2022/0235062 A1 Jul. 28, 2022

Related U.S. Application Data

(63) Continuation of application No. 15/541,040, filed as application No. PCT/US2015/046852 on Aug. 26, 2015, now abandoned.

(60) Provisional application No. 62/049,727, filed on Sep. 12, 2014.

(51) Int. Cl.

| | | |
|---|---|---|
| C07D 487/04 | (2006.01) |
| A61P 1/00 | (2006.01) |
| A61P 3/10 | (2006.01) |
| A61P 7/02 | (2006.01) |
| A61P 9/12 | (2006.01) |
| A61P 11/00 | (2006.01) |
| A61P 11/06 | (2006.01) |
| A61P 13/10 | (2006.01) |
| A61P 13/12 | (2006.01) |
| A61P 17/00 | (2006.01) |
| A61P 17/06 | (2006.01) |
| A61P 17/10 | (2006.01) |
| A61P 19/02 | (2006.01) |
| A61P 19/10 | (2006.01) |
| A61P 25/00 | (2006.01) |
| A61P 25/04 | (2006.01) |
| A61P 25/08 | (2006.01) |
| A61P 25/16 | (2006.01) |
| A61P 25/18 | (2006.01) |
| A61P 25/22 | (2006.01) |
| A61P 25/24 | (2006.01) |
| A61P 25/28 | (2006.01) |
| A61P 27/06 | (2006.01) |
| A61P 31/00 | (2006.01) |
| A61P 31/04 | (2006.01) |
| A61P 33/00 | (2006.01) |

(Continued)

(52) U.S. Cl.
CPC .............. *C07D 487/04* (2013.01); *A61P 1/00* (2018.01); *A61P 3/10* (2018.01); *A61P 7/02* (2018.01); *A61P 9/12* (2018.01); *A61P 11/00* (2018.01); *A61P 11/06* (2018.01); *A61P 13/10* (2018.01); *A61P 13/12* (2018.01); *A61P 17/00* (2018.01); *A61P 17/06* (2018.01); *A61P 17/10* (2018.01); *A61P 19/02* (2018.01); *A61P 19/10* (2018.01); *A61P 25/00* (2018.01); *A61P 25/04* (2018.01); *A61P 25/08* (2018.01); *A61P 25/16* (2018.01); *A61P 25/18* (2018.01); *A61P 25/22* (2018.01); *A61P 25/24* (2018.01); *A61P 25/28* (2018.01); *A61P 27/06* (2018.01); *A61P 31/00* (2018.01); *A61P 31/04* (2018.01); *A61P 33/00* (2018.01); *A61P 35/00* (2018.01); *A61P 37/08* (2018.01)

(58) Field of Classification Search
CPC ................................................... C07D 487/04
See application file for complete search history.

(56) References Cited

U.S. PATENT DOCUMENTS

| | | |
|---|---|---|
| 4,812,462 A | 3/1989 | Blankley et al. |
| 4,816,463 A | 3/1989 | Blankley et al. |
| 5,338,744 A | 8/1994 | Dudley et al. |

(Continued)

FOREIGN PATENT DOCUMENTS

| | | |
|---|---|---|
| CN | 101778850 | 7/2010 |
| JP | 2013-505220 | 2/2013 |

(Continued)

OTHER PUBLICATIONS

Liu et al. (Frontiers in Pharmacology, 2024, 4643-4656).*

(Continued)

*Primary Examiner* — Susanna Moore
(74) *Attorney, Agent, or Firm* — Wan Chieh Lee; Haug Partners LLP

(57) ABSTRACT

The present invention is directed to compounds of Formula (I), which includes enantiomer and diasteromers thereof:

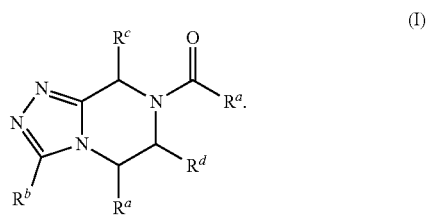

The invention also relates to pharmaceutical compositions comprising compounds of Formula (I). Methods of making and using the compounds of Formula (I) are also within the scope of the invention.

23 Claims, No Drawings

(51) Int. Cl.
*A61P 35/00* (2006.01)
*A61P 37/08* (2006.01)

(56) References Cited

U.S. PATENT DOCUMENTS

| | | | |
|---|---|---|---|
| 8,431,704 B2 | 4/2013 | Love et al. | |
| 8,871,760 B2 | 10/2014 | Brotherton-Pleiss et al. | |
| 8,933,236 B2 | 1/2015 | Chowdhury et al. | |
| 8,987,249 B2 | 3/2015 | Anderskewitz et al. | |
| 9,040,534 B2 | 5/2015 | Ameriks et al. | |
| 9,056,874 B2 | 6/2015 | Adams et al. | |
| 9,066,946 B2 | 6/2015 | Alcazar Vaca et al. | |
| 9,156,824 B2 | 10/2015 | Dally et al. | |
| 9,181,271 B2 | 11/2015 | Li et al. | |
| 9,233,974 B2 | 1/2016 | Link et al. | |
| 9,242,969 B2 | 1/2016 | Barsanti et al. | |
| 9,273,047 B2 | 3/2016 | Hunt et al. | |
| 9,290,476 B2 | 3/2016 | Leonard et al. | |
| 9,375,418 B2 | 6/2016 | Schmidt et al. | |
| 9,434,715 B2 | 9/2016 | Conza et al. | |
| 9,447,045 B2 | 9/2016 | Chen et al. | |
| 9,464,084 B2 | 10/2016 | Alcazar Vaca et al. | |
| 9,532,992 B2 | 1/2017 | Kuntz et al. | |
| 9,540,388 B2 | 1/2017 | Letavic et al. | |
| 9,561,228 B2 | 2/2017 | Haq et al. | |
| 9,617,272 B2 | 4/2017 | Kumar et al. | |
| 9,637,456 B2 | 5/2017 | Amans et al. | |
| 2005/0096345 A1 | 5/2005 | Thompson et al. | |
| 2006/0217448 A1 | 9/2006 | Kelly et al. | |
| 2006/0293337 A1 | 12/2006 | Evans et al. | |
| 2008/0275052 A1 | 11/2008 | Dhar et al. | |
| 2010/0144758 A1 | 6/2010 | Dillon et al. | |
| 2011/0252717 A1 | 10/2011 | Graf Fernandez | |
| 2011/0294790 A1 | 12/2011 | Mantegani et al. | |
| 2012/0157436 A1* | 6/2012 | Dean | A61P 25/14 514/249 |
| 2012/0190680 A1 | 7/2012 | Bakthavatchalam et al. | |
| 2013/0023530 A1* | 1/2013 | Hoveyda | A61P 25/24 514/249 |
| 2014/0213554 A1 | 7/2014 | Wu et al. | |
| 2014/0251902 A1 | 9/2014 | Solheim et al. | |
| 2014/0275015 A1 | 9/2014 | Alcazar Vaca et al. | |
| 2014/0275056 A1 | 9/2014 | Letavic et al. | |
| 2014/0275096 A1 | 9/2014 | Ameriks et al. | |
| 2014/0275120 A1 | 9/2014 | Alcazar Vaca et al. | |
| 2015/0029190 A1 | 1/2015 | Ishida et al. | |
| 2015/0290190 A1 | 10/2015 | Ameriks et al. | |
| 2015/0322062 A1 | 11/2015 | Alcazar Vaca et al. | |
| 2016/0016962 A1 | 1/2016 | Ameriks et al. | |
| 2016/0024082 A1 | 1/2016 | Alcazar Vaca et al. | |
| 2016/0039809 A1 | 2/2016 | Alcazar Vaca et al. | |
| 2016/0039836 A1 | 2/2016 | Letavic et al. | |
| 2016/0046596 A1 | 2/2016 | Banerjee et al. | |
| 2017/0081342 A1 | 3/2017 | Cheung et al. | |

FOREIGN PATENT DOCUMENTS

| | | |
|---|---|---|
| WO | 2004/014374 | 2/2004 |
| WO | 2006/023750 | 3/2006 |
| WO | 2006/080884 | 8/2006 |
| WO | 2006/110516 | 10/2006 |
| WO | 2009/002423 | 12/2008 |
| WO | 2009/023623 | 2/2009 |
| WO | 2010/125101 | 11/2010 |
| WO | 2010/125102 | 11/2010 |
| WO | 2011/103715 | 9/2011 |
| WO | 2011/121137 | 10/2011 |
| WO | 2012/040048 | 3/2012 |
| WO | 2014/097140 | 6/2014 |
| WO | 2014/152589 | 9/2014 |
| WO | 2014/152621 | 9/2014 |
| WO | 2014/154897 | 10/2014 |
| WO | 2016/029983 | 3/2016 |
| WO | 2016/039977 | 3/2016 |

OTHER PUBLICATIONS

2-Naphtalenecarboxamide,6-Methoxy-N-[2-(4-morpholinyl)-2-(2-thienyl) ethyl], Enamine Screening Library, Jan. 17, 2008, pp. 1-1, 940789-91-3.

2-Quinolinecarboxamide,N-[2-(5-methyl-2-furanyl)-2-(4-morpholinyl) ethyl], Ryan Scientific Screening Library, Jan. 25, 2008, pp. 1-1, 924250-65-7.

2-Quinolinecarboxamide,N-[2-(5-methyl-2-furanyl)-2-(4-morpholinyl) ethyl], Ambinter Stock Screening Collection, Feb. 13, 2008, pp. 1-1, 924250-65-7.

3-Quinolinecarboxamide,1,2-dihydro N-[2-(4-morpholinyl)-2-(2-thienyl) ethyl]-2-oxo, Ambinter Stock Screening Collection, Feb. 13, 2008, pp. 1-1, 927548-55-8.

3-Quinolinecarboxamide,2,6-dimethyl-N-[2-(1-Pyrrolidinyl)-2-(2thienyl)ethyl], Ambinter Stock Screening Collection, Feb. 13, 2008, pp. 1-1, 1015943-03-9.

3-Quinolinecarboxamide,6-chloro-2-methyl-N-[2-(4-morpholinyl)-2-(2-thienyl)ethyl], Ambinater Stock Screening Collection, Feb. 13, 2008, pp. 1-1, 940854-05-7.

3-Quinolinecarboxamide,7-Methoxy-2-methyl-N-[2-{4-morpholinyl}-2-(2-thienyl)ethyl], Ukrorgsynthesis Screening Collection, Mar. 6, 2007, pp. 1-1, 927559-99-7.

4-Quinolinecarboxamide,1,2-dihydro N-[2-(4-morpholinyl)-2-(2-thienyl) ethyl]-2-oxo, Ryan Scientific Screening Library, Jan. 25, 2008, pp. 1-1, 924223-35-8.

4-Quinolinecarboxamide,2-cycloprppyl-N-[2-(2-furanyl)-2-(1-pyrrolidinyl) ethyl], Ryan Scientific Screening Library, Jan. 25, 2008, pp. 1-1, 930656-70-5.

4-Quinolinecarboxamide,N-[2-(2--furanyl)-2-(1-Pyrrolidinyl) ethyl]-1,2-dihydro-2-oxo, Ryan Scientific Screening Library, Jan. 25, 2008, pp. 1-1, 924218-44-0.

4-Quinolinecarboxamide,N-[2-(2-furany)-2(1-Pyrrolidinyl)ethyl]-2(1-methylethyl, Aurora Screening Library, Sep. 6, 2007, pp. 1-1, 924386-46-9.

Arbeloa et al., "P2X7 receptor blockade prevents ATP excitotoxicity in neurons and reduces brain damage after ischemia", Neurobiology of Disease, vol. 45, Issue 3, Mar. 2012, pp. 954-961.

Arulkumaran et al., "A potential therapeutic role for P2X7 receptor (P2X7R) antagonists in the treatment of inflammatory diseases", Expert Opin Investig Drugs, Jul. 2011, vol. 20, Issue 7, pp. 897-915.

Avignone et al., "Status epilepticus induces a particular microglial activation state characterized by enhanced purinergic signaling", The Journal of Neuroscience, Sep. 10, 2008, vol. 28, Issue 37, pp. 9133-9144.

Bartlett et al., "The P2X7 Receptor Channel: Recent Developments and the Use of P2X7 Antagonists in Models of Disease", Pharmacological Reviews, Jul. 2014, vol. 66, pp. 638-675.

Basso et al., "Behavioral profile of P2X7 receptor knockout mice in animal models of depression and anxiety: Relevance for neuropsychiatric disorders", Behavioural Brain Research, Mar. 2009, vol. 198, Issue 1, pp. 83-90.

Bennet et al. (Editor), "Part XIV Oncology", Cecil Textbook of Medicine, 1996, vol. 1, 20th Edition, pp. 1004-1010.

Berge et al., "Pharmaceutical Salts", Journal of Pharmaceutical Sciences, 1997, vol. 66, Issue 1, pp. 1-19.

Berge et al., "Pharmaceutical Salts", Journal of Pharmaceutical Sciences, Jan. 1, 1977, vol. 66, No. 1, pp. 1-19—XP000562636.

Bertolini et al., "A New Rational Hypothesis for the Pharmacophore of the Active Metabolite of Leflunomide, a Potent Immunosuppressive Drug", J. Med. Chem., Jan. 1997, vol. 40, Issue 13, pp. 2011-2016.

Bourzac et al., "Glucose transporter 2 expression is down regulated following P2X7 activation in enterocytes", Journal of Cellular Physiology, 2013, vol. 228, pp. 120-129.

Bundgaard, "Bioreversible derivatives for various functional groups and chemical entities", Design of Prodrugs, 1985, pp. 1-3, Chapter 1.

Capuron et al., "Immune system to brain signaling: Neuropsychopharmacological implications", Pharmacology & Therapeutics, May 2011, vol. 130, Issue 2, pp. 226-238.

(56) References Cited

OTHER PUBLICATIONS

Chessell et al., "Disruption of the P2X7 purinoceptor gene abolishes chronic inflammatory and neuropathic pain", Pain, Apr. 2005, vol. 114, Issue 3, pp. 386-396.
Chu et al., "Inhibition of P2X7 receptor ameliorates transient global cerebral ischemia/reperfusion injury via modulating inflammatory responses in the rat hippocampus", Journal of Neuroinflammation, 2012, vol. 9, Issue 69, pp. 1-10.
Delarasse et al., "The Purinergic Receptor P2X7 Triggers α-Secretase-dependent Processing of the Amyloid Precursor Protein", The Journal of Biological Chemistry, Jan. 2011, vol. 286, Issue 4, pp. 2596-2606.
Hudson, "Methodological implications of simultaneous solid-phase peptide synthesis. 1. Comparison of different coupling procedures", J. Org. Chem., 1988, vol. 53, pp. 617-624.
Dermer, "Another Anniversary for the War on Cancer", Bio/Technology, Mar. 1994, vol. 12, pp. 320.
Donnelly-Roberts et al., "[3H]A-804598 ([3H]2-cyano-1-[(1S)-1-phenylethyl]-3-quinolin-5-ylguanidine) is a novel, potent, and selective antagonist radioligand for P2X7 receptors", Neuropharmacology, 2009, pp. 223-229.
Duan et al., "P2X7 Receptors: Properties and Relevance to CNS Function", GLIA, 2006, vol. 54, pp. 738-746.
Dyatkin et al., "Determination of the absolute configuration of a key tricyclic component of a novel vasopressin receptor antagonist by use of vibrational circular dichroism", Chirality, 2002, vol. 14, pp. 215-219.
Engel et al., "Seizure suppression and neuroprotection by targeting the purinergic P2X7 receptor during status epilepticus in mice", The FASEB Journal, 2012, vol. 26, pp. 1616-1628.
Ferrari et al., "The P2X7 Receptor: A Key Player in IL-1 Processing and Release", Journal of Immunology, 2006, vol. 176, pp. 3877-3883.
Fleisher et al., "Improved oral drug delivery: solubility limitations overcome by the use of prodrugs", Advanced Drug Delivery Reviews, 1996, vol. 19, Issue 2, pp. 115-130.
Freshney et al., "Culture of animal cells: a manual of basic technique", 1983, Chapter 1, pp. 1-6.
Friedle et al., "Recent Patents on Novel P2X7 Receptor Antagonists and their Potential for Reducing Central Nervous System Inflammation", Recent Patents on CNS Drug Discovery (Discontinued), 2010, vol. 5, No. 1, pp. 35-45.
Furlan-Freguia et al., "P2X7 receptor signaling contributes to tissue factor-dependent thrombosis in mice", Journal of Clinical Investigation, 2011, vol. 121, Issue 7, pp. 2932-2944.
Glenn D. Considine, Van Nostrand's Encyclopedia of Chemistry, Encyclopedia of Chemistry, 2005, Chapter 5, pp. 261.
Golub et al., "Molecular Classification of Cancer: Class Discovery and Class Prediction by Gene Expression Monitoring", Science, 1999, vol. 286, pp. 531-537.
Grygorowicz et al., "Temporal expression of P2X7 purinergic receptor during the course of experimental autoimmune encephalomyelitis", Neurochemistry International, 2010, vol. 57, Issue 7, pp. 823-829.
Guile et al., "Antagonists of the P2X7 Receptor. From Lead Identification to Drug Development", Journal of Medicinal Chemistry, 2009, vol. 52, Issue 10, pp. 3123-3141.
Gunosewoyo et al., "P2X purinergic receptor ligands: recently patented compounds", Expert Opinion on Therapeutic Patents, 2010, vol. 20, Issue 5, pp. 625-646.
Hackam et al., "Translation of Research Evidence From Animals to Humans", JAMA, 2006, vol. 296, pp. 1727-1732.
Hans Bundgaard, Design of Products, Design of Products, 1985, 1-3, 1.
Diaz-Hernandez et al., "In vivo P2X7 inhibition reduces amyloid plaques in Alzheimer's disease through GSK3β and secretases", Neurobiology of Aging, 2012, vol. 33, Issue 8, pp. 1816-1828.
Díaz-Hernández et al., "Altered P2X7-receptor level and function in mouse models of Huntington's disease and therapeutic efficacy of antagonist administration", The FASEB Journal, 2009, vol. 23, pp. 1893-1906.
Ji et al., "P2X7 deficiency attenuates hypertension and renal injury in deoxycorticosterone acetate-salt hypertension", American Journal of Physiology—Renal Physiology, 2012, vol. 303, No. 8, pp. F1207-F1215.
Jordan, "Tamoxifen: a most unlikely pioneering medicine", Nature Reviews, 2003, vol. 2, pp. 205-213.
Keating et al., "P2X7 Receptor-Dependent Intestinal Afferent Hypersensitivity in a Mouse Model of Postinfectious Irritable Bowel Syndrome", Journal of Immunology, 2011, vol. 187, pp. 1467-1474.
Bagshawe, "Antibody-Directed enzyme prodrug therapy: A review", Drug Development Research, 1995, vol. 34, pp. 220-230.
Killeen et al., "Signaling through Purinergic Receptors for ATP Induces Human Cutaneous Innate and Adaptive Th17 Responses: Implications in the Pathogenesis of Psoriasis", Journal of Immunology, 2013, vol. 190, pp. 4324-4336.
Kim et al., "Blockade of P2X receptor prevents astroglial death in the dentate gyrus following pilocarpine-induced status epilepticus", Neurological Research, 2009, vol. 31, pp. 982-988.
Krogsgaard-Larsen et al., A textbook of drug design and development, Harwood Academic Publishers, 1991, pp. 1-18.
Marcellino et al., "On the role of P2X7 receptors in dopamine nerve cell degeneration in a rat model of Parkinson's disease: studies with the P2X7 receptor antagonist A-438079", Journal of Neural Transmission, 2010, vol. 117, pp. 681-687.
Martins et al., "The role of P2X7 purinergic receptors in inflammatory and nociceptive changes accompanying cyclophosphamide-induced haemorrhagic cystitis in mice", British Journal of Pharmacology, 2012, vol. 165, pp. 183-196.
Müller et al., "A Potential Role for P2X7R in Allergic Airway Inflammation in Mice and Humans", American Journal of Respiratory Cell and Molecular Biology, 2011, vol. 44, Issue 4, pp. 456-464.
Bodor, "Novel approaches to the design of safer drugs: soft drugs and site-specific chemical delivery systems", Advances in Drug Research, 1984, vol. 13, pp. 256-331.
Oyanguren-Desez et al., "Gain-of-function of P2X7 receptor gene variants in multiple sclerosis", Cell Calcium, 2011, vol. 50, pp. 468-472.
Parvathenani et al., "P2X7 Mediates Superoxide Production in Primary Microglia and Is Up-regulated in a Transgenic Mouse Model of Alzheimer's Disease", The Journal of Biological Chemistry, 2003, vol. 278, Issue 15, pp. 13309-13317.
Paulekuhn et al., "Trends in Active Pharmaceutical Ingredient Salt Selection based on Analysis of the Orange Book Database", Journal of Medicinal Chemistry, 2007, vol. 50 Issue 26, pp. 6665-6672.
Dantzer, "Cytokine, Sickness Behavior, and Depression", Immunology and Allergy Clinics of North America, 2009, vol. 29, Issue 2, pp. 247-264.
Robinson et al., "Discovery of the Hemifumarate and (r-L-Alanyloxy)methyl Ether as Prodrugs of an Antirheumatic Oxindole: Prodrugs for the Enolic OH Group", Journal of Medicinal Chemistry, 1996, vol. 39, Issue 1, pp. 10-18.
Romagnoli et al., "The P2X 7 receptor as a therapeutic target", Expert Opin. Ther., 2008, vol. 15, Issue 5, pp. 647-661.
Rudolph et al., "Novel methyl substituted 1-(5,6-dihydro-[1,2,4]triazolo [4,3-a]pyrazin-7(8H)-yl)methanones are P2X7 antagonists", Bioorganic & Medicinal Chemistry Letters, 2015, vol. 25, pp. 3157-3163.
Sanz et al., "Activation of Microglia by Amyloid β Requires P2X7 Receptor Expression", The Journal of Immunology, 2009, vol. 182, pp. 4378-4385.
Shan et al., "Prodrug Strategies Based on Intramolecular Cyclization Reactions", Journal of Pharmaceutical Sciences, 1977, vol. 86, Issue 7, pp. 765-767.
Sharp et al., "P2X7 deficiency suppresses development of experimental autoimmune encephalomyelitis", Journal of Neuroinflammation, 2008, vol. 5, pp. 1-13.
Simone, Part XIV—Oncology, Textbook of Medicine, 1996, $20^{th}$ edition, vol. 1, pp. 1004-1010.

(56) References Cited

OTHER PUBLICATIONS

Skaper et al., "The P2X7 purinergic receptor: from physiology to neurological disorders", The FASEB Journal, 2010, vol. 24, pp. 337-345.
Solini et al., "Enhanced P2X7 Activity in Human Fibroblasts From Diabetic Patients. A Possible Pathogenetic Mechanism for Vascular Damage in Diabetes", Arteriosclerosis, Thrombosis, and Vascular Biology, 2004, vol. 24, pp. 1240-1245.
Stahl et al., "Handbook of Pharmaceutical Salts", International Union of pure and Applied Chemistry, 2002, pp. 1-3.
Surprenant et al., "Signaling at Purinergic P2X Receptors", Annual Review of Physiology, 2008, vol. 71, pp. 333-359.
Thiboutot et al., "Inflammasome Activation by *Propionibacterium acnes*: The Story of IL-1 in Acne Continues to Unfold," Journal of Investigative Dermatology, 2014, vol. 134, Issue 3, pp. 595-597.
V. Craig Jordan, "Tamoxifen: A Most Unlikely Pioneering Medicine", Nature Reviews Drug Discovery, 2003, vol. 2, pp. 205-213.
Vergani et al., "Effects of the purinergic Inhibitor Oxidized ATP in a model of Islet Allograft rejection", Diabetes, 2013, vol. 62, pp. 1665-1675.
Vergani et al., "Long term Heart Transplant Survival by targeting the Ionotropic Purinergic receptor P2X7", Circulation, 2013, vol. 127, pp. 463-475.
Schönherr et al., "Profound Methyl Effects in Drug Discovery and a Call for New C—H Methylation Reactions", Angewandte Chem. International Edition, 2013, vol. 52, pp. 12256-12267.

\* cited by examiner

P2X7 MODULATORS

CROSS REFERENCE TO RELATED APPLICATIONS

This application is a continuation of U.S. patent application Ser. No. 15/541,040 filed on Jun. 30, 2017, which is the national stage of PCT Application No. PCT/US2015/046852 filed on Aug. 26, 2015, which claims priority to U.S. Provisional Patent Application Ser. No. 62/049,727 filed on Sep. 12, 2014, all of the applications identified above are incorporated herein by reference in their entirety.

FIELD OF THE INVENTION

The present invention is related to compounds having P2X7 modulating properties, pharmaceutical compositions comprising these compounds, chemical processes for preparing these compounds and their use in the treatment of diseases associated with P2X7 receptor activity in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. Al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, Annu. Rev. Physiol. 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knockout mice. These mice demonstrate the role of P2X7 in the development and maintenance of pain, as these mice are protected from the development of both adjuvant-induced inflammatory pain and partial nerve ligation-induced neuropathic pain (Chessell et al., *Pain* 2005, 114, 386-396). In addition, P2X7 knockout mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the proinflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques indicating a role of this target in such pathology as well (Parvathenani et al., *J. Biol. Chem.* 2003, 278, 13309-13317).

Several reviews on small molecule inhibitors of P2X7 which have been published are: Guile, S. D., et al., J. Med. Chem, 2009, 52, 3123-3141; Gunosewoyo, H. and Kassiou, M., Exp Opin, 2010, 20, 625-646.

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

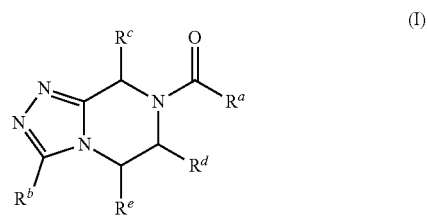

(I)

and enantiomers or diastereomers thereof;
and pharmaceutically acceptable salts thereof;
wherein:
$R^a$ is

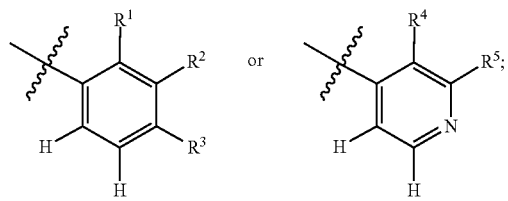

$R^1$ is halo or $C_1$-$C_3$alkyl;
$R^2$ is independently selected from the group consisting of: H, halo, and $C_1$-$C_3$perhaloalkyl;
$R^3$ is H or halo;
$R^4$ is halo,
$R^5$ is halo or $C_1$-$C_3$perhaloalkyl;
$R^b$ is independently selected from the group consisting of:

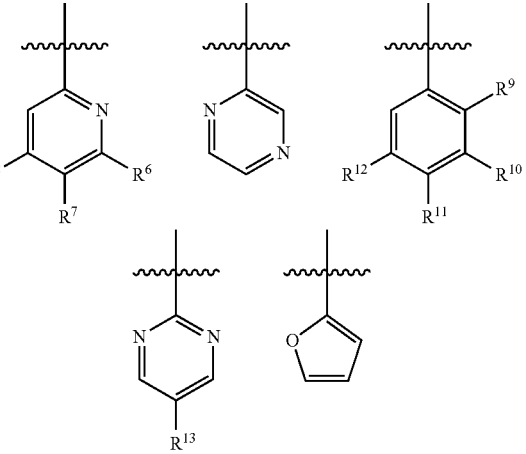

$C_3$-$C_6$ cycloalkyl $C_1$-$C_3$ perhaloalkyl $C_1$-$C_4$ alkyl and

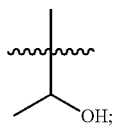

Wherein:
$R^6$, $R^9$, $R^{10}$, $R^{12}$, $R^{14}$ are independently H or halo;
$R^7$, $R^8$, $R^{13}$ is independently selected from the group consisting of: H, halo and $OC_1$-$C_3$alkyl;
$R^{11}$ is independently selected from the group consisting of: H, halo and $C_1$-$C_3$perhaloalkyl;
$R^c$ is selected from the group consisting of:

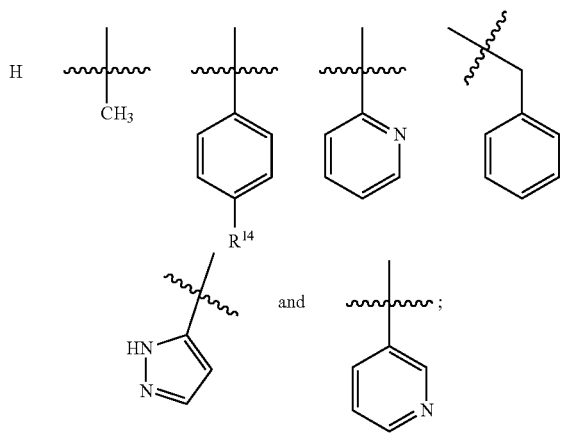

$R^d$ and $R^e$ are independently H or $C_1$-$C_3$alkyl; and
provided that at least one of $R^c$, $R^d$ and $R^e$ are not H.

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula I, as well as the pharmaceutically acceptable salts.

In a further aspect, the invention relates to pharmaceutical compositions for treating a disease, disorder, or medical condition mediated by P2X7 receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing P2X7 receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by P2X7 receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

DETAILED DESCRIPTION OF THE INVENTION

A compound of Formula (I):

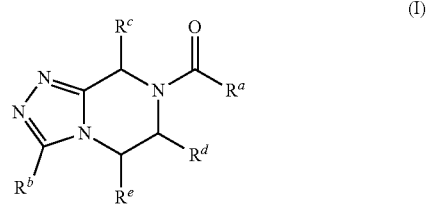

(I)

and enantiomers or diastereomers thereof;
and pharmaceutically acceptable salts thereof;
wherein:
$R^a$ is

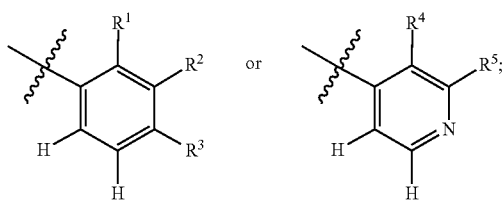

$R^1$ is halo or $C_1$-$C_3$alkyl;
$R^2$ is independently selected from the group consisting of: H, halo, and $C_1$-$C_3$perhaloalkyl;
$R^3$ is H or halo;
$R^4$ is halo,
$R^5$ is halo or $C_1$-$C_3$perhaloalkyl;
$R^b$ is independently selected from the group consisting of:

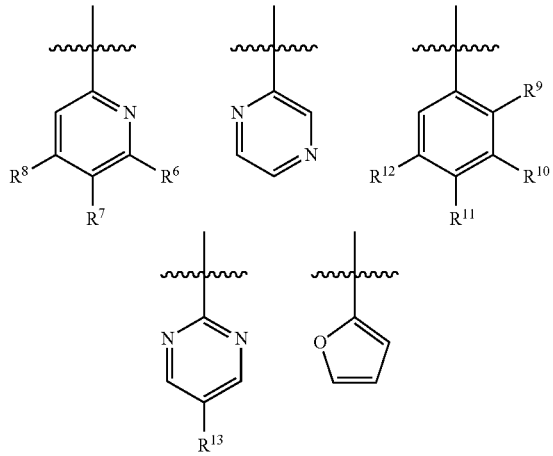

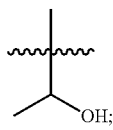

$C_3$-$C_6$ cycloalkyl $C_1$-$C_3$ perhaloalkyl $C_1$-$C_4$ alkyl and

Wherein:
$R^6$, $R^9$, $R^{10}$, $R^{12}$, $R^{14}$ are independently H or halo;
$R^7$, $R^8$, $R^{13}$ is independently selected from the group consisting of: H, halo and $OC_1$-$C_3$alkyl;
$R^{11}$ is independently selected from the group consisting of: H, halo and $C_1$-$C_3$perhaloalkyl;
$R^c$ is selected from the group consisting of:

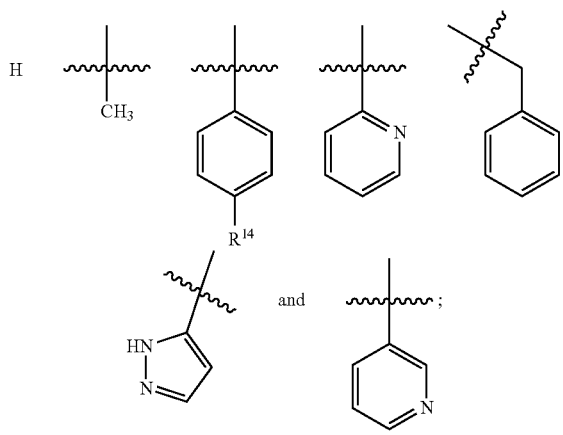

$R^d$ and $R^e$ are independently H or $C_1$-$C_3$alkyl; and provided that at least one of $R^c$, $R^d$ and $R^e$ are not H.

A further embodiment of the current invention is a compound of Formula (I) wherein $R^a$ is

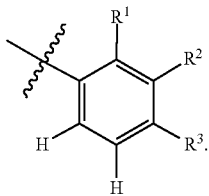

A further embodiment of the current invention is a compound of Formula (I) wherein $R^a$ is

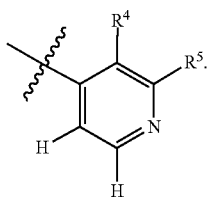

A further embodiment of the current invention is a compound of Formula (I) wherein $R^a$ is

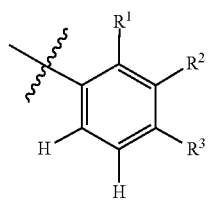

and $R^1$ is halo.

A further embodiment of the current invention is a compound of Formula (I) wherein $R^a$ is

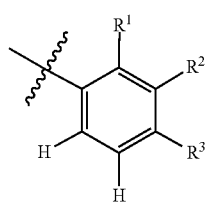

and $R^1$ is $C_1$-$C_3$alkyl.

A further embodiment of the current invention is a compound of Formula (I) wherein $R^a$ is

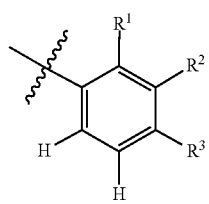

and $R^2$ is $C_1$-$C_3$perhaloalkyl.

A further embodiment of the current invention is a compound of Formula (I) wherein $R^a$ is

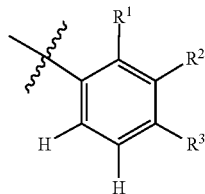

and $R^2$ is halo.

A further embodiment of the current invention is a compound of Formula (I) wherein $R^a$ is

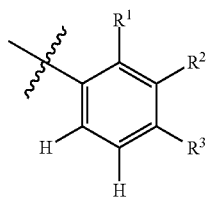

and $R^3$ is H.

A further embodiment of the current invention is a compound of Formula (I) wherein $R^a$ is

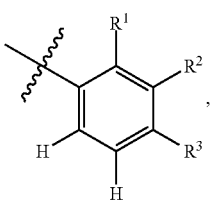

$R^1$ is halo, $R^2$ is $C_1$-$C_3$perhaloalkyl, and $R^3$ is H.

A further embodiment of the current invention is a compound of Formula (I) wherein $R^a$ is

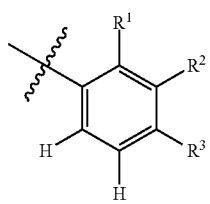

and $R^1$, $R^2$, and $R^3$ are halo.

A further embodiment of the current invention is a compound of Formula (I) wherein $R^a$ is

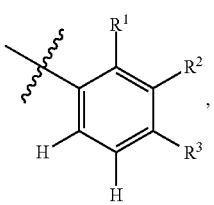

$R^1$ and $R^3$ are halo and $R^2$ is H.

A further embodiment of the current invention is a compound of Formula (I) wherein $R^a$ is

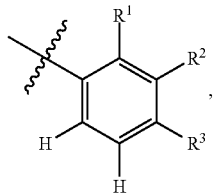

$R^1$ and $R^2$ are halo and $R^3$ is H.

A further embodiment of the current invention is a compound of Formula (I) wherein $R^a$ is

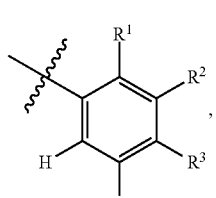

$R^4$ is halo and $R^5$ is $C_1$-$C_3$perhaloalkyl.

A further embodiment of the current invention is a compound of Formula (I) wherein $R^b$ is independently selected from the group consisting of:

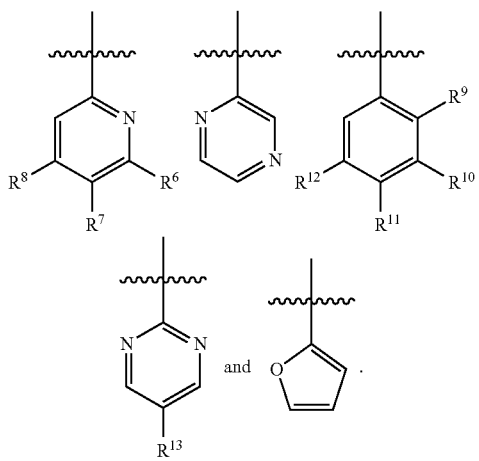

A further embodiment of the current invention is a compound of Formula (I) wherein $R^b$ is independently selected from the group consisting of:

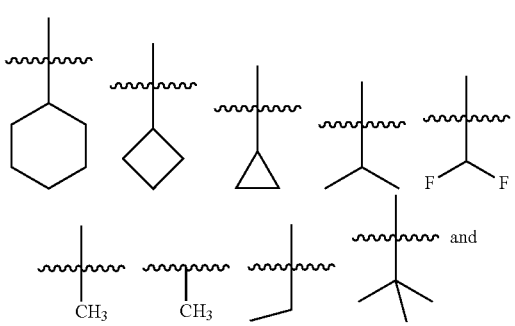

-continued

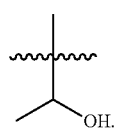

A further embodiment of the current invention is a compound of Formula (I) wherein $R^b$ is independently selected from the group consisting of:

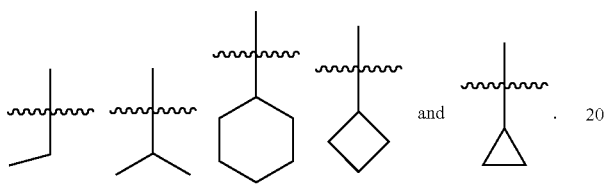 and

A further embodiment of the current invention is a compound of Formula (I) wherein $R^b$ is

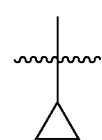

A further embodiment of the current invention is a compound of Formula (I) wherein $R^b$ is

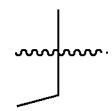

A further embodiment of the current invention is a compound of Formula (I) wherein $R^b$ is

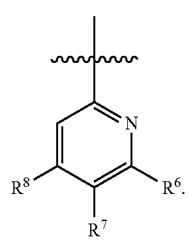

A further embodiment of the current invention is a compound of Formula (I) wherein $R^b$ is

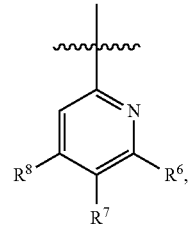

$R^6$ and $R^7$ are H and $R^8$ is $OCH_3$.

A further embodiment of the current invention is a compound of Formula (I) wherein $R^b$ is

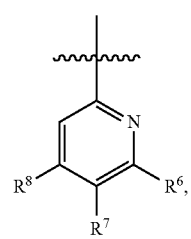

and $R^6$, $R^7$ and $R^8$ are H.

A further embodiment of the current invention is a compound of Formula (I) wherein $R^b$ is

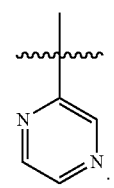 [SMILES: *c1cnccn1]

A further embodiment of the current invention is a compound of Formula (I) wherein $R^b$ is

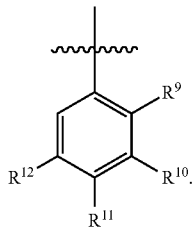

A further embodiment of the current invention is a compound of Formula (I) wherein $R^b$ is

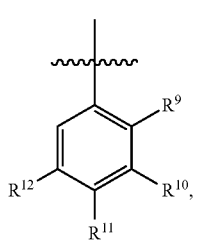

$R^9$, $R^{10}$ and $R^{12}$ are H and $R^{11}$ is F.

A further embodiment of the current invention is a compound of Formula (I) wherein $R^b$ is

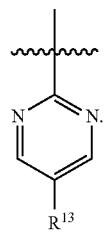

A further embodiment of the current invention is a compound of Formula (I) wherein $R^b$ is

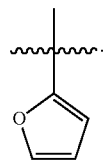

A further embodiment of the current invention is a compound of Formula (I) wherein $R^c$ is H or $CH_3$.

A further embodiment of the current invention is a compound of Formula (I) wherein $R^c$ is selected from the group consisting of:

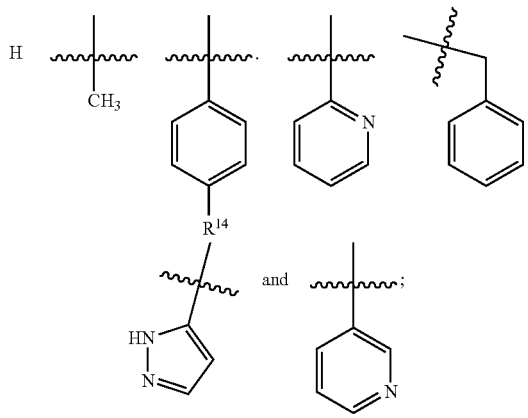

A further embodiment of the current invention is a compound of Formula (I) wherein $R^c$ is:

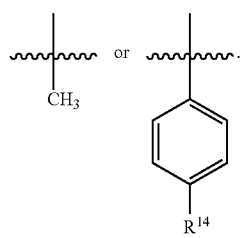

A further embodiment of the current invention is a compound of Formula (I) wherein $R^c$ is:

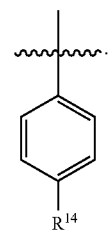

A further embodiment of the current invention is a compound of Formula (I) wherein $R^d$ is $CH_3$.

A further embodiment of the current invention is a compound of Formula (I) wherein $R^e$ is $CH_3$.

A further embodiment of the current invention is a compound of Formula (I) wherein $R^c$ is $CH_3$ and $R^d$ and $R^e$ are H.

A further embodiment of the current invention is a compound of Formula (I) wherein $R^d$ is $CH_3$ and $R^c$ and $R^e$ are H.

A further embodiment of the current invention is a compound of Formula (I) wherein $R^e$ is $CH_3$ and $R^c$ and $R^d$ are H.

A further embodiment of the current invention is a compound of Formula (I) wherein $R^a$ is

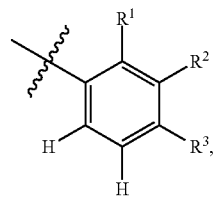

$R^1$ and $R^2$ are Cl, $R^c$ is $CH_3$, $R^b$ is

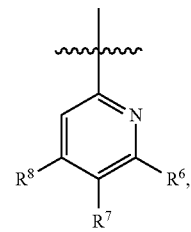

and $R^d$, $R^e$, $R^3$, $R^6$, $R^7$ and $R^8$ are H.

A further embodiment of the current invention is a compound of Formula (I) wherein $R^a$ is

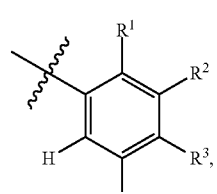

$R^1$ and $R^2$ are Cl, $R^d$ is $CH_3$, $R^b$ is

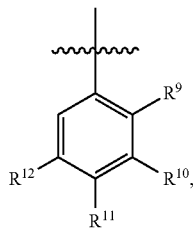

and $R^c$, $R^e$, $R^3$, $R^9$, $R^{10}$ and $R^{12}$ are H and $R^{11}$ is F.

A further embodiment of the current invention is a compound of Formula (I) wherein $R^a$ is

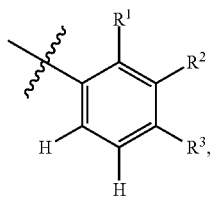

$R^1$ is Cl, and $R^2$ is $CF_3$, $R^d$ is $CH_3$, $R^b$ is

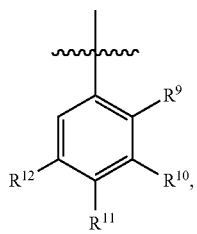

and $R^c$, $R^e$, $R^3$, $R^9$, $R^{19}$ and $R^{12}$ are H and $R^{11}$ is F.

A further embodiment of the current invention is a compound of Formula (I) wherein $R^a$ is

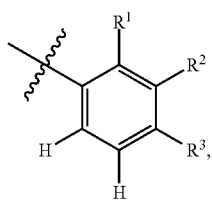

$R^1$ and $R^2$ are Cl, $R^d$ is $CH_3$, $R^b$ is

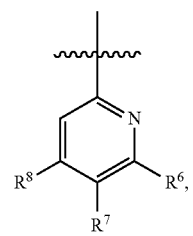

and $R^8$ is $OCH_3$, $R^c$, $R^e$, $R^3$, $R^6$, and $R^7$ are H.

A further embodiment of the current invention is a compound of Formula (I) wherein $R^a$ is

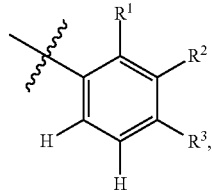

$R^1$ is Cl, and $R^2$ is $CF_3$, $R^d$ is $CH_3$, $R^c$ is

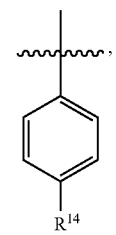

$R^b$ is

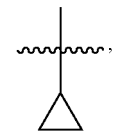

and $R^d$, $R^e$, and $R^3$, are H.

A further embodiment of the current invention is a compound of Formula (I) wherein $R^a$ is

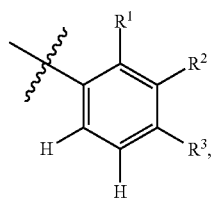

$R^1$ is Cl, and $R^2$ is $CF_3$, $R^d$ is $CH_3$, $R^c$ is

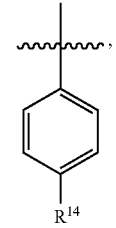

$R^b$ is

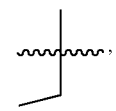

and $R^d$, $R^e$, and $R^3$, are H.

A further embodiment of the current invention is a compound of Formula (I) wherein $R^a$ is

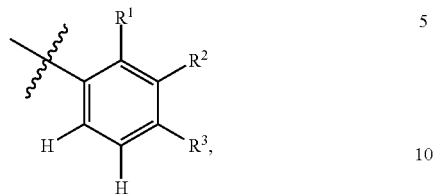

$R^1$ is Cl, and $R^2$ is $CF_3$, $R^d$ is $CH_3$, $R^c$ is

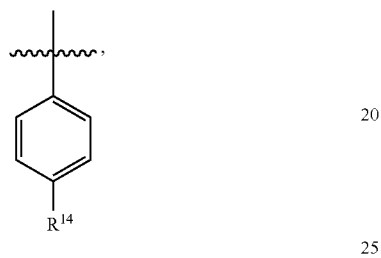

$R^b$ is

and $R^d$, $R^e$, and $R^3$, are H.

A further embodiment of the current invention is a compound as shown below in Table 1.

TABLE 1

(2,3-dichlorophenyl)(8-methyl-3-(pyridin-2-yl)-5,6-dihydro-[1,2,4]triazolo[4,3-a]pyrazin-7(8H)-yl)methanone
(R)-(2,3-dichlorophenyl)(8-methyl-3-(pyridin-2-yl)-5,6-dihydro-[1,2,4]triazolo[4,3-a]pyrazin-7(8H)-yl)methanone
(S)-(2,3-dichlorophenyl)(8-methyl-3-(pyridin-2-yl)-5,6-dihydro-[1,2,4]triazolo[4,3-a]pyrazin-7(8H)-yl)methanone
2-chloro-3-(trifluoromethyl)phenyl)(5-methyl-3-phenyl-5,6-dihydro-[1,2,4]triazolo[4,3-a]pyrazin-7(8H)-yl)methanone
(2,3-dichlorophenyl)(5-methyl-3-phenyl-5,6-dihydro-[1,2,4]triazolo[4,3-a]pyrazin-7(8H)-yl)methanone
(2-chloro-3-(trifluoromethyl)phenyl)(3-(4-fluorophenyl)-5-methyl-5,6-dihydro-[1,2,4]triazolo[4,3-a]pyrazin-7(8H)-yl)methanone
:(2,3-dichlorophenyl)(3-(4-fluorophenyl)-5-methyl-5,6-dihydro-[1,2,4]triazolo[4,3-a]pyrazin-7(8H)-yl)methanone
(2-chloro-3-(trifluoromethyl)phenyl)(3-(4-fluorophenyl)-6-methyl-5,6-dihydro-[1,2,4]triazolo[4,3-a]pyrazin-7(8H)-yl)methanone
(2,3-dichlorophenyl)(3-(4-fluorophenyl)-6-methyl-5,6-dihydro-[1,2,4]triazolo[4,3-a]pyrazin-7(8H)-yl)methanone
(2-chloro-3-(trifluoromethyl)phenyl)(6-methyl-3-phenyl-5,6-dihydro-[1,2,4]triazolo[4,3-a]pyrazin-7(8H)-yl)methanone
(2,3-dichlorophenyl)(6-methyl-3-phenyl-5,6-dihydro-[1,2,4]triazolo[4,3-a]pyrazin-7(8H)-yl)methanone
(R)-(2,3-dichlorophenyl)(6-methyl-3-phenyl-5,6-dihydro-[1,2,4]triazolo[4,3-a]pyrazin-7(8H)-yl)methanone
(S)-(2,3-dichlorophenyl)(6-methyl-3-phenyl-5,6-dihydro-[1,2,4]triazolo[4,3-a]pyrazin-7(8H)-yl)methanone
(R)-(2-chloro-3-(trifluoromethyl)phenyl)(6-methyl-3-phenyl-5,6-dihydro-[1,2,4]triazolo[4,3-a]pyrazin-7(8H)-yl)methanone
(S)-(2-chloro-3-(trifluoromethyl)phenyl)(6-methyl-3-phenyl-5,6-dihydro-[1,2,4]triazolo[4,3-a]pyrazin-7(8H)-yl)methanone
(3-chloro-2-(trifluoromethyl)pyridin-4-yl)(8-methyl-3-(pyridin-2-yl)-5,6-dihydro-[1,2,4]triazolo[4,3-a]pyrazin-7(8H)-yl)methanone
(2-chloro-3-(trifluoromethyl)phenyl)(8-methyl-3-(pyridin-2-yl)-5,6-dihydro-[1,2,4]triazolo[4,3-a]pyrazin-7(8H)-yl)methanone TABLE 1-continued (R)-(2,3-dichlorophenyl)(3-(4-fluorophenyl)-6-methyl-5,6-dihydro-[1,2,4]triazolo[4,3-a]pyrazin-7(8H)-yl)methanone
(S)-(2,3-dichlorophenyl)(3-(4-fluorophenyl)-6-methyl-5,6-dihydro-[1,2,4]triazolo[4,3-a]pyrazin-7(8H)-yl)methanone
(2-fluoro-3-(trifluoromethyl)phenyl)(8-methyl-3-(pyridin-2-yl)-5,6-dihydro-[1,2,4]triazolo[4,3-a]pyrazin-7(8H)-yl)methanone
(S)-(2-chloro-3-(trifluoromethyl)phenyl)(3-(4-fluorophenyl)-6-methyl-5,6-dihydro-[1,2,4]triazolo[4,3-a]pyrazin-7(8H)-yl)methanone
(S)-(2,3-dichlorophenyl)(6-methyl-3-(pyrazin-2-yl)-5,6-dihydro-[1,2,4]triazolo[4,3-a]pyrazin-7(8H)-yl)methanone
(S)-(2-chloro-3-(trifluoromethyl)phenyl)(6-methyl-3-(pyrazin-2-yl)-5,6-dihydro-[1,2,4]triazolo[4,3-a]pyrazin-7(8H)-yl)methanone
(S)-(2-chloro-3-(trifluoromethyl)phenyl)(3-(furan-2-yl)-6-methyl-5,6-dihydro-[1,2,4]triazolo[4,3-a]pyrazin-7(8H)-yl)methanone
(2-chloro-3-(trifluoromethyl)phenyl)(3-(4-fluorophenyl)-8-methyl-5,6-dihydro-[1,2,4]triazolo[4,3-a]pyrazin-7(8H)-yl)methanone
(S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone
(S)-(2-chloro-3-(trifluoromethyl)phenyl)(6-methyl-3-(4-(trifluoromethyl)phenyl)-5,6-dihydro-[1,2,4]triazolo[4,3-a]pyrazin-7(8H)-yl)methanone
(S)-(2,3-dichlorophenyl)(3-(3-fluoro-4-(trifluoromethyl)phenyl)-6-methyl-5,6-dihydro-[1,2,4]triazolo[4,3-a]pyrazin-7(8H)-yl)methanone
(S)-(2-chloro-3-(trifluoromethyl)phenyl)(3-(3-fluoro-4-(trifluoromethyl)phenyl)-6-methyl-5,6-dihydro-[1,2,4]triazolo[4,3-a]pyrazin-7(8H)-yl)methanone
(S)-(2-chloro-3-(trifluoromethyl)phenyl)(6-methyl-3-(3,4,5-trifluorophenyl)-5,6-dihydro-[1,2,4]triazolo[4,3-a]pyrazin-7(8H)-yl)methanone
(S)-(2,3-dichlorophenyl)(6-methyl-3-(pyridin-2-yl)-5,6-dihydro-[1,2,4]triazolo[4,3-a]pyrazin-7(8H)-yl)methanone
(R)-(2,3-dichlorophenyl)(3-(4-fluorophenyl)-6-methyl-5,6-dihydro-[1,2,4]triazolo[4,3-a]pyrazin-7(8H)-yl)methanone
(S)-(2,3-dichlorophenyl)(3-(4-fluorophenyl)-6-methyl-5,6-dihydro-[1,2,4]triazolo[4,3-a]pyrazin-7(8H)-yl)methanone
(2,3-dichlorophenyl)(5-methyl-3-(pyridin-2-yl)-5,6-dihydro-[1,2,4]triazolo[4,3-a]pyrazin-7(8H)-yl)methanone
(2-chloro-3-(trifluoromethyl)phenyl)(8-methyl-3-(4-(trifluoromethyl)phenyl)-5,6-dihydro-[1,2,4]triazolo[4,3-a]pyrazin-7(8H)-yl)methanone
(2-chloro-3-(trifluoromethyl)phenyl)(8-methyl-3-(pyrazin-2-yl)-5,6-dihydro-[1,2,4]triazolo[4,3-a]pyrazin-7(8H)-yl)methanone
(2-chloro-3-(trifluoromethyl)phenyl)(3-(4-chlorophenyl)-8-methyl-5,6-dihydro-[1,2,4]triazolo[4,3-a]pyrazin-7(8H)-yl)methanone
(S)-(2,3-dichlorophenyl)(3-(2-fluorophenyl)-6-methyl-5,6-dihydro-[1,2,4]triazolo[4,3-a]pyrazin-7(8H)-yl)methanone
(S)-(2-chloro-3-(trifluoromethyl)phenyl)(3-(2-fluorophenyl)-6-methyl-5,6-dihydro-[1,2,4]triazolo[4,3-a]pyrazin-7(8H)-yl)methanone
(S)-(2,3-dichloro-4-fluorophenyl)(3-(2-fluorophenyl)-6-methyl-5,6-dihydro-[1,2,4]triazolo[4,3-a]pyrazin-7(8H)-yl)methanone
(S)-(2,3-dichlorophenyl)(3-(3-fluorophenyl)-6-methyl-5,6-dihydro-[1,2,4]triazolo[4,3-a]pyrazin-7(8H)-yl)methanone
(S)-(2-chloro-3-(trifluoromethyl)phenyl)(3-(3-fluorophenyl)-6-methyl-5,6-dihydro-[1,2,4]triazolo[4,3-a]pyrazin-7(8H)-yl)methanone
(S)-(2,3-dichloro-4-fluorophenyl)(3-(3-fluorophenyl)-6-methyl-5,6-dihydro-[1,2,4]triazolo[4,3-a]pyrazin-7(8H)-yl)methanone
(S)-(2,3-dichlorophenyl)(3-(2,3-difluorophenyl)-6-methyl-5,6-dihydro-[1,2,4]triazolo[4,3-a]pyrazin-7(8H)-yl)methanone
(S)-(2-chloro-3-(trifluoromethyl)phenyl)(3-(2,3-difluorophenyl)-6-methyl-5,6-dihydro-[1,2,4]triazolo[4,3-a]pyrazin-7(8H)-yl)methanone
(S)-(2,3-dichloro-4-fluorophenyl)(3-(2,3-difluorophenyl)-6-methyl-5,6-dihydro-[1,2,4]triazolo[4,3-a]pyrazin-7(8H)-yl)methanone
(S)-(2,3-dichlorophenyl)(3-(3,4-difluorophenyl)-6-methyl-5,6-dihydro-[1,2,4]triazolo[4,3-a]pyrazin-7(8H)-yl)methanone.
(S)-(2-chloro-3-(trifluoromethyl)phenyl)(3-(3,4-difluorophenyl)-6-methyl-5,6-dihydro-[1,2,4]triazolo[4,3-a]pyrazin-7(8H)-yl)methanone
(S)-(2,3-dichloro-4-fluorophenyl)(3-(3,4-difluorophenyl)-6-methyl-5,6-dihydro-[1,2,4]triazolo[4,3-a]pyrazin-7(8H)-yl)methanone
(S)-(2,3-dichlorophenyl)(3-(2,4-difluorophenyl)-6-methyl-5,6-dihydro-[1,2,4]triazolo[4,3-a]pyrazin-7(8H)-yl)methanone
(S)-(2-chloro-3-(trifluoromethyl)phenyl)(3-(2,4-difluorophenyl)-6-methyl-5,6-dihydro-[1,2,4]triazolo[4,3-a]pyrazin-7(8H)-yl)methanone
(S)-(2,3-dichloro-4-fluorophenyl)(3-(2,4-difluorophenyl)-6-methyl-5,6-dihydro-[1,2,4]triazolo[4,3-a]pyrazin-7(8H)-yl)methanone
(2-chloro-3-(trifluoromethyl)phenyl)(3-methyl-8-phenyl-5,6-dihydro-[1,2,4]triazolo[4,3-a]pyrazin-7(8H)-yl)methanone
(S)-(2,3-dichlorophenyl)(3-(6-fluoropyridin-2-yl)-6-methyl-5,6-dihydro-[1,2,4]triazolo[4,3-a]pyrazin-7(8H)-yl)methanone
(S)-(2,3-dichlorophenyl)(3-(4-methoxypyridin-2-yl)-6-methyl-5,6-dihydro-[1,2,4]triazolo[4,3-a]pyrazin-7(8H)-yl)methanone
(2-chlorophenyl)(6-methyl-3-phenyl-5,6-dihydro-[1,2,4]triazolo[4,3-a]pyrazin-7(8H)-yl)methanone TABLE 1-continued (3,4-difluoro-2-methylphenyl)(6-methyl-3-phenyl-5,6-dihydro-
[1,2,4]triazolo[4,3-a]pyrazin-7(8H)-yl)methanone
(2-chloro-4-fluorophenyl)(6-methyl-3-phenyl-5,6-dihydro-[1,2,4]triazolo[4,3-
a]pyrazin-7(8H)-yl)methanone
(2,3-dichloropyridin-4-yl)(6-methyl-3-phenyl-5,6-dihydro-[1,2,4]triazolo[4,3-
a]pyrazin-7(8H)-yl)methanone
(3-cyclohexyl-8-methyl-5,6-dihydro-[1,2,4]triazolo[4,3-a]pyrazin-7(8H)-
yl)(2,3-dichlorophenyl)methanone
(2-chloro-3-(trifluoromethyl)phenyl)(3-cyclohexyl-8-methyl-5,6-dihydro-
[1,2,4]triazolo[4,3-a]pyrazin-7(8H)-yl)methanone
(3-cyclohexyl-8-methyl-5,6-dihydro-[1,2,4]triazolo[4,3-a]pyrazin-7(8H)-
yl)(2,3-dichloro-4-fluorophenyl)methanone
(3-cyclopropyl-8-methyl-5,6-dihydro-[1,2,4]triazolo[4,3-a]pyrazin-7(8H)-
yl)(2,3-dichlorophenyl)methanone
(3-cyclopropyl-8-methyl-5,6-dihydro-[1,2,4]triazolo[4,3-a]pyrazin-7(8H)-
yl)(2,3-dichloro-4-fluorophenyl)methanone
(2-chloro-3-(trifluoromethyl)phenyl)(3-cyclopropyl-8-methyl-5,6-dihydro-
[1,2,4]triazolo[4,3-a]pyrazin-7(8H)-yl)methanone
(S)-(2-chloro-3-(trifluoromethyl)phenyl)(3-methyl-8-phenyl-5,6-dihydro-
[1,2,4]triazolo[4,3-a]pyrazin-7(8H)-yl)methanone
(R)-(2-chloro-3-(trifluoromethyl)phenyl)(3-methyl-8-phenyl-5,6-dihydro-
[1,2,4]triazolo[4,3-a]pyrazin-7(8H)-yl)methanone
(S)-(2,3-dichlorophenyl)(3-(4-fluoropyridin-2-yl)-6-methyl-5,6-dihydro-
[1,2,4]triazolo[4,3-a]pyrazin-7(8H)-yl)methanone
(S)-(2,3-dichlorophenyl)(3-(5-fluoropyridin-2-yl)-6-methyl-5,6-dihydro-
[1,2,4]triazolo[4,3-a]pyrazin-7(8H)-yl)methanone
(S)-(2-chloro-3-(trifluoromethyl)phenyl)(3-(5-fluoropyridin-2-yl)-6-methyl-5,6-
dihydro-[1,2,4]triazolo[4,3-a]pyrazin-7(8H)-yl)methanone
((S)-(2-chloro-3-(trifluoromethyl)phenyl)(3-(5-methoxypyridin-2-yl)-6-methyl-
5,6-dihydro-[1,2,4]triazolo[4,3-a]pyrazin-7(8H)-yl)methanone
(S)-(2,3-dichlorophenyl)(3-(5-methoxypyridin-2-yl)-6-methyl-5,6-dihydro-
[1,2,4]triazolo[4,3-a]pyrazin-7(8H)-yl)methanone
(S)-(2,3-dichlorophenyl)(3-(5-fluoropyrimidin-2-yl)-6-methyl-5,6-dihydro-
[1,2,4]triazolo[4,3-a]pyrazin-7(8H)-yl)methanone
(S)-(2,3-dichlorophenyl)(3-(5-fluoropyrimidin-2-yl)-6-methyl-5,6-dihydro-
[1,2,4]triazolo[4,3-a]pyrazin-7(8H)-yl)methanone
(±)-(2-chloro-3-(trifluoromethyl)phenyl)(8-phenyl-3-(trifluoromethyl)-5,6-
dihydro-[1,2,4]triazolo[4,3-a]pyrazin-7(8H)-yl)methanone
(S)-(2-chloro-3-(trifluoromethyl)phenyl)(3-cyclopropyl-8-phenyl-5,6-dihydro-
[1,2,4]triazolo[4,3-a]pyrazin-7(8H)-yl)methanone
(R)-(2-chloro-3-(trifluoromethyl)phenyl)(3-cyclopropyl-8-phenyl-5,6-dihydro-
[1,2,4]triazolo[4,3-a]pyrazin-7(8H)-yl)methanone
(S)-(2-chloro-3-(trifluoromethyl)phenyl)(3-(5-methoxypyrimidin-2-yl)-6-
methyl-5,6-dihydro-[1,2,4]triazolo[4,3-a]pyrazin-7(8H)-yl)methanone
(±)-(2-chloro-3-(trifluoromethyl)phenyl)(3-(furan-2-yl)-8-phenyl-5,6-dihydro-
[1,2,4]triazolo[4,3-a]pyrazin-7(8H)-yl)methanone
(±)-(2-chloro-3-(trifluoromethyl)phenyl)(3-(1-hydroxyethyl)-8-phenyl-5,6-
dihydro-[1,2,4]triazolo[4,3-a]pyrazin-7(8H)-yl)methanone
(R)-(3-(tert-butyl)-8-phenyl-5,6-dihydro-[1,2,4]triazolo[4,3-a]pyrazin-7(8H)-
yl)(2-chloro-3-(trifluoromethyl)phenyl)methanone
(S)-(3-(tert-butyl)-8-phenyl-5,6-dihydro-[1,2,4]triazolo[4,3-a]pyrazin-7(8H)-
yl)(2-chloro-3-(trifluoromethyl)phenyl)methanone
(R)-(2-chloro-3-(trifluoromethyl)phenyl)(3-(furan-2-yl)-8-phenyl-5,6-dihydro-
[1,2,4]triazolo[4,3-a]pyrazin-7(8H)-yl)methanone
(S)-(2-chloro-3-(trifluoromethyl)phenyl)(3-(furan-2-yl)-8-phenyl-5,6-dihydro-
[1,2,4]triazolo[4,3-a]pyrazin-7(8H)-yl)methanone
(±)-(2-chloro-3-(trifluoromethyl)phenyl)(3-methyl-8-(pyridin-2-yl)-5,6-dihydro-
[1,2,4]triazolo[4,3-a]pyrazin-7(8H)-yl)methanone
(R)-(2-chloro-3-(trifluoromethyl)phenyl)(3-ethyl-8-phenyl-5,6-dihydro-
[1,2,4]triazolo[4,3-a]pyrazin-7(8H)-yl)methanone
(S)-(2-chloro-3-(trifluoromethyl)phenyl)(3-ethyl-8-phenyl-5,6-dihydro-
[1,2,4]triazolo[4,3-a]pyrazin-7(8H)-yl)methanone
(R)-(2-chloro-3-(trifluoromethyl)phenyl)(3-isopropyl-8-phenyl-5,6-dihydro-
[1,2,4]triazolo[4,3-a]pyrazin-7(8H)-yl)methanone
(S)-(2-chloro-3-(trifluoromethyl)phenyl)(3-isopropyl-8-phenyl-5,6-dihydro-
[1,2,4]triazolo[4,3-a]pyrazin-7(8H)-yl)methanone
(±)-(2,3-dichlorophenyl)(8-phenyl-3-(trifluoromethyl)-5,6-dihydro-
[1,2,4]triazolo[4,3-a]pyrazin-7(8H)-yl)methanone
(R)-(2-chloro-3-(trifluoromethyl)phenyl)(3-methyl-8-(pyridin-2-yl)-5,6-
dihydro-[1,2,4]triazolo[4,3-a]pyrazin-7(8H)-yl)methanone
(S)-(2-chloro-3-(trifluoromethyl)phenyl)(3-methyl-8-(pyridin-2-yl)-5,6-dihydro-
[1,2,4]triazolo[4,3-a]pyrazin-7(8H)-yl)methanone
(R)-(2-chloro-3-(trifluoromethyl)phenyl)(3-cyclobutyl-8-phenyl-5,6-dihydro-
[1,2,4]triazolo[4,3-a]pyrazin-7(8H)-yl)methanone
(S)-(2-chloro-3-(trifluoromethyl)phenyl)(3-cyclobutyl-8-phenyl-5,6-dihydro-
[1,2,4]triazolo[4,3-a]pyrazin-7(8H)-yl)methanone
(R*)-(2-chloro-4-fluoro-3-(trifluoromethyl)phenyl)(8-phenyl-3-
(trifluoromethyl)-5,6-dihydro-[1,2,4]triazolo[4,3-a]pyrazin-7(8H)-
yl)methanone TABLE 1-continued (S*)-(2-chloro-4-fluoro-3-(trifluoromethyl)phenyl)(8-phenyl-3-
(trifluoromethyl)-5,6-dihydro-[1,2,4]triazolo[4,3-a]pyrazin-7(8H)-
yl)methanone
(R)-(2-chloro-3-(trifluoromethyl)phenyl)(8-phenyl-3-(trifluoromethyl)-5,6-
dihydro-[1,2,4]triazolo[4,3-a]pyrazin-7(8H)-yl)methanone
(S)-(2-chloro-3-(trifluoromethyl)phenyl)(8-phenyl-3-(trifluoromethyl)-5,6-
dihydro-[1,2,4]triazolo[4,3-a]pyrazin-7(8H)-yl)methanone
(R*)-(3-chloro-2-(trifluoromethyl)pyridin-4-yl)(8-phenyl-3-(trifluoromethyl)-
5,6-dihydro-[1,2,4]triazolo[4,3-a]pyrazin-7(8H)-yl)methanone
(S*)-(3-chloro-2-(trifluoromethyl)pyridin-4-yl)(8-phenyl-3-(trifluoromethyl)-
5,6-dihydro-[1,2,4]triazolo[4,3-a]pyrazin-7(8H)-yl)methanone
(±)-(2-chloro-3-(trifluoromethyl)phenyl)(8-(4-fluorophenyl)-3-methyl-5,6-
dihydro-[1,2,4]triazolo[4,3-a]pyrazin-7(8H)-yl)methanone
(R)-(2,3-dichlorophenyl)(8-phenyl-3-(trifluoromethyl)-5,6-dihydro-
[1,2,4]triazolo[4,3-a]pyrazin-7(8H)-yl)methanone
(S)-(2,3-dichlorophenyl)(8-phenyl-3-(trifluoromethyl)-5,6-dihydro-
[1,2,4]triazolo[4,3-a]pyrazin-7(8H)-yl)methanone
(R)-(2,3-dichlorophenyl)(8-(4-fluorophenyl)-3-methyl-5,6-dihydro-
[1,2,4]triazolo[4,3-a]pyrazin-7(8H)-yl)methanone
(S)-(2,3-dichlorophenyl)(8-(4-fluorophenyl)-3-methyl-5,6-dihydro-
[1,2,4]triazolo[4,3-a]pyrazin-7(8H)-yl)methanone
(R)-(2-chloro-3-(trifluoromethyl)phenyl)(3-cyclopropyl-8-(4-fluorophenyl)-5,6-
dihydro-[1,2,4]triazolo[4,3-a]pyrazin-7(8H)-yl)methanone
(S)-(2-chloro-3-(trifluoromethyl)phenyl)(3-cyclopropyl-8-(4-fluorophenyl)-5,6-
dihydro-[1,2,4]triazolo[4,3-a]pyrazin-7(8H)-yl)methanone
(R)-(2-chloro-3-(trifluoromethyl)phenyl)(3-(difluoromethyl)-8-phenyl-5,6-
dihydro-[1,2,4]triazolo[4,3-a]pyrazin-7(8H)-yl)methanone
(S)-(2-chloro-3-(trifluoromethyl)phenyl)(3-(difluoromethyl)-8-phenyl-5,6-
dihydro-[1,2,4]triazolo[4,3-a]pyrazin-7(8H)-yl)methanone
(R)-(2,3-dichlorophenyl)(3-(difluoromethyl)-8-phenyl-5,6-dihydro-
[1,2,4]triazolo[4,3-a]pyrazin-7(8H)-yl)methanone
(S)-(2,3-dichlorophenyl)(3-(difluoromethyl)-8-phenyl-5,6-dihydro-
[1,2,4]triazolo[4,3-a]pyrazin-7(8H)-yl)methanone
(R)-(2,3-dichlorophenyl)(3-methyl-8-(pyridin-2-yl)-5,6-dihydro-
[1,2,4]triazolo[4,3-a]pyrazin-7(8H)-yl)methanone
(S)-(2,3-dichlorophenyl)(3-methyl-8-(pyridin-2-yl)-5,6-dihydro-
[1,2,4]triazolo[4,3-a]pyrazin-7(8H)-yl)methanone
(R)-(2-chloro-3-(trifluoromethyl)phenyl)(8-(4-fluorophenyl)-3-methyl-5,6-
dihydro-[1,2,4]triazolo[4,3-a]pyrazin-7(8H)-yl)methanone
(S)-(2-chloro-3-(trifluoromethyl)phenyl)(8-(4-fluorophenyl)-3-methyl-5,6-
dihydro-[1,2,4]triazolo[4,3-a]pyrazin-7(8H)-yl)methanone
(R)-(8-(4-fluorophenyl)-3-methyl-5,6-dihydro-[1,2,4]triazolo[4,3-a]pyrazin-
7(8H)-yl)(2-methyl-3-(trifluoromethyl)phenyl)methanone
(S)-(8-(4-fluorophenyl)-3-methyl-5,6-dihydro-[1,2,4]triazolo[4,3-a]pyrazin-
7(8H)-yl)(2-methyl-3-(trifluoromethyl)phenyl)methanone
(R)-(2-chloro-4-fluorophenyl)(8-phenyl-3-(trifluoromethyl)-5,6-dihydro-
[1,2,4]triazolo[4,3-a]pyrazin-7(8H)-yl)methanone
(S)-(2-chloro-4-fluorophenyl)(8-phenyl-3-(trifluoromethyl)-5,6-dihydro-
[1,2,4]triazolo[4,3-a]pyrazin-7(8H)-yl)methanone
(R)-(2,4-dichlorophenyl)(8-phenyl-3-(trifluoromethyl)-5,6-dihydro-
[1,2,4]triazolo[4,3-a]pyrazin-7(8H)-yl)methanone
(S)-(2,4-dichlorophenyl)(8-phenyl-3-(trifluoromethyl)-5,6-dihydro-
[1,2,4]triazolo[4,3-a]pyrazin-7(8H)-yl)methanone
(R)-(2-methyl-3-(trifluoromethyl)phenyl)(8-phenyl-3-(trifluoromethyl)-5,6-
dihydro-[1,2,4]triazolo[4,3-a]pyrazin-7(8H)-yl)methanone
(S)-(2-methyl-3-(trifluoromethyl)phenyl)(8-phenyl-3-(trifluoromethyl)-5,6-
dihydro-[1,2,4]triazolo[4,3-a]pyrazin-7(8H)-yl)methanone
(R)-(2,3-dichloro-4-fluorophenyl)(8-phenyl-3-(trifluoromethyl)-5,6-dihydro-
[1,2,4]triazolo[4,3-a]pyrazin-7(8H)-yl)methanone
(S)-(2,3-dichloro-4-fluorophenyl)(8-phenyl-3-(trifluoromethyl)-5,6-dihydro-
[1,2,4]triazolo[4,3-a]pyrazin-7(8H)-yl)methanone
(±)-(8-(1H-pyrazol-5-yl)-3-(trifluoromethyl)-5,6-dihydro-[1,2,4]triazolo[4,3-
a]pyrazin-7(8H)-yl)(2-chloro-3-(trifluoromethyl)phenyl)methanone
(±)-(2-chloro-3-(trifluoromethyl)phenyl)(8-(pyridin-3-yl)-3-(trifluoromethyl)-
5,6-dihydro-[1,2,4]triazolo[4,3-a]pyrazin-7(8H)-yl)methanone
(R)-(2-fluoro-3-(trifluoromethyl)phenyl)(8-phenyl-3-(trifluoromethyl)-5,6-
dihydro-[1,2,4]triazolo[4,3-a]pyrazin-7(8H)-yl)methanone
(S)-(2-fluoro-3-(trifluoromethyl)phenyl)(8-phenyl-3-(trifluoromethyl)-5,6-
dihydro-[1,2,4]triazolo[4,3-a]pyrazin-7(8H)-yl)methanone
(±)-(2-chloro-3-(trifluoromethyl)phenyl)(6-methyl-8-phenyl-3-
(trifluoromethyl)-5,6-dihydro-[1,2,4]triazolo[4,3-a]pyrazin-7(8H)-
yl)methanone
(±)-benzyl-3-(trifluoromethyl)-5,6-dihydro-[1,2,4]triazolo[4,3-a]pyrazin-7(8H)-
yl)(2-chloro-3-(trifluoromethyl)phenyl)methanone.
S)-(2,3-dichlorophenyl)(3-(4-hydroxypyridin-2-yl)-6-methyl-5,6-dihydro-
[1,2,4]triazolo[4,3-a]pyrazin-7(8H)-yl)methanone TABLE 1-continued (S)-(2,3-dichlorophenyl)(3-(4-[$^{11}$C]methoxypyridin-2-yl)-6-methyl-5,6-dihydro-[1,2,4]triazolo[4,3-a]pyrazin-7(8H)-yl)methanone
(S)-(2,3-dichlorophenyl)(3-(4-[$^{18}$F]fluoropyridin-2-yl)-6-methyl-5,6-dihydro-[1,2,4]triazolo[4,3-a]pyrazin-7(8H)-yl)methanone An additional embodiment of the invention is a pharmaceutical composition comprising and effective amount of at least one compound in Table 1 and at least one pharmaceutically acceptable excipient.

Also within the scope of the invention are enantiomers and diastereomers of the compounds of Formula I. Also within the scope of the invention are the pharmaceutically acceptable salts of the compounds of Formula I, as well as the pharmaceutically acceptable salts of the enantiomers and diastereomers of the compounds of Formula I. Also within the scope of the invention are isotopic variations of compounds of Formula I, such as, e.g., deuterated compounds of Formula I.

An additional embodiment of the invention is a method of treating a subject suffering from or diagnosed with a disease, disorder, or medical condition mediated by P2X7 receptor activity, comprising administering to a subject in need of such treatment an effective amount of at least one compound selected from compounds of Formula (I):

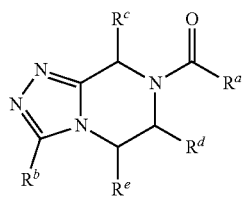

(I)

and enantiomers or diastereomers thereof;
and pharmaceutically acceptable salts thereof;
wherein:
$R^a$ is

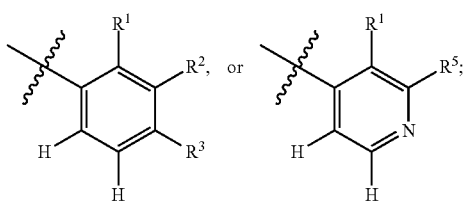

$R^1$ is halo or $C_1$-$C_3$alkyl;
$R^2$ is independently selected from the group consisting of: H, halo, and $C_1$-$C_3$perhaloalkyl;
$R^3$ is H or halo;
$R^4$ is halo,
$R^5$ is halo or $C_1$-$C_3$perhaloalkyl;

$R^b$ is independently selected from the group consisting of:

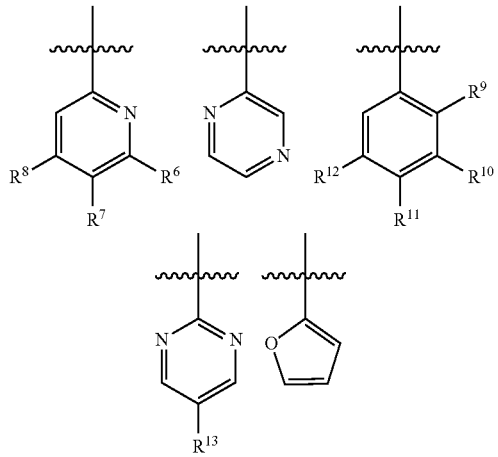

$C_3$-$C_6$ cycloalkyl $C_1$-$C_3$ perhaloalkyl $C_1$-$C_4$ alkyl and

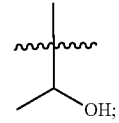

Wherein:
$R^6$, $R^9$, $R^{10}$, $R^{12}$, $R^{14}$ are independently H or halo;
$R^7$, $R^8$, $R^{13}$ is independently selected from the group consisting of: H, halo and $OC_1$-$C_3$alkyl;
$R^{11}$ is independently selected from the group consisting of: H, halo and $C_1$-$C_3$perhaloalkyl;
$R^c$ is selected from the group consisting of:

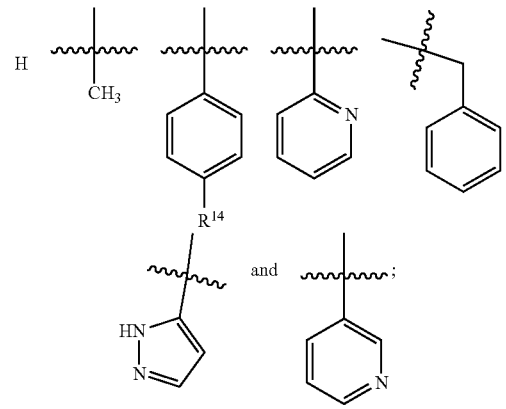

$R^d$ and $R^e$ are independently H or $C_1$-$C_3$alkyl; and
provided that at least one of $R^c$, $R^d$ and $R^e$ are not H.
In preferred embodiments of the inventive method, the disease, disorder, or medical condition is selected from:

diseases of the autoimmune and inflammatory system (Arulkumaran, N. et al. *Expert Opin. Invetig Drugs,* 2011, July; 20(7):897-915) [examples of diseases of the autoimmune and inflammatory system include rheumatoid arthritis, osteoarthritis, interstitial cystitis (Martins J P, et. al., *Br J Pharmacol.* 2012 January; 165(1):183-96), psoriasis (Killeen, M. E., et al., J Immunol. 2013 Apr. 15; 190(8): 4324-36), septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsiveness]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia) (Romagnoli, R, et. al., *Expert Opin. Ther. Targets,* 2008, 12(5), 647-661)], and diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety) (Friedle, S A, et. al., *Recent Patents on CNS Drug Discovery,* 2010, 5, 35-45, Romagnoli, R, et. al., 2008), cognition, sleep disorders, multiple sclerosis (Sharp A J, et. al., J Neuroinflammation. 2008 Aug. 8; 5:33, Oyanguren-Desez O, et. al., *Cell Calcium.* 2011 November; 50(5):468-72, Grygorowicz T, et. al., *Neurochem Int.* 2010 December; 57(7):823-9), epileptic seizures (Engel T, et. al., *FASEB J.* 2012 April; 26(4):1616-28, Kim J E, et. al. *Neurol Res.* 2009 November; 31(9):982-8, Avignone E, et. al., *J Neurosci.* 2008 Sep. 10; 28(37):9133-44), Parkinson's disease (Marcellino D, et. al., *J Neural Transm.* 2010 June; 117(6):681-7), schizophrenia, Alzheimer's disease (Diaz-Hernandez J I, et. al., *Neurobiol Aging.* 2012 August; 33(8):1816-28, Delarasse C, *J Biol Chem.* 2011 Jan. 28; 286(4):2596-606, Sanz J M, et. al., *J Immunol.* 2009 Apr. 1; 182(7):4378-85), Huntington's disease (Diaz-Hernández M, et. Al., *FASEB J.* 2009 June; 23(6):1893-906), Amyotrophic Lateral Sclerosis, autism, spinal cord injury, cerebral ischemia/traumatic brain injury (Chu K, et. al., *J Neuroinflammation.* 2012 Apr. 18; 9:69, Arbeloa J, et. al, *Neurobiol Dis.* 2012 March; 45(3):954-61) and stress-related disorders].

In addition, P2X7 intervention may be beneficial in diseases of the cardiovascular, metabolic, gastrointestinal and urogenital systems [examples of diseases of the cardiovascular, metabolic, gastrointestinal and urogenital systems include diabetes (*Arterioscler Thromb Vasc Biol.* 2004 July; 24(7):1240-5, *J Cell Physiol.* 2013 January; 228(1):120-9), diabetes mellitus, thrombosis (Furlan-Freguia C, et. al., *J Clin Invest.* 2011 July; 121(7):2932-44, Vergani, A. et al., *Diabetes,* 2013, 62, 1665-1675), irritable bowel disease, irritable bowel syndrome, (*J Immunol.* 2011 Aug. 1; 187(3): 1467-74. Epub 2011 Jun. 22), Crohn's disease, cardiovascular diseases (examples of cardiovascular disease include hypertension (Ji X, et. al., *Am J Physiol Renal Physiol.* 2012 October; 303(8):F1207-15), myocardial infarction, ischemic heart disease, ischemia) ureteric obstruction, lower urinary tract syndrome (*Br J Pharmacol.* 2012 January; 165(1):183-96), lower urinary tract dysfunction such as incontinence, and disease after cardiac transplant (Vergani, A. et al., *Circulation.* 2013; 127:463-475)].

P2X7 antagonism may also present a novel therapeutic strategy for skeletal disorders, (examples of skeletal disorders include osteoporosis/osteopetrosis) and may also modulate secretory function of exocrine glands.

It is also hypothesized that modulation of the P2X7 receptor may also be beneficial in conditions such as: glaucoma, Glomerulonephritis, Chaga's Disease, chlamydia, neuroblastoma, Tuberculosis, Polycystic Kidney Disease, cancer, and acne (Thiboutot, D. M. *J Investigative Dermatology,* 2014, 134, 595-597).

An additional embodiment of the invention is a method of treating a subject suffering from or diagnosed with a disease, disorder, or medical condition mediated by P2X7 receptor activity, wherein the disease, disorder, or medical condition is selected from the group consisting of: diseases of the autoimmune and inflammatory system [examples of diseases of the autoimmune and inflammatory system include rheumatoid arthritis, osteoarthritis, interstitial cystitis, psoriasis, septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsivenes]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia)]; diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, Amyotrophic Lateral Sclerosis, autism, spinal cord injury and cerebral ischemia/traumatic brain injury, and stress-related disorders]; diseases of the cardiovascular, metabolic, gastrointestinal and urogenital systems [examples of diseases of the cardiovascular, metabolic, gastrointestinal and urogenital systems include diabetes, diabetes mellitus, thrombosis, irritable bowel disease, irritable bowel syndrome, Crohn's disease, cardiovascular diseases (examples of cardiovascular disease include hypertension, myocardial infarction, ischemic heart disease, ischemia) ureteric obstruction, lower urinary tract syndrome, lower urinary tract dysfunction such as incontinence, and disease after cardiac transplantation]; skeletal disorders, (examples of skeletal disorders include osteoporosis/osteopetrosis) and diseases involving the secretory function of exocrine glands and diseases such as glaucoma, Glomerulonephritis, Chaga's Disease, chlamydia, neuroblastoma, Tuberculosis, Polycystic Kidney Disease, cancer, and acne.

An additional embodiment of the invention is a method of treating a subject suffering from or diagnosed with a disease, disorder, or medical condition mediated by P2X7 receptor activity wherein the disease, disorder or medical condition is a disease involved with, and without, neuroinflammation of the Central Nervous System (CNS).

An additional embodiment of the invention is a method of treating a subject suffering from or diagnosed with a disease involved with, and without, neuroinflammation of the Central Nervous System (CNS) wherein the disease, disorder or medical condition is a mood disorder.

An additional embodiment of the invention is a method of treating a subject suffering from a mood disorder wherein the mood disorder is treatment resistant depression.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "I"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_1$-$C_3$ alkyl as used here refers to a straight- or branched-chain alkyl group having from 1 to 3 carbon atoms in the chain. The term $C_1$-$C_4$ alkyl as used here refers to a straight- or branched-chain alkyl group having from 1 to 4 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "alkalkoxy" refers to the group alkyl-O-alkyl, where alkyl is defined above. Such groups include methylenemethoxy (—$CH_2OCH_3$) and ethylenemethoxy (—$CH_2CH_2OCH_3$).

The terms "hydroxyl" and "hydroxy" refer to an OH group.

The term "cycloalkyl" refers to a saturated carbocycle having from 3 to 6 ring atoms per carbocycle. Illustrative examples of cycloalkyl groups include the following entities, in the form of properly bonded moieties:

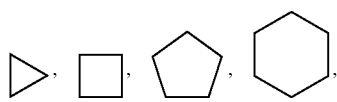

The term "$C_3$-$C_4$ cycloalkyl" as used here refers to a saturated carbocycle having from 3 to 4 ring atoms.

A "heterocycloalkyl" refers to a monocyclic ring structure that is saturated and has from 4 to 6 ring atoms per ring structure selected from carbon atoms and one nitrogen atom. Illustrative entities, in the form of properly bonded moieties include:

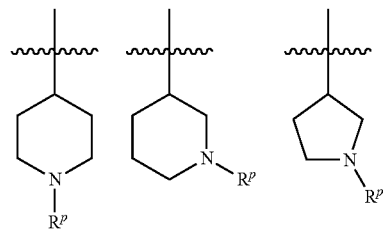

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

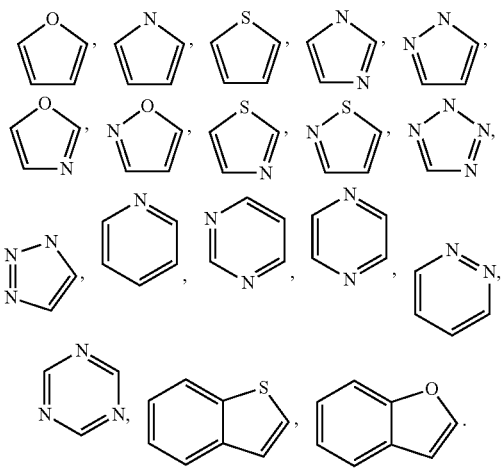

Those skilled in the art will recognize that the species of heteroaryl, cycloalkyl, aryl and heterocycloalkyl groups listed or illustrated above are not exhaustive, and that additional species within the scope of these defined terms may also be selected.

The term "cyano" refers to the group —CN.

The term "halo" represents chloro, fluoro, bromo or iodo.

The term "perhaloalkyl" refers to a straight- or branched-chain alkyl group having from 1 to 4 carbon atoms in the chain optionally substituting hydrogens with halogens. Examples of perhaloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

The term "perhaloalkoxy" refers to a straight- or branched-chain alkoxy group having from 1 to 4 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), momofluoroethoxy ($OCH_2CH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy ($-OCF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

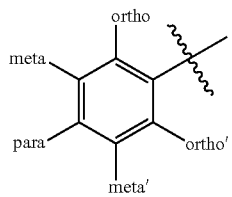

When referring to substituents on a pyridyl group, the terms "para", "meta", and "ortho" refer to the placement of a substituent relative to the point of attachment of the pyridyl ring. For example the structure below is described as 4-pyridyl with the X substituent in the ortho position and the Y substituent in the meta position:

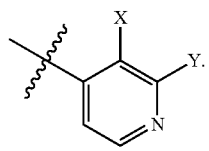

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (-)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting in a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COOH$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmcopoeia or other generally recognized pharmacopoeia for use in animals, and more particularly, in humans.

A "pharmaceutically acceptable salt" is intended to mean a salt of a free acid or base of compounds represented by Formula (I) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I, IIa or IIb). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$ alkyl amines and secondary di($C_{1-6}$ alkyl) amines. Secondary amines include 5- or 6-membered heterocycloalkyl or heteroaryl ring moieties. Examples of amides include those that are derived from ammonia, $C_{1-3}$ alkyl primary amines, and di($C_{1-2}$ alkyl)amines. Examples of esters of the invention include $C_{1-7}$ alkyl, $C_{6-7}$ cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I, IIa or IIb) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the P2X7 receptor expression or activity, and "activators" are compounds that increase, activate, facilitate, sensitize, or up-regulate P2X7 receptor expression or activity.

The term "treat", "treatment" or "treating", as used herein, is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: diseases of the autoimmune and inflammatory system [examples of diseases of the autoimmune and inflammatory system include rheumatoid arthritis, osteoarthritis, interstitial cystitis, psoriasis, septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsivenes]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia)]; diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, Amyotrophic Lateral Sclerosis, autism, spinal cord injury and cerebral ischemia/traumatic brain injury, and stress-related disorders]; diseases of the cardiovascular, metabolic, gastrointestinal and urogenital systems [examples of diseases of the cardiovascular, metabolic, gastrointestinal and urogenital systems include diabetes, diabetes mellitus, thrombosis, irritable bowel disease, irritable bowel syndrome, Crohn's disease, cardiovascular diseases (examples of cardiovascular disease include hypertension, myocardial infarction, ischemic heart disease, ischemia) ureteric obstruction, lower urinary tract syndrome, lower urinary tract dysfunction such as incontinence, and disease after cardiac transplantation]; skeletal disorders, (examples of skeletal disorders include osteoporosis/osteopetrosis) and diseases involving the secretory function of exocrine glands and diseases such as glaucoma, Glomerulonephritis, Chaga's Disease, chlamydia, neuroblastoma, Tuberculosis, Polycystic Kidney Disease, cancer, and acne.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Tables 1 or included with such an agent in a pharmaceutical composition according to the invention. In an exemplary embodiment, additional active ingredients are those that are known or discovered to be effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Schemes

The group PG represents a protecting group. One skilled in the art will select the appropriate protecting group compatible with the desired reactions. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Examples of preferred protecting groups include; carbamates, benzyl and substituted benzyl groups. Especially preferred protecting groups are tert-butyloxycarbonyl and benzyl.

Scheme 1

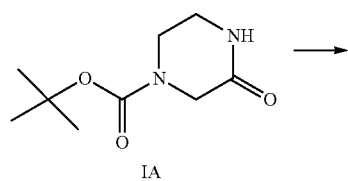

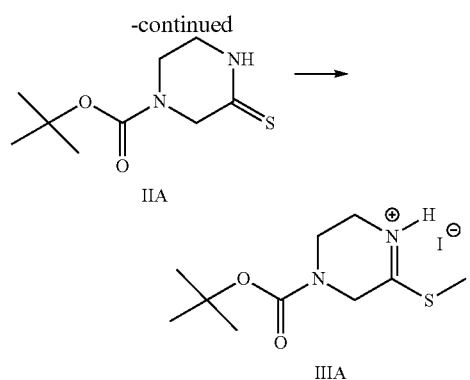

Compound IA can be converted to compound IIA by reaction with Lawesson's reagent, in a solvent such as THF, diethyl ether or DCM. This reaction may be performed at room temperature or heated overnight at or near the boiling point of the solvent.

Compound IIA may be converted to amine IIIA by treatment with an alkylating agent such as trimethyloxonium tetrafluoroborate or methyl iodide in a solvent such as DCM or DMF, at a temperature of between room temperature and 40° C. for between 1 and 48 hours.

Scheme 2A

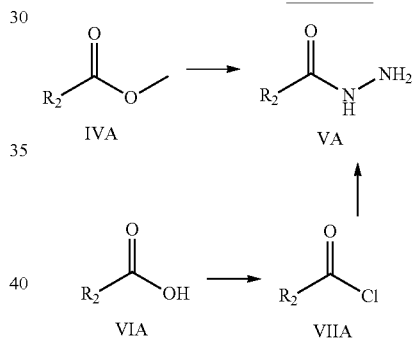

Scheme 2B

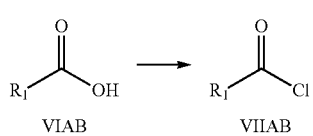

Compound IVA may be converted to compound VA by treatment with hydrazine monohydrate in a solvent such as an alcohol, DCM or DMF at a temperature near room temperature for from 1 to 25 hours. Compound VIA may be converted to compound VIIA by treatment with an appropriate acylating agent such as oxalyl chloride in the presence of a catalyst such as DMF in a solvent such as DCM or DMF for from 1 to 8 hours. Compound VIIA may then also be converted to compound VA by treatment with hydrazine monohydrate in a solvent such as an alcohol, DCM or DMF at a temperature near room temperature for from 1 to 12 hours. Additionally compound VIAB may be converted to compound VIIAB by treatment with an appropriate acylating agent such as oxalyl chloride in the presence of a catalyst such as DMF in a solvent such as DCM or DMF for from 1 to 8 hours. If compounds of type IVA, VIA or VIAB are not commercially available, one skilled in the art will realize there are numerous methods for synthesizing these compounds. These may include hydrolysis of the corresponding nitrile to afford VIA followed by esterification to give IVA. The nitrile in turn can be obtained from a cross-coupling reaction with a suitable halogen containing compound. Hydrolysis of the corresponding nitrile to could also afford VIAB. Or VIA or VIAB can be directly formed from the halogen compound via metal halogen exchange followed by quenching with $CO_2$. VIA or VIAB can also be formed by oxidation of a suitable methyl substituted compound with a reagent, such as, $KMnO_4$ and then IVA may be formed by subsequent esterification of VIA. These compounds can also be formed by oxidation of an appropriately substituted hydroxymethyl compound in either one or two steps to afford VIA or VIAB.

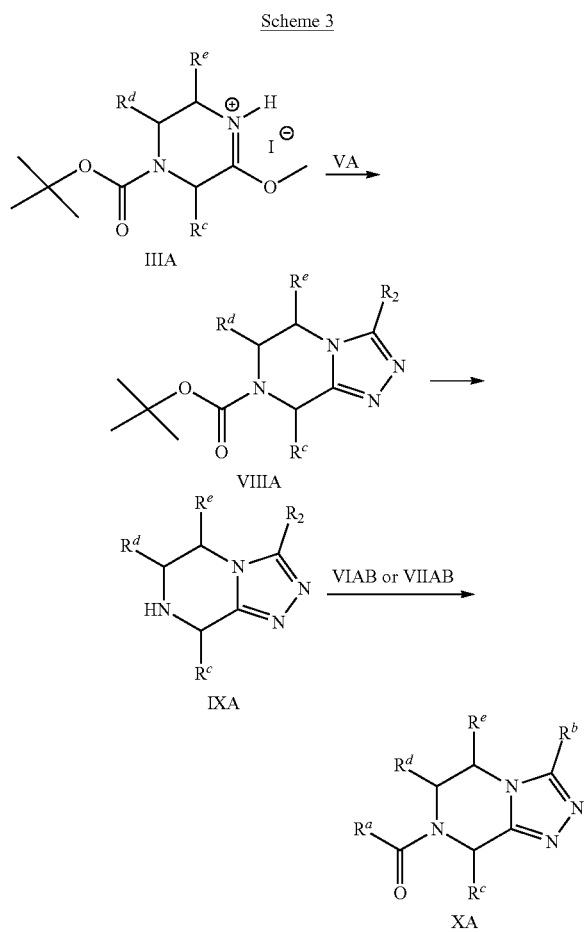

Scheme 3

Compound IIIA may be converted to compound VIIIA by the addition of compound VA and a suitable base such as potassium t-butoxide in an alcohol solvent such as methanol. This reaction can be performed at a temperature from room temperature to 120° C. for from 30 minutes to 48 hours. Compound VIIIA can then be converted to compound IXA by addition of a suitable acid such as HCl or TFA, preferably TFA in a solvent such as DCM, DCE or dioxane. This reaction can be performed at a temperature from room temperature to 50° C. for from 30 minutes to 24 hours.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I, IIa and IIb). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Corporation Discover instrument. Hydrogenations on the H-cube were run by passing solvent containing reactant through a catalyst cartridge on an H-Cube hydrogenation apparatus at a pressure of 15 to 100 bar and a flow rate of 1 to 30 ml/min.

Normal-phase silica gel column chromatography (sgc) was performed on silica gel ($SiO_2$) using prepackaged cartridges, eluting with 2 M $NH_3$/MeOH in $CH_2Cl_2$ unless otherwise indicated.

Preparative reverse-phase high performance liquid chromatography (HPLC) was performed on a Agilent HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 or 80 m L/m in, unless otherwise indicated.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

A notation of (±) or R/S indicates that the product is a racemic mixture of enantiomers and/or diastereomers. A notation of, for example, (2S,3R) indicates that product stereochemistry depicted is based on the known stereochemistry of similar compounds and/or reactions. A notation of, for example, (2S*, 3R*) indicates that the product is a pure and single diastereomer but the absolute stereochemistry is not established and relative stereochemistry is shown.

Chemical names were generated using ChemDraw Ultra 6.0.2 (CambridgeSoft Corp., Cambridge, MA).

Abbreviations and acronyms used herein include the following:

| Term | Acronym/Abbreviation |
|---|---|
| Reverse Phase High-pressure liquid chromatography | HPLC or RP HPLC |
| Tetrahydrofuran | THF |
| tert-Butylcarbamoyl | Boc, BOC |
| Dichloromethane | DCM |
| Trifluoroacetic acid | TFA |
| N,N-Dimethylformamide | DMF |
| Methanol | MeOH |
| Ethanol | EtOH |
| Isopropanol | IPA, iPrOH |
| n-butanol | n-BuOH |
| Acetonitrile | ACN, MeCN |
| Ethyl Acetate | EtOAc, or EA |
| Triethylamine | TEA |
| 1-Ethyl-3-(3-dimethylaminopropyl)carbodiimide | EDCI |
| Dimethyl sulfoxide | DMSO |
| Hexane | HEX |
| Supercritical fluid chromatography | SFC |
| Sodium Acetate | NaOAc |
| Room Temperature | RT, rt |

Example 1: (2,3-dichlorophenyl)(8-methyl-3-(pyridin-2-yl)-5,6-dihydro-[1,2,4]triazolo[4,3-a]pyrazin-7(8H)-yl)methanone

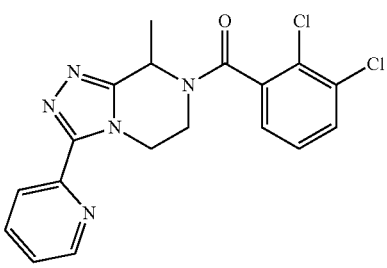 [SMILES: CC1c2nnc(-c3ccccn3)n2CCN1C(=O)c1cccc(Cl)c1Cl]

Example 1, Step a: tert-Butyl 2-methyl-3-oxopiperazine-1-carboxylate. To 3-methylpiperazin-2-one (1.08 g, 9.33 mmol) in 1:1 THF/H$_2$O (45 mL) was added Na$_2$CO$_3$ (2.08 g, 19.60 mmol) and BOC-anhydride (2.24 g, 10.27 mmol). The reaction was allowed to stir for 4 h, then extracted with DCM. The combined organics were washed 1× with brine, dried over Na$_2$SO$_4$, filtered and concentrated in vacuo (2.00 g, 99%). MS (ESI) mass calcd. C$_{10}$H$_{18}$N$_2$O$_3$, 214.13; m/z found 429.0 [2M+H]$^+$, 159.0 [M+H-tBu]$^+$. 1H NMR (500 MHz, CDCl$_3$): 8.05 (s, 1H), 4.42 (s, 2H), 3.69-3.61 (m, 2H), 2.63 (s, 2H), 1.49 (s, 9H).

Example 1, Step b: tert-Butyl 8-methyl-3-(pyridin-2-yl)-5,6-dihydro-[1,2,4]triazolo[4,3-a]pyrazine-7(8H)-carboxylate. To a solution of the product of Example 1, step a (230 mg, 1.08 mmol) in DCM (5 mL) was added trimethyloxonium tetrafluoroborate (194 mg, 1.25 mmol). The reagent slowly dissolved and after stirring overnight all of the starting material was consumed. To this solution was added 2-picolinyl hydrazide (181 mg, 1.29 mmol). After 24 h the reaction was concentrated in vacuo and dissolved in dioxane (2 mL) and saturated aqueous NaHCO$_3$ solution (2 mL). The mixture was heated for 3 h at 90° C. and the dioxane was removed in vacuo and the aqueous layer extracted with DCM and EtOAc. The combined organic extracts were dried over Na$_2$SO$_4$ filtered and concentrated in vacuo. Chromatography on SiO$_2$ eluting with IPA/EtOAc afforded the title compound (150 mg, 44%). MS (ESI) mass calcd. C$_{16}$H$_{21}$N$_5$O$_2$, 315.17; m/z found 316.0 [M+H]$^+$.

Example 1, Step c: 8-methyl-3-(pyridin-2-yl)-5,6,7,8-tetrahydro-[1,2,4]triazolo[4,3-a]pyrazine. To the product of Example 1, step b (150 mg, 0.48 mmol) in DCM (2 mL) was added TFA (0.48 mL). After stirring 3 h, the reaction was concentrated in vacuo. The residue was redissolved in DCM and treated with Dowex 550 A resin. The resin was removed by filtration and concentration afforded a white solid. Chromatography on SiO$_2$ eluting with 2M NH$_3$ in MeOH/DCM afforded the desired compound (100 mg, 98%). MS (ESI) mass calcd. C$_{11}$H$_{13}$N$_5$, 215.12; m/z found 216.0 [M+H]$^+$.

Example 1, step d: 7-[(2,3-Dichlorophenyl)carbonyl]-8-methyl-3-pyridin-2-yl-5,6,7,8-tetrahydro[1,2,4]triazolo[4,3-a]pyrazine. To a solution of the product of Example 1, step c (83 mg, 0.39 mmol) in DCM (4 mL) was added 2,4-dichlorobenzoic acid (74 mg, 0.39 mmol) followed by EDCI (111 mg, 0.58 mmol), HOBt (36 mg, 0.27 mmol) and TEA (0.11 mL, 0.77 mmol). The mixture was stirred overnight and then loaded directly on a column. Chromatography on SiO$_2$ eluting with EtOAc/Hex afforded impure material. Purification of this material on a Prep Agilent system with a XBridge C18 OBD 50×100 mm column eluting with 5 to 99% 0.05% NH$_4$OH in H$_2$O/ACN over 17 min afforded the desired product (51 mg, 34%). MS (ESI) mass calcd. C$_{18}$H$_{15}$Cl$_2$N$_5$O, 387.07; m/z found 387.9 [M+H]$^+$. 1H NMR (500 MHz, CDCl$_3$): 8.68-8.52 (m, 1H), 8.38-8.28 (m, 1H), 7.88-7.80 (m, 1H), 7.60-7.53 (m, 1H), 7.39-7.27 (m, 3H), 6.24-6.17 (m, 0.5H), 5.22-4.91 (m, 2H), 4.44-4.10 (m, 1H), 3.73-3.32 (m, 1.5H), 1.84-1.57 (m, 3H).

Example 2: (R)-(2,3-dichlorophenyl)(8-methyl-3-(pyridin-2-yl)-5,6-dihydro-[1,2,4]triazolo[4,3-a]pyrazin-7(8H)-yl)methanone

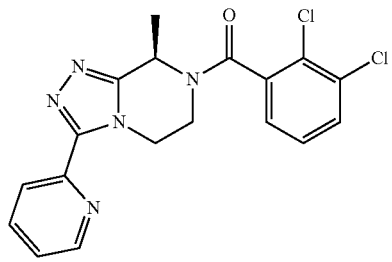 [SMILES: C[C@@H]1c2nnc(-c3ccccn3)n2CCN1C(=O)c1cccc(Cl)c1Cl]

Example 2, absolute configuration unknown, was obtained by chiral separation of Example 1 utilizing SFC.

Stationary Phase: Amycoat 5 μm 250×30 mm (L×I.D.) at 40° C.

Mobile Phase: 25.5 mL/min EtOH with 0.2% isopropylamine, 59.5 mL/min CO$_2$

Detection: UV 254 nm.

Example 2 was the second compound off the column (16 mg). MS (ESI) mass calcd. C$_{18}$H$_{15}$Cl$_2$N$_5$O, 387.07; m/z found 388.1 [M+H]$^+$. 1H NMR (500 MHz, CDCl$_3$): 8.67-8.53 (m, 1H), 8.37-8.29 (m, 1H), 7.87-7.80 (m, 1H), 7.59-7.54 (m, 1H), 7.38-7.23 (m, 3H), 6.24-6.17 (m, 0.5H), 5.23-4.89 (m, 2H), 4.43-4.10 (m, 1H), 3.74-3.61 (m, 1H), 3.59-3.32 (m, 0.5H), 1.85-1.55 (m, 3H).

Example 3: (S)-(2,3-dichlorophenyl)(8-methyl-3-(pyridin-2-yl)-5,6-dihydro-[1,2,4]triazolo[4,3-a]pyrazin-7(8H)-yl)methanone

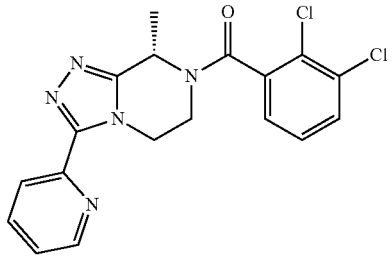 [SMILES: C[C@H]1c2nnc(-c3ccccn3)n2CCN1C(=O)c1cccc(Cl)c1Cl]

Example 3, absolute configuration unknown, was obtained by chiral separation of Example 1 utilizing SFC.

Stationary Phase: Amycoat 5 μm 250×30 mm (L×I.D.) at 40° C.

Mobile Phase: 25.5 mL/min EtOH with 0.2% isopropylamine, 59.5 mL/min $CO_2$

Detection: UV 254 nm.

Example 3 was the first compound off the column (16 mg). MS (ESI) mass calcd. $C_{18}H_{15}Cl_2N_5O$, 387.07; m/z found 388.1 [M+H]$^+$. 1H NMR (500 MHz, CDCl$_3$): 8.68-8.53 (m, 1H), 8.37-8.29 (m, 1H), 7.88-7.81 (m, 1H), 7.60-7.54 (m, 1H), 7.38-7.23 (m, 3H), 6.23-6.17 (m, 0.5H), 5.22-4.91 (m, 2H), 4.43-4.10 (m, 1H), 3.73-3.63 (m, 1H), 3.59-3.32 (m, 0.5H), 1.84-1.52 (m, 3H).

Examples 4-11 can be made in a manner analogous to Example 1, substituting the appropriate starting materials for each step.

Example 4: (2-chloro-3-(trifluoromethyl)phenyl)(5-methyl-3-phenyl-5,6-dihydro-[1,2,4]triazolo[4,3-a]pyrazin-7(8H)-yl)methanone

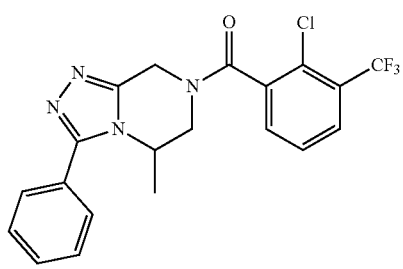 [SMILES: CC1CN(C(=O)c2cccc(C(F)(F)F)c2Cl)Cc2nnc(-c3ccccc3)n21]

Example 5: (2,3-dichlorophenyl)(5-methyl-3-phenyl-5,6-dihydro-[1,2,4]triazolo[4,3-a]pyrazin-7(8H)-yl)methanone

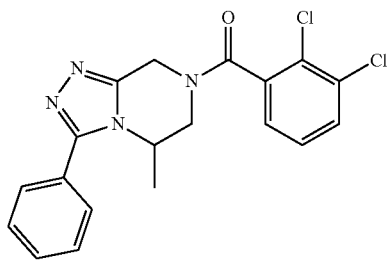 [SMILES: CC1CN(C(=O)c2cccc(Cl)c2Cl)Cc2nnc(-c3ccccc3)n21]

Example 6: (2-chloro-3-(trifluoromethyl)phenyl)(3-(4-fluorophenyl)-5-methyl-5,6-dihydro-[1,2,4]triazolo[4,3-a]pyrazin-7(8H)-yl)methanone

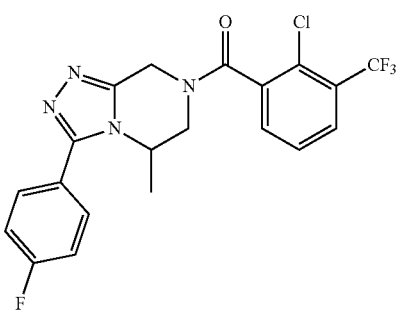 [SMILES: CC1CN(C(=O)c2cccc(C(F)(F)F)c2Cl)Cc2nnc(-c3ccc(F)cc3)n21]

Example 7: (2,3-dichlorophenyl)(3-(4-fluorophenyl)-5-methyl-5,6-dihydro-[1,2,4]triazolo[4,3-a]pyrazin-7(8H)-yl)methanone

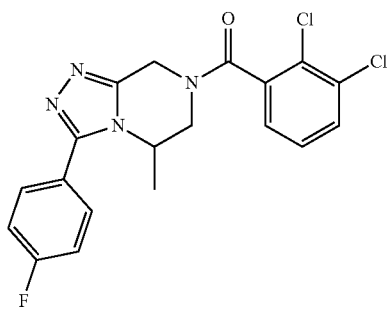 [SMILES: CC1CN(C(=O)c2cccc(Cl)c2Cl)Cc2nnc(-c3ccc(F)cc3)n21]

Example 8: (2-chloro-3-(trifluoromethyl)phenyl)(3-(4-fluorophenyl)-6-methyl-5,6-dihydro-[1,2,4]triazolo[4,3-a]pyrazin-7(8H)-yl)methanone

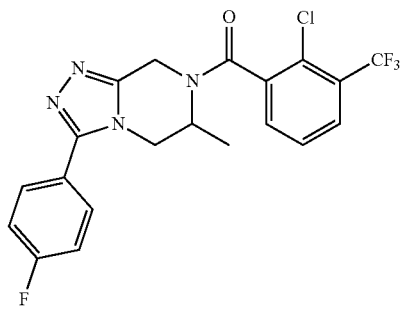 [SMILES: CC1Cn2c(nnc2-c2ccc(F)cc2)CN1C(=O)c1cccc(C(F)(F)F)c1Cl]

Example 9: (2,3-dichlorophenyl)(3-(4-fluorophenyl)-6-methyl-5,6-dihydro-[1,2,4]triazolo[4,3-a]pyrazin-7(8H)-yl)methanone

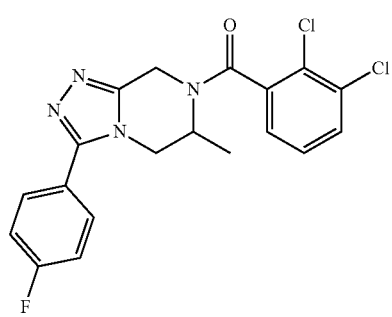 [SMILES: CC1Cn2c(nnc2-c2ccc(F)cc2)CN1C(=O)c1cccc(Cl)c1Cl]

Example 10: (2-chloro-3-(trifluoromethyl)phenyl)(6-methyl-3-phenyl-5,6-dihydro-[1,2,4]triazolo[4,3-a]pyrazin-7(8H)-yl)methanone

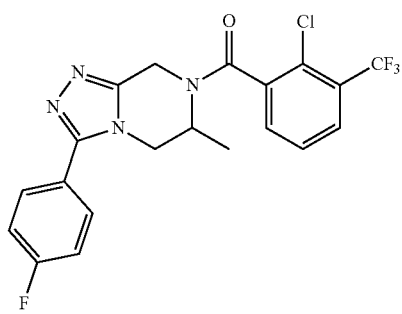 [SMILES: CC1Cn2c(nnc2-c2ccc(F)cc2)CN1C(=O)c1cccc(C(F)(F)F)c1Cl]

Example 11: (2,3-dichlorophenyl)(6-methyl-3-phenyl-5,6-dihydro-[1,2,4]triazolo[4,3-a]pyrazin-7(8H)-yl)methanone

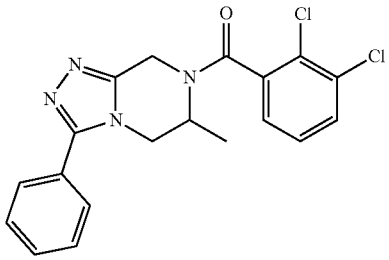 [SMILES: CC1Cn2c(nnc2-c2ccccc2)CN1C(=O)c1cccc(Cl)c1Cl]

Example 12: (R)-(2,3-dichlorophenyl)(6-methyl-3-phenyl-5,6-dihydro-[1,2,4]triazolo[4,3-a]pyrazin-7(8H)-yl)methanone

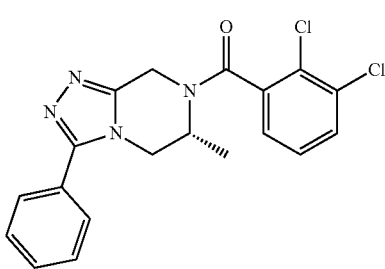 [SMILES: C[C@@H]1Cn2c(nnc2-c2ccccc2)CN1C(=O)c1cccc(Cl)c1Cl]

Example 12 was isolated following chiral SFC separation of Example 11 on a CHIRALCEL OD-H 5 μm 250×20 mm column with mobile phase consisting of 70% $CO_2$, 30% MeOH. Example 12 was the first eluting peak under these conditions. MS (ESI): mass calcd. for $C_{19}H_{16}Cl_2N_4O$, 386.1; m/z found, 386.10 $[M+H]^+$.

Example 13: (S)-(2,3-dichlorophenyl)(6-methyl-3-phenyl-5,6-dihydro-[1,2,4]triazolo[4,3-a]pyrazin-7(8H)-yl)methanone

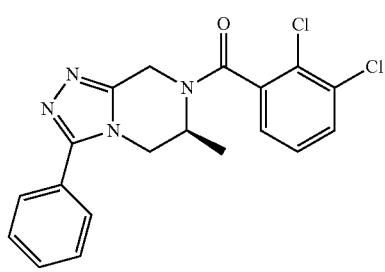 [SMILES: C[C@H]1Cn2c(nnc2-c2ccccc2)CN1C(=O)c1cccc(Cl)c1Cl]

Example 13 was isolated following chiral SFC separation of Example 11 on a CHIRALCEL OD-H 5 μm 250×20 mm column with mobile phase consisting of 70% $CO_2$, 30% MeOH. Example 13 was the second eluting peak under these conditions. MS (ESI): mass calcd. for $C_{19}H_{16}Cl_2N_4O$, 386.1; m/z found, 386.10 $[M+H]^+$.

Example 14: (R)-(2-chloro-3-(trifluoromethyl)phenyl)(6-methyl-3-phenyl-5,6-dihydro-[1,2,4]triazolo[4,3-a]pyrazin-7(8H)-yl)methanone

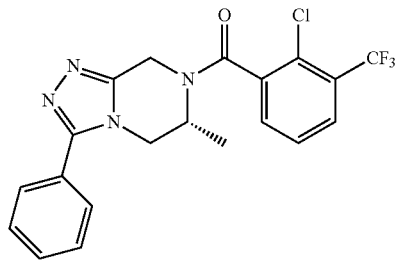 [SMILES: C[C@@H]1Cn2c(nnc2-c2ccccc2)CN1C(=O)c1cccc(C(F)(F)F)c1Cl]

Example 14 was isolated following chiral SFC separation of Example 10 on a CHIRALCEL OD-H 5 μm 250×20 mm column with mobile phase consisting of 75% $CO_2$, 25% MeOH. Example 14 was the first eluting peak under these conditions. MS (ESI): mass calcd. for $C_{20}H_{16}ClF_3N_4O$, 420.1; m/z found, 420.10 $[M+H]^+$.

Example 15: (S)-(2-chloro-3-(trifluoromethyl)phenyl)(6-methyl-3-phenyl-5,6-dihydro-[1,2,4]triazolo[4,3-a]pyrazin-7(8H)-yl)methanone

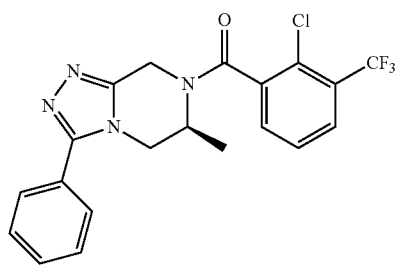 [SMILES: C[C@H]1Cn2c(nnc2-c2ccccc2)CN1C(=O)c1cccc(C(F)(F)F)c1Cl]

Example 15 was isolated following chiral SFC separation of Example 10 on a CHIRALCEL OD-H 5 μm 250×20 mm column with mobile phase consisting of 75% $CO_2$, 25% MeOH. Example 14 was the second eluting peak under these conditions. MS (ESI): mass calcd. for $C_{20}H_{16}ClF_3N_4O$, 420.1; m/z found, 420.10 $[M+H]^+$.

Example 16: (3-chloro-2-(trifluoromethyl)pyridin-4-yl)(8-methyl-3-(pyridin-2-yl)-5,6-dihydro-[1,2,4]triazolo[4,3-a]pyrazin-7(8H)-yl)methanone

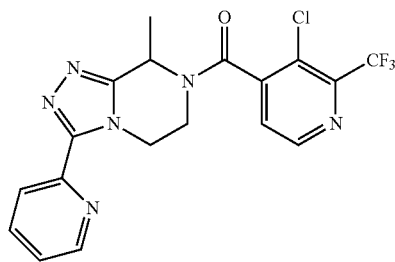

The title compound was prepared in a manner analogous to Example 1 substituting 3-chloro-2-(trifluoromethyl)isonicotinic acid for 2,3-dichlorobenzoic acid in Example 1, step d. MS (ESI) mass calcd. $C_{18}H_{14}ClF_3N_6O$, 422.09; m/z found 423.1 $[M+H]^+$. 1H NMR (500 MHz, $CDCl_3$): 8.76-8.52 (m, 2H), 8.37-8.30 (m, 1H), 7.89-7.81 (m, 1H), 7.54-7.46 (m, 1H), 7.41-7.30 (m, 1H), 6.23-6.15 (m, 1H), 5.25-4.91 (m, 2H), 4.43-4.08 (m, 1H), 3.80-3.36 (m, 2H), 1.85-1.61 (m, 3H).

Example 17: (2-chloro-3-(trifluoromethyl)phenyl)(8-methyl-3-(pyridin-2-yl)-5,6-dihydro-[1,2,4]triazolo[4,3-a]pyrazin-7(8H)-yl)methanone

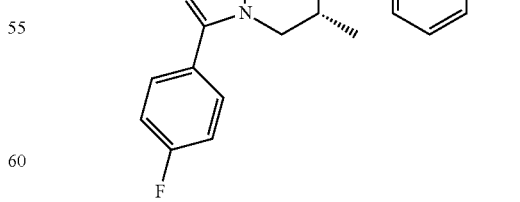

The title compound was prepared in a manner analogous to Example 1 substituting 2-chloro-3-(trifluoromethyl)benzoic acid for 2,3-dichlorobenzoic acid in Example 1, step d. MS (ESI) mass calcd. $C_{19}H_{15}ClF_3N_5O$, 421.09; m/z found 422.1 $[M+H]^+$. 1H NMR (500 MHz, $CDCl_3$): 8.67-8.51 (m, 1H), 8.37-8.29 (m, 1H), 7.88-7.79 (m, 2H), 7.59-7.30 (m, 3H), 6.25-6.18 (m, 1H), 5.21-4.93 (m, 2H), 4.42-4.11 (m, 1H), 3.76-3.33 (m, 1H), 1.85-1.58 (m, 3H).

Example 18: (R)-(2,3-dichlorophenyl)(3-(4-fluorophenyl)-6-methyl-5,6-dihydro-[1,2,4]triazolo[4,3-a]pyrazin-7(8H)-yl)methanone 1H NMR (400 MHz, DMSO) δ 7.91-7.34 (m, 7H), 5.72-5.39 (m, 1H), 4.76-3.70 (m, 4H), 1.27-0.96 (m, 3H). MS (ESI): mass calcd. for $C_{19}H_{15}Cl_2FN_4O$, 404.1; m/z found, 405.1 $[M+H]^+$.

Example 19: (S)-(2,3-dichlorophenyl)(3-(4-fluorophenyl)-6-methyl-5,6-dihydro-[1,2,4]triazolo[4,3-a]pyrazin-7(8H)-yl)methanone

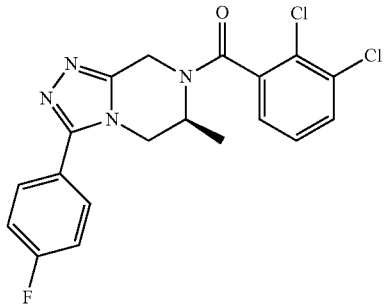

1H NMR (400 MHz, DMSO) δ 7.93-7.31 (m, 7H), 5.72-5.35 (m, 1H), 4.80-3.75 (m, 4H), 1.23-0.96 (m, 3H). MS (ESI): mass calcd. for $C_{19}H_{15}Cl_2FN_4O$, 404.1; m/z found, 405.1 $[M+H]^+$.

Example 20: (2-fluoro-3-(trifluoromethyl)phenyl)(8-methyl-3-(pyridin-2-yl)-5,6-dihydro-[1,2,4]triazolo[4,3-a]pyrazin-7(8H)-yl)methanone

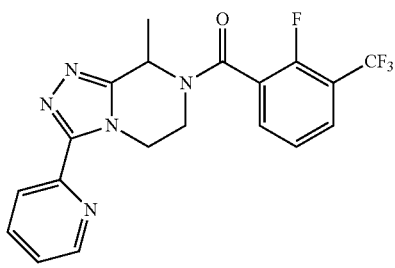 [SMILES: CC1c2nnc(-c3ccccn3)n2CCN1C(=O)c1cccc(C(F)(F)F)c1F]

The title compound was prepared in a manner analogous to Example 1 substituting 2-fluoro-3-(trifluoromethyl)benzoic acid for 2,3-dichlorobenzoic acid in Example 1, step d. MS (ESI) mass calcd. $C_{19}H_{15}F4N_5O$, 405.12; m/z found 406.1 $[M+H]^+$. 1H NMR (500 MHz, CDCl3): 8.68-8.54 (m, 1H), 8.37-8.29 (m, 1H), 7.87-7.52 (m, 3H), 7.43-7.31 (m, 2H), 6.19 (s, 1H), 5.22-4.96 (m, 2H), 4.43-4.17 (m, 1H), 3.85-3.37 (m, 1H), 1.86-1.65 (m, 3H).

Example 21: (S)-(2-chloro-3-(trifluoromethyl)phenyl)(3-(4-fluorophenyl)-6-methyl-5,6-dihydro-[1,2,4]triazolo[4,3-a]pyrazin-7(8H)-yl)methanone

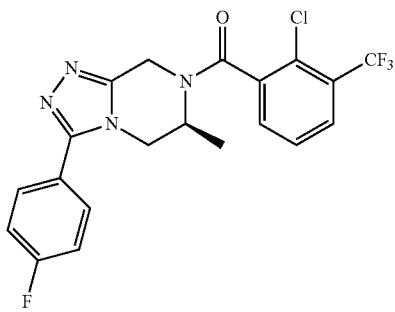 [SMILES: C[C@H]1Cn2c(nnc2-c2ccc(F)cc2)CN1C(=O)c1cccc(C(F)(F)F)c1Cl]

Intermediate 21A: (S)-tert-butyl (1-azidopropan-2-yl)carbamate

To a solution of Boc-L-alaninol (10.9 g, 61.7 mmol) in ether (300 mL) at 0° C. was added triethylamine (12.8 mL, 92.5 mmol) followed by methanesulonylchloride (4.8 mL, 61.7 mmol) and the reaction mixture was stirred to 1 hour. Water was added and the resulting reaction mixture was extracted with DCM. The organic layers were combined, dried, concentrated and the resulting residue was dissolved in DMF (100 mL). To the resulting solution was added sodium azide (8.0 g, 123.4 mmol) and the reaction mixture was heated to 70° C. for 18 hours. The reaction mixture was cooled to rt, water was added and the reaction mixture was extracted with EtOAc. The organic layers were combined, washed with brine, dried, concentrated and purified by flash column chromatography (0-50% EtOAc in hexanes) to provide (S)-tert-butyl (1-azidopropan-2-yl)carbamate (8.5 g). 1H NMR (400 MHz, DMSO) δ 7.05-6.84 (d, J=8.0 Hz, 1H), 3.72-3.55 (m, 1H), 3.26-3.19 (d, J=6.1 Hz, 2H), 1.42-1.36 (s, 9H), 1.06-0.99 (d, J=6.8 Hz, 3H).

Intermediate 21B: (S)-tert-butyl (1-(2-chloroacetamido)propan-2-yl)carbamate To a solution of (S)-tert-butyl (1-azidopropan-2-yl)carbamate (8.5 g, 42.4 mmol) in EtOAc (300 mL) was added 10% Pd/C (4.5 g) and the reaction mixture was placed under $H_2$ atmosphere (60 psi) for 2 hours. The reaction mixture was filtered through a pad of celite, concentrated and the resulting residue was taken up in DCM (300 mL). The resulting solution was cooled to −78° C. and triethylamine (8.9 mL) was added followed by chloroacetyl chloride (3.5 mL, 44.6 mmol). The reaction mixture was stirred at −78° C. for 20 minutes then warmed to 0° C. where it was stirred for 1 hour. Water was added and the resulting reaction mixture was extracted with DCM. The organic layers were combined, washed with brine, dried, concentrated and purified by flash column chromatography (0-100% EtOAc in hexanes) to provide (S)-tert-butyl (1-(2-chloroacetamido)propan-2-yl)carbamate (7.3 g). 1H NMR (400 MHz, DMSO) δ 8.28-8.10 (s, 1H), 6.79-6.60 (d, J=8.2 Hz, 1H), 4.16-3.97 (s, 2H), 3.64-3.48 (m, 1H), 3.13-2.99 (m, 2H), 1.44-1.30 (s, 9H), 1.05-0.91 (d, J=6.7 Hz, 3H).

Intermediate 21C: (S)-tert-butyl 2-methyl-5-oxopiperazine-1-carboxylate (S)-Tert-butyl (1-(2-chloroacetamido)propan-2-yl)carbamate (7.3 g, 29.1 mmol) was dissolved in trifluoroacetic acid (20 mL) and stirred at rt for 15 minutes. The reaction mixture was concentrated and the resulting residue was dissolved in THF (100 mL). To the resulting solution was added $K_2CO_3$ (20.1 g, 145.6 mmol) and the reaction mixture refluxed for 20 hours. The reaction mixture was cooled to 60° C. and catalytic DMAP was added followed by BOC-anhydride (12.5 mL, 58.2 mmol). The reaction mixture was stirred for 12 hours, water was added and the resulting reaction mixture was extracted with EtOAc. The organic layers were combined, dried, concentrated and purified by flash column chromatography (0-50% iPrOH in EtOAc) to provide (S)-tert-butyl 2-methyl-5-oxopiperazine-1-carboxylate (4.6 g). 1H NMR (400 MHz, DMSO) δ 8.08-7.90 (s, 1H), 4.31-4.09 (s, 1H), 4.00-3.87 (d, J=17.9 Hz, 1H), 3.63-3.51 (d, J=17.8 Hz, 1H), 3.37-3.33 (m, 1H), 3.04-2.93 (ddd, J=12.7, 4.9, 2.5 Hz, 1H), 1.46-1.35 (s, 9H), 1.15-1.06 (d, J=6.7 Hz, 3H).

Intermediate 21D: (S)-tert-butyl 3-(4-fluorophenyl)-6-methyl-5,6-dihydro-[1,2,4]triazolo[4,3-a]pyrazine-7(8H)-carboxylate To a solution of (S)-tert-butyl 2-methyl-5-oxopiperazine-1-carboxylate (1.3 g, 6.1 mmol) in DCM (31 mL) was added trimethyloxonium tetrafluoroborate (1.0 g, 6.8 mmol) and the reaction mixture was stirred at rt for 6 hours. 4-fluorobenzohydrazide (1.2 g, 8.0 mmol) was added and the reaction mixture was allowed to stir at rt overnight. The reaction mixture was concentrated via gentle N2 stream and the resulting residue was dissolved in dioxane (15 mL). To the resulting solution was added saturated aqueous sodium bicarbonate (15 mL) and the reaction mixture was refluxed for 12 hours. The reaction mixture was cooled to rt, diluted with EtOAc, washed with water, dried, concentrated and purified by flash column chromatography (0-10% MeOH in DCM) to provide (S)-tert-butyl 3-(4-fluorophenyl)-6-methyl-5,6-dihydro-[1,2,4]triazolo[4,3-a]pyrazine-7(8H)-carboxylate (1.2 g). MS (ESI) mass calcd. $C_{17}H_{21}FN_4O_2$, 332.4; m/z found, 333.2 $[M+H]^+$.

Intermediate 21E: (S)-3-(4-fluorophenyl)-6-methyl-5,6,7,8-tetrahydro-[1,2,4]triazolo[4,3-a]pyrazine (S)-Tert-butyl 3-(4-fluorophenyl)-6-methyl-5,6-dihydro-[1,2,4]triazolo[4,3-a]pyrazine-7(8H)-carboxylate (0.2 g, 0.6 mmol) was dissolved in trifluoroacetic acid and stirred at rt for 20 minutes. The reaction mixture was concentrated and the resulting residue was used without further purification.

To a solution of (S)-3-(4-fluorophenyl)-6-methyl-5,6,7,8-tetrahydro-[1,2,4]triazolo[4,3-a]pyrazine (90 mg, 0.387 mmol) and 2-chloro-3-(trifluoromethyl)benzoyl chloride (109 mg, 0.452 mmol) in DCM (10 mL) was added triethylamine (0.2 mL, 1.5 mmol) and the reaction mixture was stirred at rt for 1 hour. Water was added and the resulting reaction mixture was extracted with DCM. The organic layers were combined, dried, concentrated and purified by flash column chromatography (0-70% iPrOH in EtOAc) to provide (S)-(2-chloro-3-(trifluoromethyl)phenyl)(6-methyl-3-(pyrazin-2-yl)-5,6-dihydro-[1,2,4]triazolo[4,3-a]pyrazin-7(8H)-yl)methanone (70 mg). 1H NMR (400 MHz, DMSO) δ 7.93-7.31 (m, 7H), 5.72-5.35 (m, 1H), 4.80-3.75 (m, 4H), 1.23-0.96 (m, 3H). MS (ESI): mass calcd. for $C_{20}H_{15}ClF_4N_4O$, 438.1; m/z found, 439.1 $[M+H]^+$.

Example 22: (S)-(2,3-dichlorophenyl)(6-methyl-3-(pyrazin-2-yl)-5,6-dihydro-[1,2,4]triazolo[4,3-a]pyrazin-7(8H)-yl)methanone

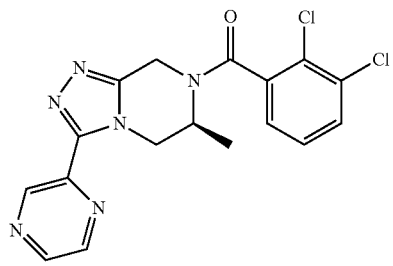 [SMILES: C[C@H]1Cn2c(nnc2-c2cnccn2)CN1C(=O)c1cccc(Cl)c1Cl]

(S)-(2,3-dichlorophenyl)(6-methyl-3-(pyrazin-2-yl)-5,6-dihydro-[1,2,4]triazolo[4,3-a]pyrazin-7(8H)-yl)methanone was generated in an analogous fashion to that described for (S)-(2-chloro-3-(trifluoromethyl)phenyl)(3-(4-fluorophenyl)-6-methyl-5,6-dihydro-[1,2,4]triazolo[4,3-a]pyrazin-7(8H)-yl)methanone where in 2,3-dichlorobenzoyl chloride was used in place of 2-chloro-3-(trifluoromethyl)benzoyl chloride and pyrazine-2-carbohydrazide was used in place of 4-fluorobenzohydrazide. 1H NMR (400 MHz, DMSO) δ 9.54-8.01 (m, 3H), 7.90-7.25 (m, 3H), 5.73-5.46 (m, 1H), 4.90-4.02 (m, 3H), 3.85-3.57 (m, 1H), 1.34-0.98 (m, 3H). MS (ESI): mass calcd. for $C_{17}H_{14}Cl_2N_6O$, 388.1; m/z found, 390.1 $[M+H]^+$.

Example 23: (S)-(2-chloro-3-(trifluoromethyl)phenyl)(6-methyl-3-(pyrazin-2-yl)-5,6-dihydro-[1,2,4]triazolo[4,3-a]pyrazin-7(8H)-yl)methanone

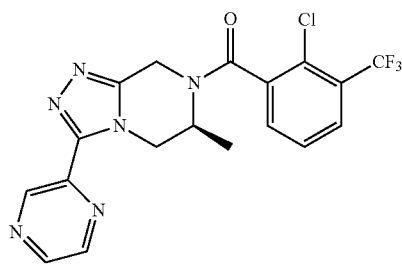 [SMILES: C[C@H]1Cn2c(nnc2-c2cnccn2)CN1C(=O)c1cccc(C(F)(F)F)c1Cl]

(S)-(2-chloro-3-(trifluoromethyl)phenyl)(6-methyl-3-(pyrazin-2-yl)-5,6-dihydro-[1,2,4]triazolo[4,3-a]pyrazin-7(8H)-yl)methanone was generated in an analogous manor to (S)-(2-chloro-3-(trifluoromethyl)phenyl)(3-(4-fluorophenyl)-6-methyl-5,6-dihydro-[1,2,4]triazolo[4,3-a]pyrazin-7(8H)-yl)methanone where in pyrazine-2-carbohydrazide was used in place of 4-fluorobenzohydrazide. 1H NMR (400 MHz, DMSO) δ 9.51-8.68 (m, 3H), 8.22-7.45 (m, 3H), 5.75-5.24 (m, 1H), 4.91-4.05 (m, 3H), 3.92-3.57 (m, 1H), 1.37-0.98 (m, 3H). MS (ESI): mass calcd. for $C_{18}H_{14}ClF_3N_6O$, 422.1; m/z found, 423.1 $[M+H]^+$.

Example 24: (S)-(2-chloro-3-(trifluoromethyl)phenyl)(3-(furan-2-yl)-6-methyl-5,6-dihydro-[1,2,4]triazolo[4,3-a]pyrazin-7(8H)-yl)methanone

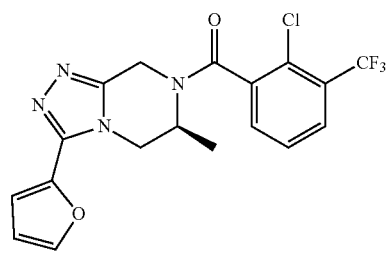 [SMILES: C[C@H]1Cn2c(nnc2-c2ccco2)CN1C(=O)c1cccc(C(F)(F)F)c1Cl]

Intermediate 23A: (S)-tert-butyl 6-methyl-5,6-dihydro-[1,2,4]triazolo[4,3-a]pyrazine-7(8H)-carboxylate

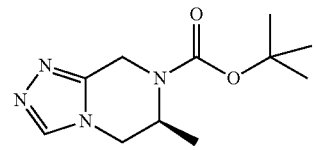 [SMILES: C[C@H]1Cn2cnnc2CN1C(=O)OC(C)(C)C]

Step A: (S)-tert-butyl 6-methyl-5,6-dihydro-[1,2,4]triazolo[4,3-c]pyrazine-7(8H)-carboxylate. (S)-tert-butyl 6-methyl-5,6-dihydro-[1,2,4]triazolo[4,3-a]pyrazine-7(8H)-carboxylate was prepared as described for Intermediate 21D, substituting formic acid hydrazide for 4-fluorobenzohydrazide. MS (ESI) mass calcd. $C_{11}H_{17}BrN_4O_2$, 316.05; m/z found, 317.1 [M+H]⁺.

Intermediate 23B: (S)-tert-butyl 3-bromo-6-methyl-5,6-dihydro-[1,2,4]triazolo[4,3-a]pyrazine-7(8H)-carboxylate

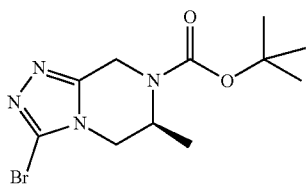 [SMILES: C[C@H]1Cn2c(Br)nnc2CN1C(=O)OC(C)(C)C]

Step B: (S)-tert-butyl 3-bromo-6-methyl-5,6-dihydro-[1,2,4]triazolo[4,3-c]pyrazine-7(8H)-carboxylate. To a solution of (S)-tert-butyl 6-methyl-5,6-dihydro-[1,2,4]triazolo[4,3-a]pyrazine-7(8H)-carboxylate (75 mg, 0.32 mmol) in chloroform (3 mL) was added N-bromosuccinimide (61 mg, 0.35 mmol) and sodium bicarbonate (53 mg, 0.63 mmol). The solution was allowed to stir overnight at rt then saturated sodium bicarbonate (2 mL was added). The layers were separated and the water layer was extracted two times more with methylene chloride. The organic layers were combined, dried over anhydrous MgSO₄, filtered and concentrated. The residue was purified by HPLC (Agilent prep system, Waters) (Bridge C18 5 μm 50×100 mm column, 5-99% MeCN/20 nM NH₄OH over 18 min at 80 mL/min) to provide the product (45 mg, 45%). MS (ESI) mass calcd. $C_{11}H_{17}BrN_4O_2$, 316.05; m/z found, 317.1 [M+H]⁺.

Intermediate 23C: (S)-tert-butyl 3-(furan-2-yl)-6-methyl-5,6-dihydro-[1,2,4]triazolo[4,3-a]pyrazine-7(8H)-carboxylate

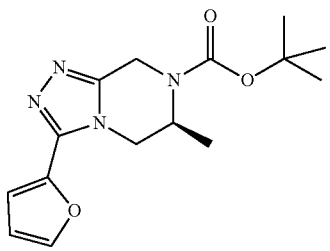 [SMILES: C[C@H]1Cn2c(nnc2-c2ccco2)CN1C(=O)OC(C)(C)C]

Step C: (S)-tert-butyl 3-(furan-2-yl)-6-methyl-5,6-dihydro-[1,2,4]triazolo[4,3-a]pyrazine-7(8H)-carboxylate. To a solution of (S)-tert-butyl 3-bromo-6-methyl-5,6-dihydro-[1,2,4]triazolo[4,3-a]pyrazine-7(8H)-carboxylate (44 mg, 0.14 mmol) in 1,4-dioxane (1 mL) was added 2-furanylboronic acid (47 mg, 0.42 mmol), [1,1'-BIS(DIPHENYLPHOSPHINO)FERROCENE]DICHLOROPALLADIUM(II) (15 mg, 0.021 mmol), 1,1'-BIS(DIPHENYLPHOSPHINO)FERROCENE (5 mg, 0.008 mmol), and potassium phosphate (88 mg, 0.42 mmol). The flask was flushed with nitrogen, sealed and heated to 100° C. overnight. The reaction was allowed to cool and then filtered through celite. The filtrate was concentrated and the residue was purified by silica gel chromatography (30-100% ethyl acetate/hexanes) to provide the product (30 mg, 71%). MS (ESI) mass calcd. $C_{15}H_{20}N_4O_3$, 304.15; m/z found, 305.2 [M+H]⁺.

Example 24: (S)-(2-chloro-3-(trifluoromethyl)phenyl)(3-(furan-2-yl)-6-methyl-5,6-dihydro-[1,2,4]triazolo[4,3-a]pyrazin-7(8H)-yl)methanone

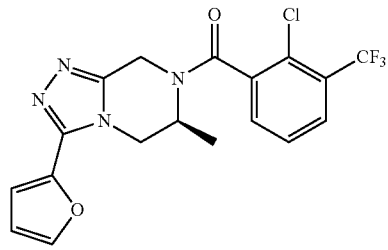 [SMILES: C[C@H]1Cn2c(nnc2-c2ccco2)CN1C(=O)c1cccc(C(F)(F)F)c1Cl]

Step D: (S)-(2-chloro-3-(trifluoromethyl)phenyl)(3-(furan-2-yl)-6-methyl-5,6-dihydro-[1,2,4]triazolo[4,3-c]pyrazin-7(8H)-yl)methanone. To a solution of (S)-tert-butyl 3-(furan-2-yl)-6-methyl-5,6-dihydro-[1,2,4]triazolo[4,3-a]pyrazine-7(8H)-carboxylate (30 mg, 0.1 mmol) in CH₂Cl₂ (1 mL) was added TFA (0.15 mL, 2.0 mmol). The reaction was allowed to stir at rt for 3 h and then evaporated in vacuo. The residue was dissolved in CH₂Cl₂ (5 mL) and cooled to 0° C. after which was added triethylamine (0.092 mL, 0.66 mmol) and (64 mg, 0.26 mmol). The ice bath was removed and warmed to rt followed by the addition of water (5 mL). The layers were separated and the water layer was extracted with CH₂Cl₂ two times more. The organic layers were combined, dried with MgSO₄ and purified by prep HPLC (Agilent prep system, Waters XBridge C18 5 μm 50×100 mm column, 5-99% MeCN/20 nM NH₄OH over 18 min at 80 mL/min) to provide the product (42 mg, 77%). MS (ESI): mass calcd. for $C_{18}H_{14}ClF_3N_4O_2$, 410.1; m/z found, 411.1 [M+H]⁺.

Example 25: (2-chloro-3-(trifluoromethyl)phenyl)(3-(4-fluorophenyl)-8-methyl-5,6-dihydro-[1,2,4]triazolo[4,3-a]pyrazin-7(8H)-yl)methanone

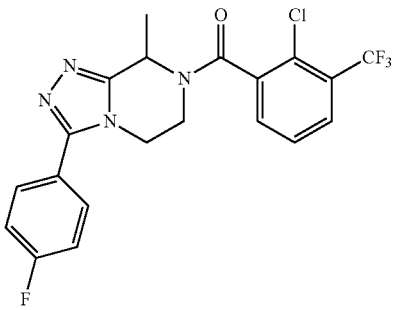 [SMILES: CC1c2nnc(-c3ccc(F)cc3)n2CCN1C(=O)c1cccc(C(F)(F)F)c1Cl]

Example 25, Step a: tert-butyl 2-methyl-3-thioxopiperazine-1-carboxylate. To a heterogeneous mixture of Lawesson's reagent (2.11 g, 5.06 mmol) in toluene (18 mL) was added the product of Example 1, step a (1.01 g, 4.73 mmol).

The mixture was heated at 80° C. for 1 h and then concentrated in vacuo. The residue was dissolved in DCM and filter loaded on SiO$_2$ column eluting with EtOAc/Hex to afford the desired product as an orange solid (1.12 g, 100%). MS (ESI) mass calcd. C$_{10}$H$_{18}$N$_2$O$_2$S, 230.11; m/z found 231.1 [M+H]$^+$. 1H NMR (500 MHz, CDCl$_3$): 8.39 (s, 1H), 5.27-4.84 (m, 1H), 4.30-3.92 (m, 1H), 3.53-3.42 (m, 1H), 3.39-3.30 (m, 1H), 3.30-3.05 (m, 1H), 1.62 (d, J=7.0 Hz, 3H), 1.48 (s, 9H).

Example 25, Step b: tert-butyl 3-(4-fluorophenyl)-8-methyl-5,6-dihydro-[1,2,4]triazolo[4,3-a]pyrazine-7(8H)-carboxylate. The product of Example 25, step a (230 mg, 1.00 mmol) and 4-fluorobenzhydrazide (241 mg, 1.50 mmol) were added to a round bottom flask followed by n-BuOH (4 mL). The mixture was heated at 140° C. for 48 h. The mixture was concentrated in vacuo and taken on to the next step without further purification. MS (ESI) mass calcd. C$_{17}$H$_{21}$FN$_4$O$_2$, 332.16; m/z found 333.2 [M+H]$^+$.

Example 25, Step c: 3-(4-fluorophenyl)-8-methyl-5,6,7,8-tetrahydro-[1,2,4]triazolo[4,3-a]pyrazine. To the product of Example 25, step b (332 mg, 1.00 mmol) in DCM (5 mL) was added TFA (2 mL). After stirring 2 h, the reaction was complete and concentrated in vacuo. The TFA salt was loaded on SiO$_2$ column eluting with 2 M NH$_3$ in MeOH/DCM over 1 h to afford the desired compound as a pale yellow solid. MS (ESI) mass calcd. C$_{12}$H$_{13}$FN$_4$, 232.11; m/z found 233.1 [M+H]$^+$. 1H NMR (500 MHz, CDCl$_3$): 7.71-7.65 (m, 2H), 7.23-7.16 (m, 2H), 4.35-4.29 (m, 1H), 4.08-3.97 (m, 2H), 3.45-3.38 (m, 1H), 3.19-3.11 (m, 1H), 1.69 (d, J=6.7 Hz, 3H).

Example 25, Step d: 7-{[2-Chloro-3-(trifluoromethyl)phenyl]carbonyl}-3-(4-fluorophenyl)-8-methyl-5,6,7,8-tetrahydro[1,2,4]triazolo[4,3-a]pyrazine. To a solution of the product of Example 25, step c (189 mg, 0.82 mmol) in DCM (8 mL) was added TEA (0.14 mL, 0.98 mmol) followed by 2-chloro-3-(trifluoromethyl)benzoyl chloride (208 mg, 0.86 mmol) in one portion. The reaction was stirred overnight and then loaded directly on a SiO$_2$ column eluting with IPA/EtOAc to afford the title compound as a colorless solid (324 mg, 91%). MS (ESI) mass calcd. C$_{20}$H$_{15}$ClF$_4$N$_4$O, 438.09; m/z found 439.1 [M+H]$^+$. 1H NMR (500 MHz, CDCl$_3$) δ 7.86-7.80 (m, 1H), 7.74-7.63 (m, 2H), 7.60-7.40 (m, 2H), 7.26-7.16 (m, 2H), 6.23-6.15 (m, 1H), 5.20-4.97 (m, 1H), 4.34-3.95 (m, 2H), 3.73-3.25 (m, 1H), 1.86-1.53 (m, 3H).

Example 26: (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone

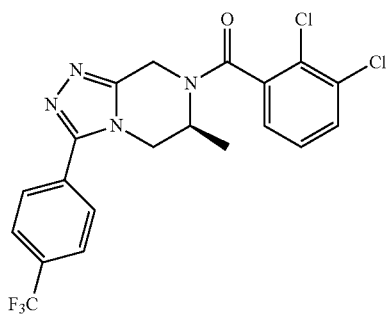 [SMILES: C[C@H]1Cn2c(nnc2-c2ccc(C(F)(F)F)cc2)CN1C(=O)c1cccc(Cl)c1Cl]

Intermediate 26A: (S)-tert-butyl 2-methyl-5-thioxopiperazine-1-carboxylate

To a solution of (S)-tert-butyl 2-methyl-5-oxopiperazine-1-carboxylate (1.2 g, 5.6 mmol) in THF 20 mL) was added Lawesson's Reagent (2.6 g, 6.2 mmol) and the reaction mixture was heated to 80° C. for 1 hour. The reaction mixture was concentrated and purified by flash column chromatography (0-50% EtOAc in hexanes) to provide (S)-tert-butyl 2-methyl-5-thioxopiperazine-1-carboxylate with minor residual impurities. 1H NMR (400 MHz, DMSO) δ 10.64-10.46 (s, 1H), 4.48-4.31 (d, J=18.9 Hz, 1H), 4.31-4.12 (s, 1H), 4.11-3.93 (m, 1H), 3.90-3.74 (m, 1H), 3.20-3.06 (m, 1H), 1.48-1.35 (s, 9H), 1.09-1.02 (d, J=6.6 Hz, 3H).

Intermediate 26B: (S)-tert-butyl 6-methyl-3-(4-(trifluoromethyl)phenyl)-5,6-dihydro-[1,2,4]triazolo[4,3-a]pyrazine-7(8H)-carboxylate To a solution of (S)-tert-butyl 2-methyl-5-thioxopiperazine-1-carboxylate (350 mg, 1.52 mmol) in n-butanol (3 mL) was added 4-(trifluoromethyl)benzohydrazide (479 mg, 2.28 mmol) and the reaction mixture was heated to 140° C. for 48 hours. The reaction mixture was cooled to rt and diluted with methanol (10 ml). BOC-anhydride (0.65 mL, 3.04 mmol) was added and the reaction mixture was stirred for 5 hours. The reaction mixture was diluted with EtOAc, washed with water, dried, concentrated and purified by flash column chromatography (0-100% EtOAc in hexanes) to provide (S)-tert-butyl 6-methyl-3-(4-(trifluoromethyl)phenyl)-5,6-dihydro-[1,2,4]triazolo[4,3-a]pyrazine-7(8H)-carboxylate (375 mg).

Intermediate 26C: (S)-6-methyl-3-(4-(trifluoromethyl)phenyl)-5,6,7,8-tetrahydro-[1,2,4]triazolo[4,3-a]pyrazine (S)-tert-butyl 6-methyl-3-(4-(trifluoromethyl)phenyl)-5,6-dihydro-[1,2,4]triazolo[4,3-a]pyrazine-7(8H)-carboxylate was dissolved in trifluoroacetic acid and stirred at rt for 10 minutes. The reaction mixture was concentrated to provide (S)-6-methyl-3-(4-(trifluoromethyl)phenyl)-5,6,7,8-tetrahydro-[1,2,4]triazolo[4,3-a]pyrazine which was used without further purification.

To a solution of (S)-6-methyl-3-(4-(trifluoromethyl)phenyl)-5,6,7,8-tetrahydro-[1,2,4]triazolo[4,3-a]pyrazine (72 mg, 0.26 mmol) in DCM (5 mL) was added 2,3-dichlorobenzoyl chloride (107 mg, 0.51 mmol) and triethylamine (0.18 mL, 1.28 mmol) and the reaction mixture was stirred for 4 hours at rt. Water was added and the reaction mixture was extracted with DCM. The organic layers were combined, dried, concentrated and purified by hplc. 1H NMR (400 MHz, DMSO) δ 8.18-7.38 (m, 7H), 5.78-5.17 (m, 1H), 4.81-3.81 (m, 4H), 1.25-0.96 (m, 3H). MS (ESI): mass calcd. for C$_{20}$H$_{15}$Cl$_2$F$_3$N$_4$O, 454.1; m/z found, 455.1 [M+H]$^+$.

Example 27: (S)-(2-chloro-3-(trifluoromethyl)phenyl)(6-methyl-3-(4-(trifluoromethyl)phenyl)-5,6-dihydro-[1,2,4]triazolo[4,3-a]pyrazin-7(8H)-yl)methanone

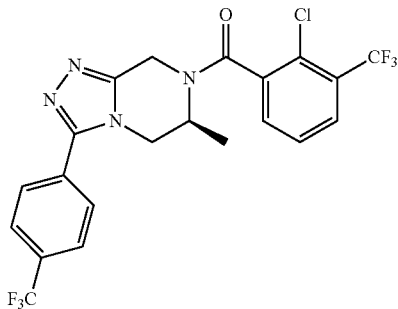 [SMILES: C[C@H]1Cn2c(nnc2-c2ccc(C(F)(F)F)cc2)CN1C(=O)c1cccc(C(F)(F)F)c1Cl]

(S)-(2-chloro-3-(trifluoromethyl)phenyl)(6-methyl-3-(4-(trifluoromethyl)phenyl)-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2-chloro-3-(trifluoromethyl)benzoyl chloride was used in place of 2,3-dichlorobenzoyl chloride. 1H NMR (400 MHz, DMSO) δ 8.12-7.59 (m, 7H), 5.76-5.24 (m, 1H), 4.79-3.80 (m, 4H), 1.36-0.75 (m, 3H). MS (ESI): mass calcd. for $C_{21}H_{15}ClF_6N_4O$, 488.1; m/z found, 489.1 [M+H]$^+$.

Example 28: (S)-(2,3-dichlorophenyl)(3-(3-fluoro-4-(trifluoromethyl)phenyl)-6-methyl-5,6-dihydro-[1,2,4]triazolo[4,3-a]pyrazin-7(8H)-yl)methanone

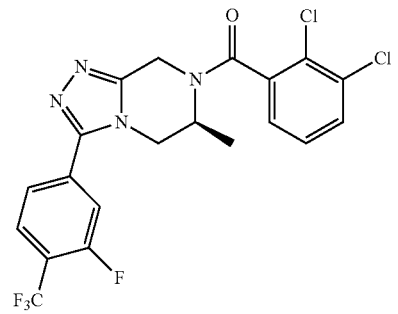 [SMILES: C[C@H]1Cn2c(nnc2-c2ccc(C(F)(F)F)c(F)c2)CN1C(=O)c1cccc(Cl)c1Cl]

(S)-(2,3-dichlorophenyl)(3-(3-fluoro-4-(trifluoromethyl)phenyl)-6-methyl-5,6-dihydro-[1,2,4]triazolo[4,3-a]pyrazin-7(8H)-yl)methanone was generated in analogous fashion (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 3-fluoro-4-(trifluoromethyl)benzohydrazide was used in place of 4-(trifluoromethyl)benzohydrazide. 1H NMR (400 MHz, DMSO) δ 8.07-7.37 (m, 6H), 5.74-5.19 (m, 1H), 4.85-3.87 (m, 4H), 1.26-0.96 (m, 3H). MS (ESI): mass calcd. for $C_{20}H_{14}Cl_2F_4N_4O$, 472.0; m/z found, 473.1 [M+H]$^+$.

Example 29: (S)-(2-chloro-3-(trifluoromethyl)phenyl)(3-(3-fluoro-4-(trifluoromethyl)phenyl)-6-methyl-5,6-dihydro-[1,2,4]triazolo[4,3-a]pyrazin-7(8H)-yl)methanone

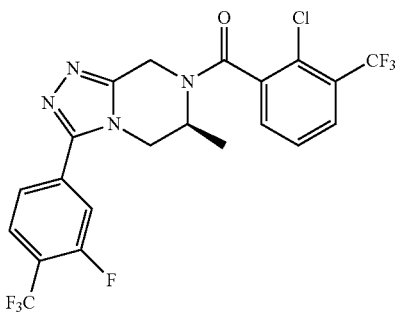 [SMILES: C[C@H]1Cn2c(nnc2-c2ccc(C(F)(F)F)c(F)c2)CN1C(=O)c1cccc(C(F)(F)F)c1Cl]

(S)-(2-chloro-3-(trifluoromethyl)phenyl)(3-(3-fluoro-4-(trifluoromethyl)phenyl)-6-methyl-5,6-dihydro-[1,2,4]triazolo[4,3-a]pyrazin-7(8H)-yl)methanone was generated in an analogous fashion to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 3-fluoro-4-(trifluoromethyl)benzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (400 MHz, DMSO) δ 8.15-7.62 (m, 6H), 5.73-5.26 (m, 1H), 4.83-3.86 (m, 4H), 1.30-0.97 (m, 3H). MS (ESI): mass calcd. for $C_{21}H_{14}ClF_7N_4O$, 506.1; m/z found, 507.1 [M+H]$^+$.

Example 30: (S)-(2-chloro-3-(trifluoromethyl)phenyl)(6-methyl-3-(3,4,5-trifluorophenyl)-5,6-dihydro-[1,2,4]triazolo[4,3-a]pyrazin-7(8H)-yl)methanone

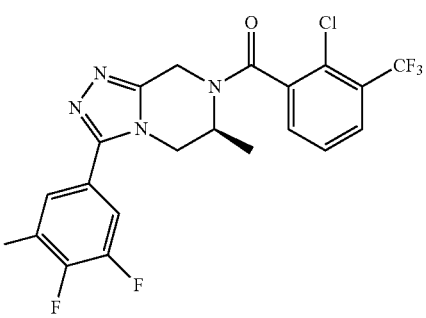

(S)-(2-chloro-3-(trifluoromethyl)phenyl)(6-methyl-3-(3,4,5-trifluorophenyl)-5,6-dihydro-[1,2,4]triazolo[4,3-a]pyrazin-7(8H)-yl)methanone was generated in analogous fashion to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 3,4,5-trifluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (400 MHz, DMSO) δ 8.08-7.59 (m, 5H), 5.67-5.21 (m, 1H), 4.79-3.84 (m, 4H), 1.23-0.94 (m, 3H). MS (ESI): mass calcd. for $C_{20}H_{13}ClF_6N_4O$, 474.1; m/z found, 475.1 [M+H]$^+$.

Example 31: (S)-(2,3-dichlorophenyl)(6-methyl-3-(pyridin-2-yl)-5,6-dihydro-[1,2,4]triazolo[4,3-a]pyrazin-7(8H)-yl)methanone

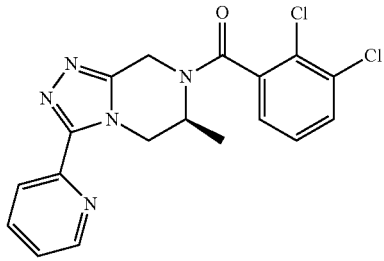

(S)-(2,3-dichlorophenyl)(6-methyl-3-(pyridin-2-yl)-5,6-dihydro-[1,2,4]triazolo[4,3-a]pyrazin-7(8H)-yl)methanone was generated in an analogous manor to that describe for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in picolinohydrazide was used in place of 4-(trifluoromethyl)benzohydrazide. 1H NMR (400 MHz, DMSO) δ 8.83-7.41 (m, 7H), 5.68-5.24 (m, 1H), 5.03-3.91 (m, 4H), 1.43-0.96 (m, 3H). MS (ESI): mass calcd. for $C_{18}H_{15}Cl_2N_5O$, 387.1; m/z found, 388.1[M+H]$^+$.

Example 33: (S)-(2,3-dichlorophenyl)(3-(4-fluorophenyl)-6-methyl-5,6-dihydro-[1,2,4]triazolo[4,3-a]pyrazin-7(8H)-yl)methanone

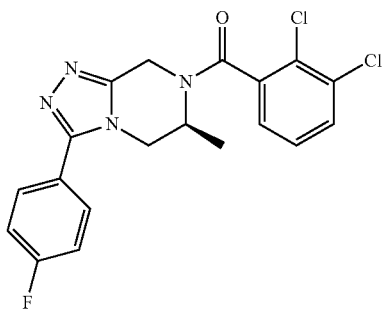 [SMILES: C[C@H]1Cn2c(nnc2-c2ccc(F)cc2)CN1C(=O)c1cccc(Cl)c1Cl]

Example 34: (2,3-dichlorophenyl)(5-methyl-3-(pyridin-2-yl)-5,6-dihydro-[1,2,4]triazolo[4,3-a]pyrazin-7(8H)-yl)methanone

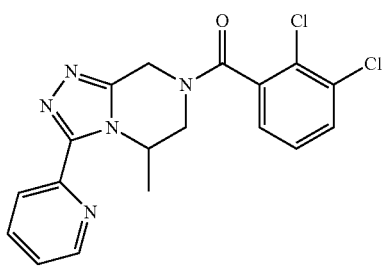 [SMILES: CC1CN(C(=O)c2cccc(Cl)c2Cl)Cc2nnc(-c3ccccn3)n21]

Example 35: (2-chloro-3-(trifluoromethyl)phenyl)(8-methyl-3-(4-(trifluoromethyl)phenyl)-5,6-dihydro-[1,2,4]triazolo[4,3-a]pyrazin-7(8H)-yl)methanone

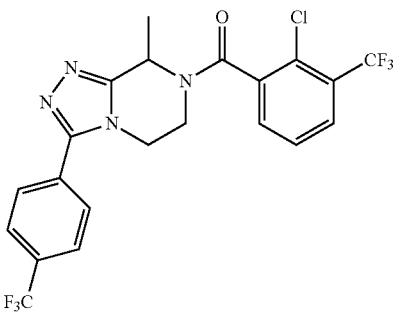 [SMILES: CC1c2nnc(-c3ccc(C(F)(F)F)cc3)n2CCN1C(=O)c1cccc(C(F)(F)F)c1Cl]

The title compound was prepared in a manner analogous to Example 25 substituting 4-(trifluoromethyl)benzhydrazide for 4-fluorobenzhydrazide in Example 25, step b. MS (ESI) mass calcd. $C_{21}H_{15}ClF_6N_4O$, 488.08; m/z found 489.1 [M+H]$^+$. 1H NMR (500 MHz, CDCl3): 7.89-7.74 (m, 5H), 7.60-7.41 (m, 2H), 6.24-6.18 (m, 1H), 5.21-5.00 (m, 1H), 4.36-4.16 (m, 1H), 4.08-4.00 (m, 1H), 3.73-3.64 (m, 1H), 3.56-3.28 (m, 1H), 1.86-1.61 (m, 3H).

Example 36: (2-chloro-3-(trifluoromethyl)phenyl)(8-methyl-3-(pyrazin-2-yl)-5,6-dihydro-[1,2,4]triazolo[4,3-a]pyrazin-7(8H)-yl)methanone

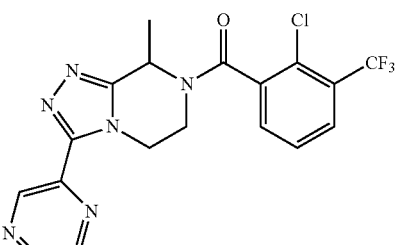

The title compound was prepared in a manner analogous to Example 25 substituting pyrazine-2-carbohydrazide for 4-fluorobenzhydrazide in Example 25, step b. MS (ESI) mass calcd. $C_{18}H_{14}ClF_3N_6O$, 422.09; m/z found 423.1 [M+H]$^+$. 1H NMR (500 MHz, CDCl3): 9.63-9.55 (m, 1H), 8.68-8.48 (m, 2H), 7.85-7.77 (m, 1H), 7.60-7.36 (m, 2H), 6.27-6.21 (m, 1H), 5.21-4.83 (m, 2H), 4.43-4.09 (m, 1H), 3.78-3.35 (m, 1H), 1.86-1.57 (m, 3H).

Example 37: (2-chloro-3-(trifluoromethyl)phenyl)
(3-(4-chlorophenyl)-8-methyl-5,6-dihydro-[1,2,4]
triazolo[4,3-a]pyrazin-7(8H)-yl)methanone

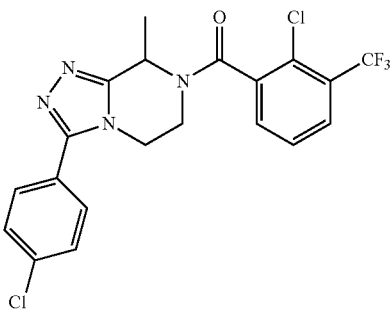

The title compound was prepared in a manner analogous to Example 25 substituting 4-chlorobenzhydrazide for 4-fluorobenzhydrazide in Example 25, step b. MS (ESI) mass calcd. $C_{20}H_{15}Cl_2F_3N_4O$, 454.06; m/z found 455.1 [M+H]$^+$. 1H NMR (500 MHz, CDCl$_3$): 7.86-7.81 (m, 1H), 7.69-7.45 (m, 6H), 6.21-6.16 (m, 1H), 5.19-4.98 (m, 1H), 4.31-3.97 (m, 2H), 3.72-3.26 (m, 1H), 1.85-1.60 (m, 3H).

Example 38: (S)-(2,3-dichlorophenyl)(3-(2-fluorophenyl)-6-methyl-5,6-dihydro-[1,2,4]triazolo[4,3-a]pyrazin-7(8H)-yl)methanone

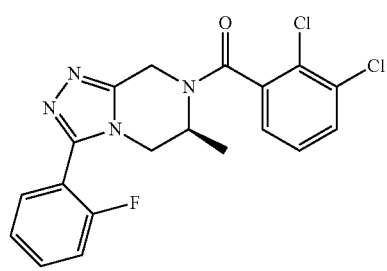 [SMILES: C[C@H]1Cn2c(nnc2-c2ccccc2F)CN1C(=O)c1cccc(Cl)c1Cl]

(S)-(2,3-dichlorophenyl)(3-(2-fluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2-fluorobenzohydrazide was used in place of 4-(trifluoromethyl)benzohydrazide. 1H NMR (400 MHz, DMSO) δ 7.90-7.32 (m, 7H), 5.65-5.20 (m, 1H), 4.85-3.62 (m, 4H), 1.30-0.91 (m, 3H). MS (ESI): mass calcd. for $C_{19}H_{15}Cl_2FN_4O$, 404.1; m/z found, 405.1 [M+H]$^+$.

Example 39: (S)-(2-chloro-3-(trifluoromethyl)phenyl)(3-(2-fluorophenyl)-6-methyl-5,6-dihydro-[1,2,4]triazolo[4,3-a]pyrazin-7(8H)-yl)methanone

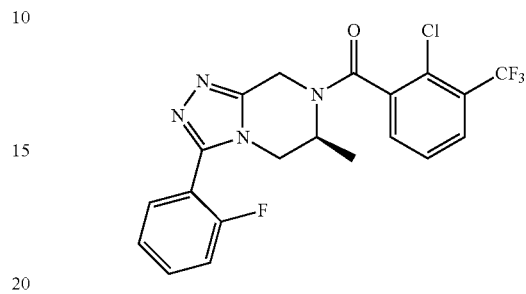

(S)-(2-chloro-3-(trifluoromethyl)phenyl)(3-(2-fluorophenyl)-6-methyl-5,6-dihydro-[1,2,4]triazolo[4,3-a]pyrazin-7(8H)-yl)methanone was generated in an analogous manor to (S(S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2-fluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (400 MHz, DMSO) δ 8.10-7.25 (m, 7H), 5.68-5.19 (m, 1H), 4.86-3.58 (m, 4H), 1.28-0.86 (m, 3H). MS (ESI): mass calcd. for $C_{20}H_{15}ClF_4N_4O$, 438.1; m/z found, 439.1 [M+H]$^+$.

Example 40: (S)-(2,3-dichloro-4-fluorophenyl)(3-(2-fluorophenyl)-6-methyl-5,6-dihydro-[1,2,4]triazolo[4,3-a]pyrazin-7(8H)-yl)methanone

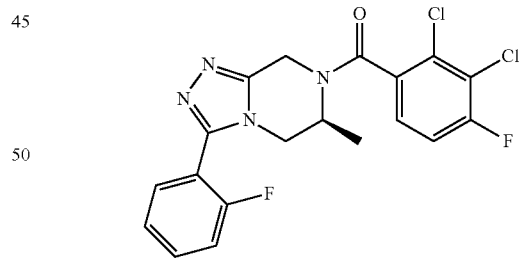

(S)-(2,3-dichloro-4-fluorophenyl)(3-(2-fluorophenyl)-6-methyl-5,6-dihydro-[1,2,4]triazolo[4,3-a]pyrazin-7(8H)-yl)methanone was generated in an analogous fashion to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2-fluorobenzohydrazide was used in place of 4-(trifluoromethyl)benzohydrazide and 2,3-dichloro-4-fluorobenzoyl chloride was used in place of 2,3-dichlorobenzoyl chloride. 1H NMR (400 MHz, DMSO) δ 7.98-7.28 (m, 7H), 5.69-5.01 (m, 1H), 4.78-3.54 (m, 4H), 1.27-0.90 (m, 3H). MS (ESI): mass calcd. for $C_{19}H_{14}Cl_2F_2N_4O$, 422.1; m/z found, 423.1 [M+H]$^+$.

Example 41: (S)-(2,3-dichlorophenyl)(3-(3-fluorophenyl)-6-methyl-5,6-dihydro-[1,2,4]triazolo[4,3-a]pyrazin-7(8H)-yl)methanone

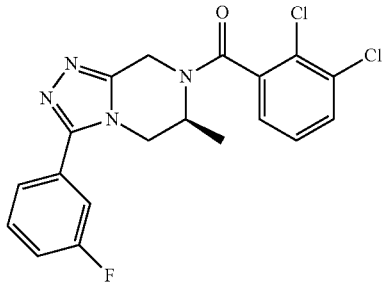 [SMILES: C[C@H]1Cn2c(nnc2-c2cccc(F)c2)CN1C(=O)c1cccc(Cl)c1Cl]

(S)-(2,3-dichlorophenyl)(3-(3-fluorophenyl)-6-methyl-5,6-dihydro-[1,2,4]triazolo[4,3-a]pyrazin-7(8H)-yl)methanone was generated in an analogous manor to (S)-(2-chloro-3-(trifluoromethyl)phenyl)(6-methyl-3-(4-(trifluoromethyl)phenyl)-5,6-dihydro-[1,2,4]triazolo[4,3-a]pyrazin-7(8H)-yl)methanone wherein 3-fluorobenzohydrazide was used in place of 4-(trifluoromethyl)benzohydrazide. 1H NMR (500 MHz, DMSO) δ 7.94-7.28 (m, 7H), 5.74-5.19 (m, 1H), 4.82-3.76 (m, 4H), 1.30-0.84 (m, 3H). MS (ESI): mass calcd. for $C_{19}H_{15}Cl_2FN_4O$, 404.1; m/z found, 405.1 [M+H]$^+$.

Example 42: (S)-(2-chloro-3-(trifluoromethyl)phenyl)(3-(3-fluorophenyl)-6-methyl-5,6-dihydro-[1,2,4]triazolo[4,3-a]pyrazin-7(8H)-yl)methanone

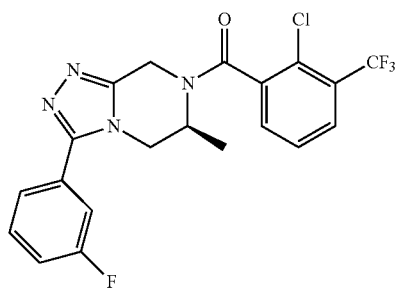 [SMILES: C[C@H]1Cn2c(nnc2-c2cccc(F)c2)CN1C(=O)c1cccc(C(F)(F)F)c1Cl]

(S)-(2-chloro-3-(trifluoromethyl)phenyl)(3-(3-fluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 3-fluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (400 MHz, DMSO) δ 8.14-7.28 (m, 7H), 5.73-5.19 (m, 1H), 4.90-3.80 (m, 4H), 1.42-0.90 (m, 3H). MS (ESI): mass calcd. for $C_{20}H_{15}ClF_4N_4O$, 438.1; m/z found, 439.1 [M+H]$^+$.

Example 43: (S)-(2,3-dichloro-4-fluorophenyl)(3-(3-fluorophenyl)-6-methyl-5,6-dihydro-[1,2,4]triazolo[4,3-a]pyrazin-7(8H)-yl)methanone

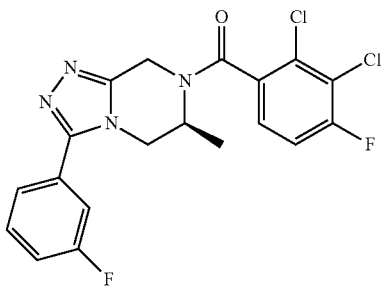 [SMILES: C[C@H]1Cn2c(nnc2-c2cccc(F)c2)CN1C(=O)c1ccc(F)c(Cl)c1Cl]

(S)-(2,3-dichloro-4-fluorophenyl)(3-(3-fluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 3-fluorobenzohydrazide was used in place of 4-(trifluoromethyl)benzohydrazide. 1H NMR (400 MHz, DMSO) δ 7.96-7.23 (m, 6H), 5.72-5.18 (m, 1H), 4.78-3.75 (m, 4H), 1.30-0.89 (m, 3H). MS (ESI): mass calcd. for $C_{19}H_{14}Cl_2F_2N_4O$, 422.1; m/z found, 423.1 [M+H]$^+$.

Example 44: (S)-(2,3-dichlorophenyl)(3-(2,3-difluorophenyl)-6-methyl-5,6-dihydro-[1,2,4]triazolo[4,3-a]pyrazin-7(8H)-yl)methanone

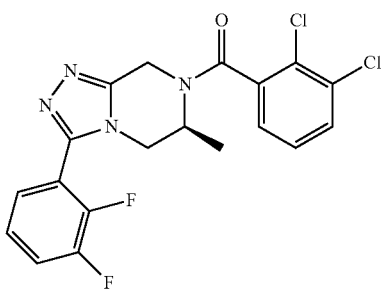 [SMILES: C[C@H]1Cn2c(nnc2-c2cccc(F)c2F)CN1C(=O)c1cccc(Cl)c1Cl]

(S)-(2,3-dichlorophenyl)(3-(2,3-difluorophenyl)-6-methyl-5,6-dihydro-[1,2,4]triazolo[4,3-a]pyrazin-7(8H)-yl)methanone was generated in a manor analogous to that described for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2,3-difluorobenzohydrazide was used in place of 4-(trifluoromethyl)benzohydrazide. 1H NMR (600 MHz, DMSO) δ 7.85-7.34 (m, 6H), 5.71-5.20 (m, 1H), 4.83-3.66 (m, 4H), 1.30-0.90 (m, 3H). MS (ESI): mass calcd. for $C_{19}H_{14}Cl_2F_2N_4O$, 422.1; m/z found, 423.1 [M+H]$^+$.

Example 45: (S)-(2-chloro-3-(trifluoromethyl)phenyl)(3-(2,3-difluorophenyl)-6-methyl-5,6-dihydro-[1,2,4]triazolo[4,3-a]pyrazin-7(8H)-yl)methanone

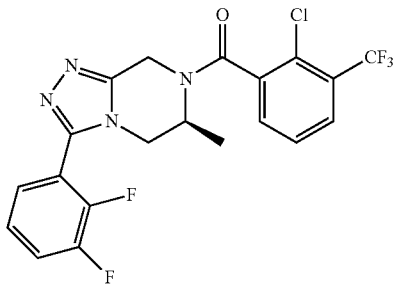 [SMILES: C[C@H]1Cn2c(nnc2-c2cccc(F)c2F)CN1C(=O)c1cccc(C(F)(F)F)c1Cl]

(S)-(2-chloro-3-(trifluoromethyl)phenyl)(3-(2,3-difluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 2,3-difluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (600 MHz, DMSO) δ 8.13-7.20 (m, 6H), 5.73-5.18 (m, 1H), 4.85-3.53 (m, 4H), 1.35-0.87 (m, 3H). MS (ESI): mass calcd. for $C_{20}H_{14}ClF_5N_4O$, 456.1; m/z found, 457.1 [M+H]$^+$.

Example 46: (S)-(2,3-dichloro-4-fluorophenyl)(3-(2,3-difluorophenyl)-6-methyl-5,6-dihydro-[1,2,4]triazolo[4,3-a]pyrazin-7(8H)-yl)methanone

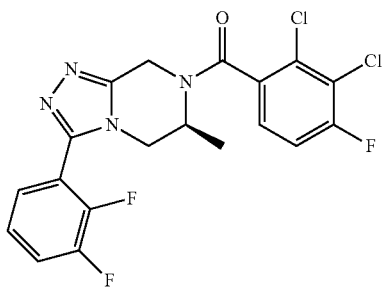 [SMILES: C[C@H]1Cn2c(nnc2-c2cccc(F)c2F)CN1C(=O)c1ccc(F)c(Cl)c1Cl]

(S)-(2,3-dichloro-4-fluorophenyl)(3-(2,3-difluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2,3-difluorobenzohydrazide was used in place of 4-(trifluoromethyl)benzohydrazide and 2,3-dichloro-4-fluorobenzoyl chloride was used in place of 2,3-dichlorobenzoyl chloride. 1H NMR (600 MHz, DMSO) δ 7.81-7.36 (m, 5H), 5.70-5.16 (m, 1H), 4.76-3.49 (m, 4H), 1.25-0.88 (m, 3H). MS (ESI): mass calcd. for $C_{19}H_{13}Cl_2F_3N_4O$, 440.0; m/z found, 441.1 [M+H]$^+$.

Example 47: (S)-(2,3-dichlorophenyl)(3-(3,4-difluorophenyl)-6-methyl-5,6-dihydro-[1,2,4]triazolo[4,3-a]pyrazin-7(8H)-yl)methanone

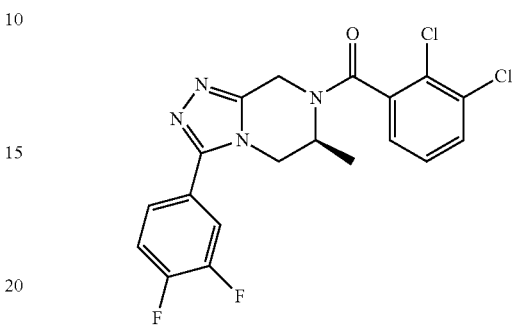

(S)-(2,3-dichlorophenyl)(3-(3,4-difluorophenyl)-6-methyl-5,6-dihydro-[1,2,4]triazolo[4,3-a]pyrazin-7(8H)-yl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 3,4-difluorobenzohydrazide was used in place of 4-(trifluoromethyl)benzohydrazide. 1H NMR (600 MHz, DMSO) δ 7.98-7.33 (m, 6H), 5.72-5.23 (m, 1H), 4.78-3.73 (m, 4H), 1.29-0.94 (m, 3H). MS (ESI): mass calcd. for $C_{19}H_{14}Cl_2F_2N_4O$, 422.1; m/z found, 423.1 [M+H]$^+$.

Example 48: (S)-(2-chloro-3-(trifluoromethyl)phenyl)(3-(3,4-difluorophenyl)-6-methyl-5,6-dihydro-[1,2,4]triazolo[4,3-a]pyrazin-7(8H)-yl)methanone

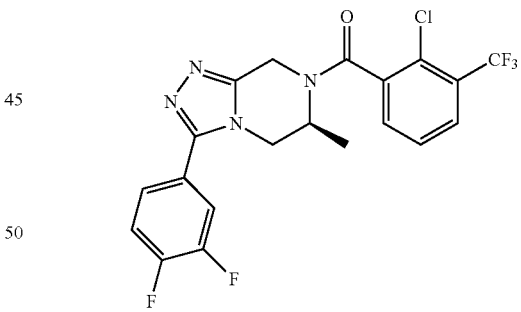

(S)-(2-chloro-3-(trifluoromethyl)phenyl)(3-(3,4-difluorophenyl)-6-methyl-5,6-dihydro-[1,2,4]triazolo[4,3-a]pyrazin-7(8H)-yl)methanone was generated in an analogous manor to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 3,4-difluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (600 MHz, DMSO) δ 8.11-7.48 (m, 6H), 5.75-5.23 (m, 1H), 4.80-3.81 (m, 4H), 1.29-0.96 (m, 3H). MS (ESI): mass calcd. for $C_{20}H_{14}ClF_5N_4O$, 456.1; m/z found, 457.1 [M+H]$^+$.

Example 49: (S)-(2,3-dichloro-4-fluorophenyl)(3-(3,4-difluorophenyl)-6-methyl-5,6-dihydro-[1,2,4]triazolo[4,3-a]pyrazin-7(8H)-yl)methanone

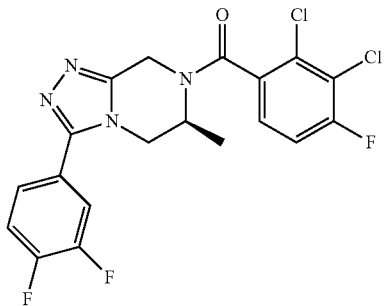 [SMILES: C[C@H]1Cn2c(nnc2-c2ccc(F)c(F)c2)CN1C(=O)c1ccc(F)c(Cl)c1Cl]

(S)-(2,3-dichloro-4-fluorophenyl)(3-(3,4-difluorophenyl)-6-methyl-5,6-dihydro-[1,2,4]triazolo[4,3-a]pyrazin-7(8H)-yl)methanone was generated in a manor analogous to that described for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 3,4-difluorobenzohydrazide was used in place of 4-(trifluoromethyl)benzohydrazide and 2,3-dichloro-4-fluorobenzoyl chloride was used in place of 2,3-dichlorobenzoyl chloride. 1H NMR (600 MHz, DMSO) δ 8.05-7.39 (m, 5H), 5.73-5.18 (m, 1H), 4.80-3.77 (m, 4H), 1.38-0.91 (m, 3H). MS (ESI): mass calcd. for $C_{19}H_{13}Cl_2F_3N_4O$, 440.0; m/z found, 441.1 $[M+H]^+$.

Example 50: (S)-(2,3-dichlorophenyl)(3-(2,4-difluorophenyl)-6-methyl-5,6-dihydro-[1,2,4]triazolo[4,3-a]pyrazin-7(8H)-yl)methanone

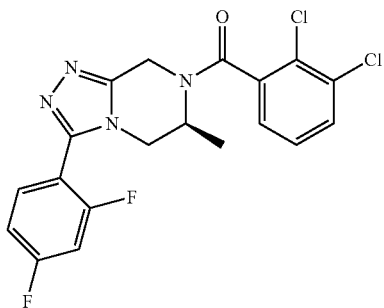 [SMILES: C[C@H]1Cn2c(nnc2-c2ccc(F)cc2F)CN1C(=O)c1cccc(Cl)c1Cl]

(S)-(2,3-dichlorophenyl)(3-(2,4-difluorophenyl)-6-methyl-5,6-dihydro-[1,2,4]triazolo[4,3-a]pyrazin-7(8H)-yl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in 2,4-difluorobenzohydrazide was used in place of 4-(trifluoromethyl)benzohydrazide. 1H NMR (600 MHz, DMSO) δ 7.88-7.26 (m, 6H), 5.71-5.17 (m, 1H), 4.79-3.53 (m, 4H), 1.35-0.87 (m, 3H). MS (ESI): mass calcd. for $C_{19}H_{14}Cl_2F_2N_4O$, 422.1; m/z found, 423.1 $[M+H]^+$.

Example 51: (S)-(2-chloro-3-(trifluoromethyl)phenyl)(3-(2,4-difluorophenyl)-6-methyl-5,6-dihydro-[1,2,4]triazolo[4,3-a]pyrazin-7(8H)-yl)methanone

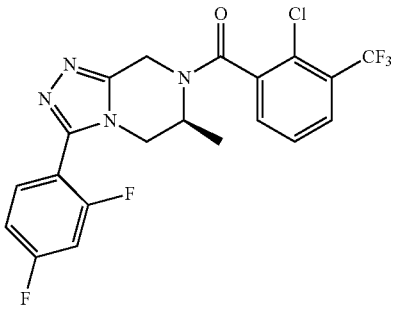 [SMILES: C[C@H]1Cn2c(nnc2-c2ccc(F)cc2F)CN1C(=O)c1cccc(C(F)(F)F)c1Cl]

(S)-(2-chloro-3-(trifluoromethyl)phenyl)(3-(2,4-difluorophenyl)-6-methyl-5,6-dihydro-[1,2,4]triazolo[4,3-a]pyrazin-7(8H)-yl)methanone was generated in a manor analogous to that described for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 2,4-difluorobenzohydrazide was used in place of 4-(trifluoromethyl)benzohydrazide and 2-chloro-3-(trifluoromethyl)benzoyl chloride was used in place of 2,3-dichlorobenzoyl chloride. 1H NMR (600 MHz, DMSO) δ 8.12-7.23 (m, 6H), 5.68-5.20 (m, 1H), 4.81-3.58 (m, 4H), 1.27-0.89 (m, 3H). MS (ESI): mass calcd. for $C_{20}H_{14}ClF_5N_4O$, 456.1; m/z found, 457.1 $[M+H]^+$.

Example 52: (S)-(2,3-dichloro-4-fluorophenyl)(3-(2,4-difluorophenyl)-6-methyl-5,6-dihydro-[1,2,4]triazolo[4,3-a]pyrazin-7(8H)-yl)methanone

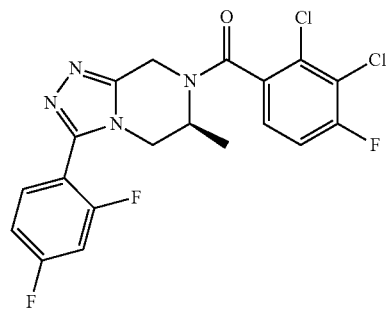 [SMILES: C[C@H]1Cn2c(nnc2-c2ccc(F)cc2F)CN1C(=O)c1ccc(F)c(Cl)c1Cl]

(S)-(2-chloro-4-fluoro-3-(trifluoromethyl)phenyl)(3-(2,4-difluorophenyl)-6-methyl-5,6-dihydro-[1,2,4]triazolo[4,3-a]pyrazin-7(8H)-yl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein 2,4-difluorobenzohydrazide was used in place of 4-(trifluoromethyl)benzohydrazide and 2,3-dichloro-4-fluorobenzoyl chloride was used in place of 2,3-dichlorobenzoyl chloride. 1H NMR (600 MHz, DMSO) δ 7.88-7.22 (m, 5H), 5.66-5.19 (m, 1H), 4.74-3.60 (m, 4H), 1.26-0.84 (m, 3H). MS (ESI): mass calcd. for $C_{19}H_{13}Cl_2F_3N_4O$, 440.0; m/z found, 441.1 $[M+H]^+$.

Example 53: (2-chloro-3-(trifluoromethyl)phenyl) (3-methyl-8-phenyl-5,6-dihydro-[1,2,4]triazolo[4,3-a]pyrazin-7(8H)-yl)methanone

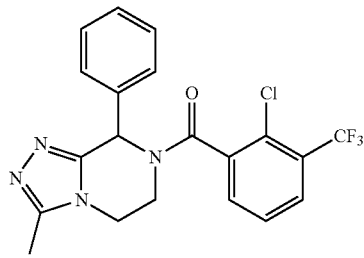 [SMILES: Cc1nnc2n1CCN(C(=O)c1cccc(C(F)(F)F)c1Cl)C2c1ccccc1]

Intermediate 53A: tert-butyl (2-(2-bromo-2-phenylacetamido)ethyl)carbamate

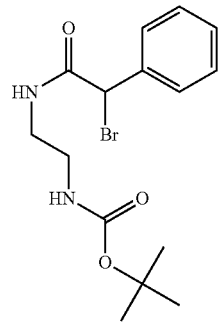 [SMILES: CC(C)(C)OC(=O)NCCNC(=O)C(Br)c1ccccc1]

Step A: tert-butyl (2-(2-bromo-2-phenylacetamido)ethyl) carbamate. A solution of tert-butyl N-(2-aminoethyl)carbamate (10 g, 59.29 mmol) in 40 mL of DCM was cooled to −78° C. Triethylamine (16.48 mL, 118.59 mmol) and 2-bromo-2-phenylacetyl chloride (13.85 g, 59.29 mmol) were subsequently added and the reaction mixture was stirred for 20 minutes then warmed to 0° C. and stirred for 1 hour. The reaction mixture was quenched with water and then extracted three times with DCM. The combined organic layers were washed with brine, dried with MgSO$_4$ and concentrated under reduced pressure. The resulting residue was purified via silica gel chromatography (0-50% ethyl acetate/hexanes) to provide the desired product (15.09 g, 71%) as a white solid. $^1$H NMR (500 MHz, CDCl$_3$) δ 7.51-7.28 (m, 5H), 5.43-5.31 (m, 1H), 4.89 (s, 2H), 3.58-3.16 (m, 4H), 1.56-1.32 (m, 9H). MS (ESI) mass calcd. C$_{15}$H$_{21}$BrN$_2$O$_3$, 357.2; m/z found, 358.2 [M+H]$^+$.

Intermediate 53B: N-(2-aminoethyl)-2-bromo-2-phenylacetamide

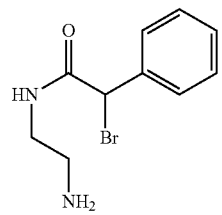 [SMILES: NCCNC(=O)C(Br)c1ccccc1]

Step B: N-(2-aminoethyl)-2-bromo-2-phenylacetamide. To a solution of tert-butyl (2-(2-bromo-2-phenylacetamido) ethyl)carbamate (7.8 g, 21.75 mmol) in 30 mL of DCM was added Trifluoroacetic acid (16.6 mL, 217.49 mmol). The resulting reaction mixture was allowed to stir at room temperature overnight. The reaction mixture was concentrated into a brown residue under reduced pressure and then washed with conc. NaHCO$_3$ solution and extracted three times with DCM. The combined organic layers were dried using MgSO$_4$, filtered and concentrated to provide the desired product (10.54 g, 99%). MS (ESI) mass calcd. C$_{10}$H$_{13}$BrN$_2$O, 257.2; m/z found, 258.2 [M+H]$^+$.

Intermediate 53C: tert-butyl 3-oxo-2-phenylpiperazine-1-carboxylate

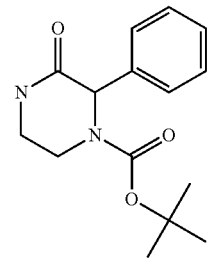 [SMILES: CC(C)(C)OC(=O)N1CCNC(=O)C1c1ccccc1]

Step C: tert-butyl 3-oxo-2-phenylpiperazine-1-carboxylate. To a solution of N-(2-aminoethyl)-2-bromo-2-phenylacetamide (19.28 g, 43.74 mmol) in 430 mL of THF was added anhydrous K$_2$CO$_3$ (60.46 g, 437.46 mmol). The resulting reaction mixture was refluxed at 65° C. overnight. Di-tert-butyldicarbonate (19.28 g, 87.49 mmol) was subsequently added and the reaction mixture was refluxed at 65° C. for an additional 5 hours. The resulting reaction mixture was cooled to room temperature and diluted with ethyl acetate then washed with water. The organic layer was partitioned, dried with MgSO$_4$, filtered and concentrated into a residue. The resulting residue was purified via silica gel chromatography (0-30% Ethyl acetate/hexanes) to provide the desired product (9.54 g, 79%) as a white solid. $^1$H NMR (500 MHz, CDCl$_3$) δ 7.42-7.27 (m, 5H), 6.02-5.71 (m, 1H), 4.15-4.06 (m, 1H), 3.80-3.69 (m, 1H), 3.69-3.61 (m, 1H), 3.42-3.30 (m, 1H), 1.51 (s, 9H). MS (ESI) mass calcd. C$_{15}$H$_{20}$N$_2$O$_3$, 276.3; m/z found, 277.2 [M+H]$^+$.

Intermediate 53D: tert-butyl 2-phenyl-3-thioxopiperazine-1-carboxylate

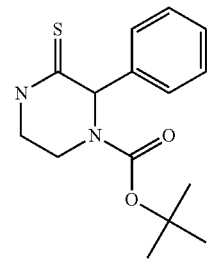

Step D: tert-butyl 2-phenyl-3-thioxopiperazine-1-carboxylate. To a mixture of Lawesson's reagent (4.15 g, 9.95 mmol) in 125 mL of toluene was added tert-butyl 3-oxo-2-phenylpiperazine-1-carboxylate (2.5 g, 9.05 mmol) in a 5 mL solution of toluene. The resulting reaction mixture was heated at 110° C. for 3 hours in a sealed tube. The reaction was worked up with 10% NaOH solution and extracted three times with ethyl acetate. The combined organic layers were dried with MgSO$_4$, filtered and concentrated into a residue. The resulting residue was purified via silica gel chromatography (0-50% ethyl acetate/hexanes) to provide the desired product (613.8 mg, 23%) as a crystalline orange solid. $^1$H NMR (500 MHz, CDCl$_3$) δ 9.67 (s, 1H), 7.51-7.41 (m, 2H), 7.37-7.27 (m, 3H), 6.13 (s, 1H), 4.08-3.77 (m, 1H), 3.53-3.38 (m, 1H), 3.38-3.26 (m, 2H), 1.50 (s, 9H). MS (ESI) mass calcd. C$_{15}$H$_{20}$N$_2$SO$_2$, 292.4; m/z found, 293.2 [M+H]$^+$.

Intermediate 53E: tert-butyl 3-(methylthio)-2-phenyl-5,6-dihydropyrazine-1(2H)-carboxylate

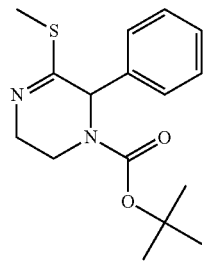 [SMILES: CSC1=NCCN(C(=O)OC(C)(C)C)C1c1ccccc1]

Step E: tert-butyl 3-(methylthio)-2-phenyl-5,6-dihydropyrazine-1(2H)-carboxylate. To a stirred solution of tert-butyl 2-phenyl-3-thioxopiperazine-1-carboxylate (390 mg, 1.334 mmol)) in 3 ml of acetonitrile was added iodomethane (227 mg, 1.601 mmol). The resulting reaction mixture was stirred at room temperature overnight and then concentrated under reduced pressure to provide the desired product (407 mg, 99%). $^1$H NMR (500 MHz, CDCl$_3$) δ 7.51-7.41 (m, 3H), 7.40-7.31 (m, 2H), 6.17 (s, 1H), 4.25-4.08 (m, 2H), 4.06-3.90 (m, 1H), 3.50-3.37 (m, 1H), 3.08 (s, 3H), 1.48 (s, 9H). MS (ESI) mass calcd. C$_{16}$H$_{22}$N$_2$SO$_2$, 306.4; m/z found, 307.2 [M+H]$^+$.

Intermediate 53F: tert-butyl 3-methyl-8-phenyl-5,6-dihydro-[1,2,4]triazolo[4,3-a]pyrazine-7(8H)-carboxylate

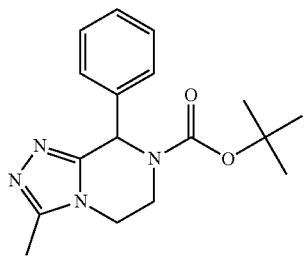 [SMILES: Cc1nnc2n1CCN(C(=O)OC(C)(C)C)C2c1ccccc1]

Step F: tert-butyl 3-methyl-8-phenyl-5,6-dihydro-[1,2,4]triazolo[4,3-a]pyrazine-7(8H)-carboxylate. To a round-bottom flask was added tert-butyl 3-(methylthio)-2-phenyl-5,6-dihydropyrazine-1(2H)-carboxylate (606 mg, 1.978 mmol), acetic hydrazide (1.48 g, 19.76 mmol) followed by 10 mL of n-butanol. The resulting reaction mixture was heated to 155° and stirred for 3 hours. The reaction mixture was cooled to room temperature and di-tert-butyl dicarbonate (436 mg, 1.978 mmol) was added. The reaction mixture was subsequently stirred for 1 hour at room temperature then isolated and concentrated down into a brown residue which was purified via silica gel chromatography (0-10% 2M NH$_3$/MeOH in DCM) to produce the desired product (390 mg, 63%). $^1$H NMR (400 MHz, CDCl$_3$) δ 7.40-7.20 (m, 5H), 1.54-1.48 (m, 9H), 6.67 (s, 1H), 4.45 (s, 1H), 3.98-3.77 (m, 2H), 3.32-3.16 (m, 1H), 2.44 (s, 3H). MS (ESI) mass calcd. C$_{17}$H$_{22}$N$_4$O$_2$, 315.3; m/z found, 316.2 [M+H]$^+$.

Intermediate 53G: 3-methyl-8-phenyl-5,6,7,8-tetrahydro-[1,2,4]triazolo[4,3-a]pyrazine

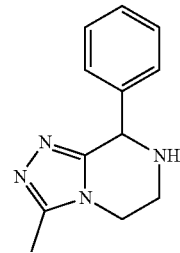

Step G: 3-methyl-8-phenyl-5,6,7,8-tetrahydro-[1,2,4]triazolo[4,3-a]pyrazine. To a solution of 3-methyl-8-phenyl-5,6-dihydro-[1,2,4]triazolo[4,3-a]pyrazine-7(8H)-carboxylate (390 mg, 1.241 mmol)) in 5 mL of DCM was added Trifluoroacetic acid (0.390 mL, 5.096 mmol). The resulting reaction mixture was allowed to stir at room temperature overnight. The reaction mixture was concentrated into a brown residue under reduced pressure and then washed with conc. NaHCO$_3$ solution and extracted three times with DCM. The combined organic layers were dried using MgSO$_4$, filtered and concentrated to provide the desired product (120 mg, 45%). MS (ESI) mass calcd. C$_{12}$H$_{14}$N$_4$, 214.2; m/z found, 215.2 [M+H]$^+$.

Example 53: (2-chloro-3-(trifluoromethyl)phenyl)(3-methyl-8-phenyl-5,6-dihydro-[1,2,4]triazolo[4,3-a]pyrazin-7(8H)-yl)methanone

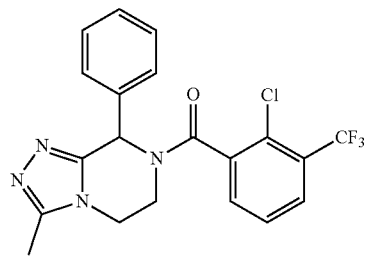 [SMILES: Cc1nnc2n1CCN(C(=O)c1cccc(C(F)(F)F)c1Cl)C2c1ccccc1]

Step H: (2-chloro-3-(trifluoromethyl)phenyl)(3-methyl-8-phenyl-5,6-dihydro-[1,2,4]triazolo[4,3-a]pyrazin-7(8H)-yl)methanone. To a solution of 3-methyl-8-phenyl-5,6,7,8-tetrahydro-[1,2,4]triazolo[4,3-a]pyrazine (120 mg, 0.560 mmol) in 5 mL of DCM was added triethylamine (0.234 mL, 1.68 mmol). The resulting reaction mixture was stirred for 5 min at room temperature and then cooled to 0° C. 2-chloro- 3-(trifluoromethyl)benzoyl chloride (272 mg, 1.120 mmol) was subsequently added and the reaction was stirred at 0° C. for 20 min. The reaction was quenched with water and warmed to room temperature then extracted three times with DCM. The combined organic layers were dried using MgSO₄ and concentrated into a residue, which was purified via basic HPLC (Agilent prep system, Waters XBridge C18 5 μm 50×100 mm column, 5-95% MeCN/20 nM NH₄OH over 22 min at 80 mL/min) to provide the racemic product (157 mg, 67%). ¹H NMR (500 MHz, CDCl₃) δ 7.87-7.70 (m, 1H), 7.60-7.29 (m, 7H), 6.21-5.93; 5.21-5.01 (m, 1H), 4.16-3.30 (m, 4H), 2.51-2.45 (m, 3H). MS (ESI): mass calcd. for $C_{20}H_{16}ClF_3N_4O$, 420.1; m/z found, 421.0 [M+H]⁺.

Example 54: (S)-(2,3-dichlorophenyl)(3-(6-fluoro-pyridin-2-yl)-6-methyl-5,6-dihydro-[1,2,4]triazolo[4,3-a]pyrazin-7(8H)-yl)methanone

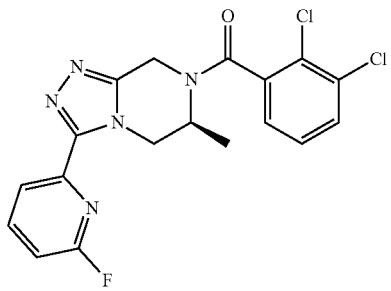 [SMILES: C[C@H]1Cn2c(nnc2-c2cccc(F)n2)CN1C(=O)c1cccc(Cl)c1Cl]

To a solution of (S)-3-(6-fluoro-2-pyridyl)-6-methyl-5,6,7,8-tetrahydro-[1,2,4]triazolo[4,3-a]pyrazine (110 mg, 0.41 mmol) (prepared as described in Example 54, Intermediate 54B, replacing 4-methoxy-pyridine-2-carboxylic acid hydrazide with 6-fluoro-pyridine-2-carboxylic acid hydrazide in step for intermediate 54A) and triethylamine (0.283 mL, 2.04 mmol) in CH₂Cl₂ (3 mL) was added 2,3-dichlorobenzoyl chloride (128.1 mg, 0.61 mmol) at 0° C. The reaction mixture was slowly warmed to room temperature and stirred for 1 h. The reaction mixture was quenched with water and extracted with CH₂Cl₂. The organic layers were separated, dried (Na₂SO₄), filtered and the solvent concentrated in vacuo. The crude compound was purified by column chromatography (silica, MeOH in EtOAC 0:100 to 10:90), the desired fractions were collected, the solvent evaporated to give (S)-(2,3-dichlorophenyl)(3-(6-fluoro-pyridin-2-yl)-6-methyl-5,6-dihydro-[1,2,4]triazolo[4,3-a]pyrazin-7(8H)-yl)methanone (100 mg, 60%) as a white foam. ¹H NMR (500 MHz, CDCl₃) δ ppm 1.22 (d, J=6.9 Hz, 0.90H), 1.36-1.41 (m, 1.05H), 1.43 (d, J=6.9 Hz, 1.05H), 4.09-4.27 (m, 0.80H), 4.42-4.51 (m, 0.70H), 4.55-4.84 (m, 1.70H), 4.98 (d, J=13.9 Hz, 0.30H), 5.04 (d, J=13.9 Hz, 0.50H), 5.54-5.63 (m, 0.50H), 5.82 (d, J=18.5 Hz, 0.30H), 5.95 (d, J=18.2 Hz, 0.20H), 7.00 (ddd, J=15.4, 8.2, 2.5 Hz, 1H), 7.17-7.39 (m, 2H), 7.54-7.61 (m, 1H), 7.91-8.00 (m, 1H), 8.20-8.31 (m, 1H). MS (ESI): mass calcd. For $C_{18}H_{14}Cl_2FN_5O$, 405.1; m/z found, 406.04 [M+H]⁺, [α]=+84.4° (589 nm, c 0.55 w/v %, DMF, 20° C.

Example 55: (S)-(2,3-dichlorophenyl)(3-(4-methoxypyridin-2-yl)-6-methyl-5,6-dihydro-[1,2,4]triazolo[4,3-a]pyrazin-7(8H)-yl)methanone

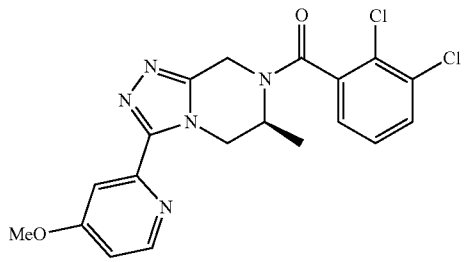 [SMILES: COc1ccnc(-c2nnc3n2C[C@H](C)N(C(=O)c2cccc(Cl)c2Cl)C3)c1]

Intermediate 55A: (S)-tert-butyl 3-(4-methoxy-2-pyridyl)-6-methyl-6,8-dihydro-5H-[1,2,4]triazolo[4,3-a]pyrazine-7-carboxylate To a solution of (S)-tert-butyl 2-methyl-5-thioxo-piperazine-1-carboxylate (Intermediate 26A, 0.5 g, 2.17 mmol) in ethanol (5 mL) was added 4-methoxy-pyridine-2-carboxylic acid hydrazide (435 mg, 2.61 mmol). The reaction mixture was heated at 150° C. in a sealed tube for 12 hours in a Q-TUBE. The solvent was then evaporated and the crude product purified by column chromatography (silica, MeOH in EtOAc 0:100 to 10:90). The desired fractions were collected and the solvent was evaporated to afford (S)-tert-butyl 3-(4-methoxy-2-pyridyl)-6-methyl-6,8-dihydro-5H-[1,2,4]triazolo[4,3-a]pyrazine-7-carboxylate as an off-white solid that was used for the next reaction step without further purification.

Intermediate 55B: (S)-3-(4-m ethoxy-2-pyridyl)-6-methyl-5,6,7,8-tetrahydro-[1,2,4]triazolo[4,3-a]pyrazine Trifluoroacetic acid (2.5 mL, 32.67 mmol) was added to a mixture of (S)-tert-butyl 3-(4-methoxy-2-pyridyl)-6-methyl-6,8-dihydro-5H-[1,2,4]triazolo[4,3-a]pyrazine-7-carboxylate (457 mg, 1.32 mmol) in CH₂Cl₂ (2.5 mL). The solution was stirred for 15 min at room temperature and then the mixture was basified with aq. sat NaHCO₃ and extracted with CH₂Cl₂. The organic layers were separated, dried (Na₂SO₄), filtered and the solvent concentrated in vacuo to yield (S)-3-(4-methoxy-2-pyridyl)-6-methyl-5,6,7,8-tetrahydro-[1,2,4]triazolo[4,3-a]pyrazine (121 mg, 37.3%) as an off-white solid.

Example 55: (S)-(2,3-dichlorophenyl)(3-(4-methoxypyridin-2-yl)-6-methyl-5,6-dihydro-[1,2,4]triazolo[4,3-a]pyrazin-7(8H)-yl)methanone 2,3-Dichlorobenzoyl chloride (103.3 mg, 0.49 mmol) was added to a stirred solution of (S)-3-(4-m ethoxy-2-pyridyl)-6-methyl-5,6,7,8-tetrahydro-[1,2,4]triazolo[4,3-a]pyrazine (121 mg, 0.49 mmol) and triethylamine (0.171 mL, 1.23 mmol) in CH₂Cl₂ under nitrogen at 0° C. The reaction mixture was slowly warmed to room temperature and stirred for 1 h. The reaction mixture was quenched with water and extracted with CH₂Cl₂ (1.5 mL). The organic layers were separated, dried (Na₂SO₄), filtered and the solvent concentrated in vacuo. The crude product was purified by column chromatography (silica, MeOH in EtOAc 0:100 to 10:90)

and the desired fractions were collected and the solvent evaporated. The residue was further purified by column chromatography (silica, CH₃CN in CH₂Cl₂ 0/100 to 100/0). The desired fractions were collected and the solvent evaporated. The residue was triturated with diisopropyl ether to yield (S)-(2,3-dichlorophenyl)(3-(4-methoxypyridin-2-yl)-6-methyl-5,6-dihydro-[1,2,4]triazolo[4,3-a]pyrazin-7(8H)-yl)methanone (81 mg, 39.3%) as an off-white solid. $^1$H NMR (400 MHz, CDCl₃) δ ppm 1.19 (d, J=6.9 Hz, 0.90H), 1.37 (d, J=6.9 Hz, 0.60H), 1.38 (d, J=6.9 Hz, 0.30H), 1.41 (d, J=7.2 Hz, 1.20H), 3.93 (s, 0.90H), 3.94 (s, 2.10H), 4.05-4.17 (m, 0.50H), 4.21 (dd, J=13.5, 4.5 Hz, 0.20H), 4.38-4.49 (m, 0.80H), 4.54-4.75 (m, 1.10H), 4.77 (d, J=17.1 Hz, 0.40H), 4.89 (d, J=13.6 Hz, 0.20H), 5.02-5.19 (m, 0.80H), 5.49-5.60 (m, 0.50H), 5.80 (d, J=18.3 Hz, 0.30H), 5.94 (d, J=18.3 Hz, 0.20H), 6.87 (ddd, J=12.5, 5.8, 2.5 Hz, 1H), 7.17-7.39 (m, 2H), 7.54-7.60 (m, 1H), 7.83-7.91 (m, 1H), 8.31-8.37 (m, 0.40H), 8.43 (d, J=5.8 Hz, 0.60H). MS (ESI): mass calcd. for C₁₉H₁₇Cl₂N₅O₂, 417.1; m/z found, 418.3[M+H]⁺. [α]=+62.4° (589 nm, c 0.42 w/v %, DMF, 20° C.).

Example 56: (2-chlorophenyl)(6-methyl-3-phenyl-5,6-dihydro-[1,2,4]triazolo[4,3-a]pyrazin-7(8H)-yl)methanone

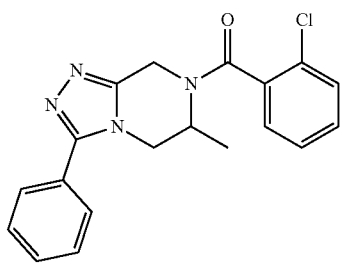 [SMILES: CC1Cn2c(nnc2-c2ccccc2)CN1C(=O)c1ccccc1Cl]

Example 57: (3,4-difluoro-2-methylphenyl)(6-methyl-3-phenyl-5,6-dihydro-[1,2,4]triazolo[4,3-a]pyrazin-7(8H)-yl)methanone

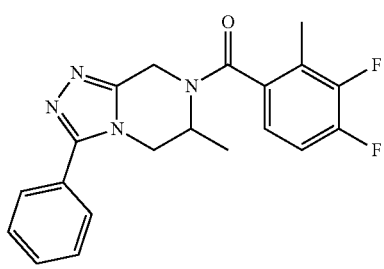 [SMILES: Cc1c(C(=O)N2Cc3nnc(-c4ccccc4)n3CC2C)ccc(F)c1F]

Example 58: (2-chloro-4-fluorophenyl)(6-methyl-3-phenyl-5,6-dihydro-[1,2,4]triazolo[4,3-a]pyrazin-7(8H)-yl)methanone

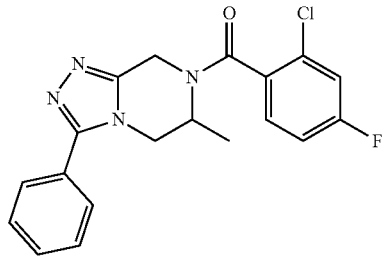 [SMILES: CC1Cn2c(nnc2-c2ccccc2)CN1C(=O)c1ccc(F)cc1Cl]

Example 59: (2,3-dichloropyridin-4-yl)(6-methyl-3-phenyl-5,6-dihydro-[1,2,4]triazolo[4,3-a]pyrazin-7(8H)-yl)methanone

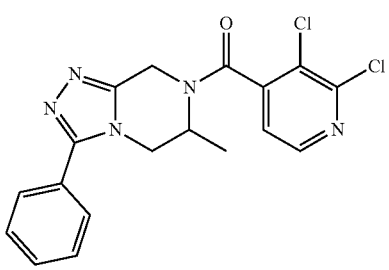

Example 60: (3-cyclohexyl-8-methyl-5,6-dihydro-[1,2,4]triazolo[4,3-a]pyrazin-7(8H)-yl)(2,3-dichlorophenyl)methanone

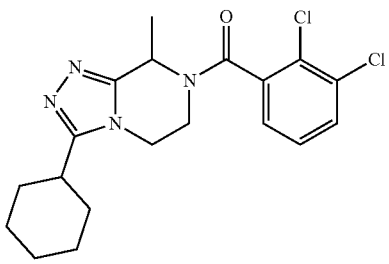 [SMILES: CC1c2nnc(C3CCCCC3)n2CCN1C(=O)c1cccc(Cl)c1Cl]

(R,S)-(3-cyclohexyl-8-methyl-5,6-dihydro-[1,2,4]triazolo[4,3-a]pyrazin-7(8H)-yl)(2,3-dichlorophenyl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in (R,S)-tert-butyl 2-methyl-3-thioxopiperazine-1-carboxylate was used in place of (S)-tert-butyl 2-methyl-5-thioxopiperazine-1-carboxylate and cyclohexanecarbohydrazide was used in in place of 4-(trifluoromethyl)benzohydrazide. 1H NMR (600 MHz, DMSO) δ 7.92-7.36 (m, 3H), 6.02-5.81 (m, 1H), 4.23-3.53 (m, 3H), 2.95-2.75 (m, 1H), 2.06-1.16 (m, 14H). MS (ESI): mass calcd. for C₁₉H₂₂Cl₂N₄O, 392.1; m/z found, 393.2 [M+H]⁺.

Example 61: (2-chloro-3-(trifluoromethyl)phenyl)
(3-cyclohexyl-8-methyl-5,6-dihydro-[1,2,4]triazolo
[4,3-a]pyrazin-7(8H)-yl)methanone

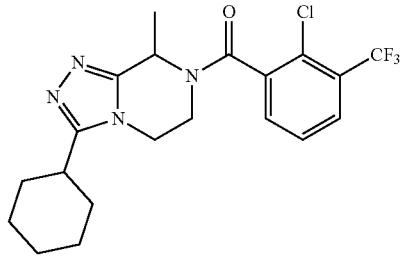 [SMILES: CC1c2nnc(C3CCCCC3)n2CCN1C(=O)c1cccc(C(F)(F)F)c1Cl]

(R,S)-(2-chloro-3-(trifluoromethyl)phenyl)(3-cyclohexyl-8-methyl-5,6-dihydro-[1,2,4]triazolo[4,3-a]pyrazin-7(8H)-yl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in (R,S)-tert-butyl 2-methyl-3-thioxopiperazine-1-carboxylate was used in place of (S)-tert-butyl 2-methyl-5-thioxopiperazine-1-carboxylate and cyclohexanecarbohydrazide was used in place of 4-(trifluoromethyl)benzohydrazide and 2-chloro-3-(trifluoromethyl)benzoyl chloride was used in place of 2,3-dichlorobenzoyl chloride. 1H NMR (600 MHz, DMSO) δ 8.10-7.57 (m, 3H), 5.98-5.81 (m, 1H), 4.35-3.42 (m, 3H), 3.01-2.80 (m, 1H), 2.02-1.19 (m, 14H). MS (ESI): mass calcd. for $C_{20}H_{22}ClF_3N_4O$, 426.1; m/z found, 427.2 [M+H]$^+$.

Example 62: (3-cyclohexyl-8-methyl-5,6-dihydro-
[1,2,4]triazolo[4,3-a]pyrazin-7(8H)-yl)(2,3-dichloro-
4-fluorophenyl)methanone

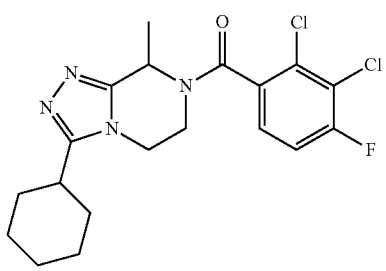 [SMILES: CC1c2nnc(C3CCCCC3)n2CCN1C(=O)c1ccc(F)c(Cl)c1Cl]

(R,S)-(3-cyclohexyl-8-methyl-5,6-dihydro-[1,2,4]triazolo[4,3-a]pyrazin-7(8H)-yl)(2,3-dichloro-4-fluorophenyl)methanone was generated in a manor analogous to that described for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein (R,S)-tert-butyl 2-methyl-3-thioxopiperazine-1-carboxylate was used in place of (S)-tert-butyl 2-methyl-5-thioxopiperazine-1-carboxylate, cyclohexanecarbohydrazide was used in place of 4-(trifluoromethyl)benzohydrazide and 2,3-dichloro-4-fluorobenzoyl chloride was used in place of 2,3-dichlorobenzoyl chloride. 1H NMR (600 MHz, DMSO) δ 7.98-7.40 (m, 2H), 5.88-5.69 (d, J=6.7 Hz, 1H), 4.06-3.48 (m, 4H), 1.96-1.07 (m, 14H). MS (ESI): mass calcd. for $C_{19}H_{21}Cl_2FN_4O$, 410.1; m/z found, 411.2 [M+H]$^+$.

Example 63: (3-cyclopropyl-8-methyl-5,6-dihydro-
[1,2,4]triazolo[4,3-a]pyrazin-7(8H)-yl)(2,3-dichloro-
phenyl)methanone

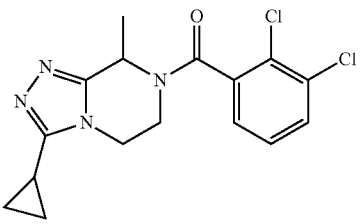 [SMILES: CC1c2nnc(C3CC3)n2CCN1C(=O)c1cccc(Cl)c1Cl]

(R,S)-(3-cyclopropyl-8-methyl-5,6-dihydro-[1,2,4]triazolo[4,3-a]pyrazin-7(8H)-yl)(2,3-dichlorophenyl)methanone was generated in a manor analogous to that described for (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone wherein (R,S)-tert-butyl 2-methyl-3-thioxopiperazine-1-carboxylate was used in place of (S)-tert-butyl 2-methyl-5-thioxopiperazine-1-carboxylate and cyclopropanecarbohydrazide was used in place of 4-(trifluoromethyl)benzohydrazide. 1H NMR (600 MHz, DMSO) δ 7.89-7.31 (m, 3H), 5.94-5.79 (m, 1H), 4.93-2.96 (m, 4H), 2.15-1.95 (m, 1H), 1.48-0.66 (m, 7H).

Example 64: (3-cyclopropyl-8-methyl-5,6-dihydro-
[1,2,4]triazolo[4,3-a]pyrazin-7(8H)-yl)(2,3-dichloro-
4-fluorophenyl)methanone

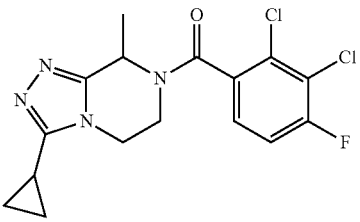 [SMILES: CC1c2nnc(C3CC3)n2CCN1C(=O)c1ccc(F)c(Cl)c1Cl]

(R,S)-(3-cyclopropyl-8-methyl-5,6-dihydro-[1,2,4]triazolo[4,3-a]pyrazin-7(8H)-yl)(2,3-dichloro-4-fluorophenyl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in (R,S)-tert-butyl 2-methyl-3-thioxopiperazine-1-carboxylate was used in place of (S)-tert-butyl 2-methyl-5-thioxopiperazine-1-carboxylate, cyclopropanecarbohydrazide was used in place of 4-(trifluoromethyl)benzohydrazide and 2,3-dichloro-4-fluorobenzoyl chloride was used in place of 2,3-dichlorobenzoyl chloride. 1H NMR (600 MHz, CDCl$_3$) δ 12.48-12.11 (m, 2H), 10.61-10.45 (d, J=6.8 Hz, 1H), 9.53-8.35 (m, 4H), 6.81-6.64 (m, 1H), 6.44-5.46 (m, 7H).

Example 65: (2-chloro-3-(trifluoromethyl)phenyl)(3-cyclopropyl-8-methyl-5,6-dihydro-[1,2,4]triazolo[4,3-a]pyrazin-7(8H)-yl)methanone

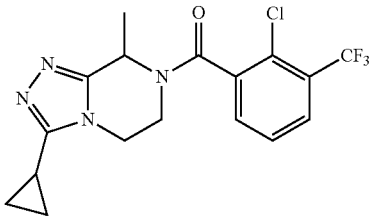 [SMILES: CC1c2nnc(C3CC3)n2CCN1C(=O)c1cccc(C(F)(F)F)c1Cl]

(R,S)-(2-chloro-3-(trifluoromethyl)phenyl)(3-cyclopropyl-8-methyl-5,6-dihydro-[1,2,4]triazolo[4,3-a]pyrazin-7(8H)-yl)methanone was generated in a manor analogous to (S)-(2,3-dichlorophenyl)(6-methyl-3-(4-(trifluoromethyl)phenyl)-5,6-dihydro-[1,2,4]triazolo[4,3-a]pyrazin-7(8H)-yl)methanone where in (R,S)-tert-butyl 2-methyl-3-thioxopiperazine-1-carboxylate was used in place of (S)-tert-butyl 2-methyl-5-thioxopiperazine-1-carboxylate, cyclopropanecarbohydrazide was used in place of 4-(trifluoromethyl)benzohydrazide and 2-chloro-3-(trifluoromethyl)benzoyl chloride was used in place of 2,3-dichlorobenzoyl chloride. 1H NMR (600 MHz, DMSO) δ 8.08-7.54 (m, 3H), 5.94-5.74 (m, 1H), 4.97-2.99 (m, 4H), 2.16-1.91 (m, 1H), 1.69-0.81 (m, 7H).

Example 66: (S)-(2-chloro-3-(trifluoromethyl)phenyl)(3-methyl-8-phenyl-5,6-dihydro-[1,2,4]triazolo[4,3-a]pyrazin-7(8H)-yl)methanone

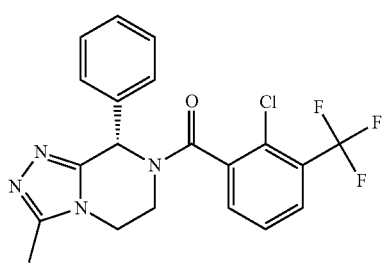 [SMILES: Cc1nnc2n1CCN(C(=O)c1cccc(C(F)(F)F)c1Cl)[C@H]2c1ccccc1]

The desired product was prepared in an analogous manner to example 53. The racemic product was separated via chiral SFC (Stationary phase: CHIRALPAK AD-H 5 μm 250×20 mm), (Mobile phase: 65% $CO_2$, 35% iPrOH) yielding the desired product. $^1$H NMR (400 MHz, $CDCl_3$) δ 7.86-7.73 (m, 1H), 7.58-7.28 (m, 7H), 6.16-5.99; 5.21-5.05 (m, 1H), 4.16-3.31 (m, 4H), 2.53-2.40 (m, 3H). MS (ESI) mass calcd. for $C_{20}H_{16}ClF_3N_4O$, 420.1; m/z found, 421.0 [M+H]$^+$.

Example 67: (R)-(2-chloro-3-(trifluoromethyl)phenyl)(3-methyl-8-phenyl-5,6-dihydro-[1,2,4]triazolo[4,3-a]pyrazin-7(8H)-yl)methanone

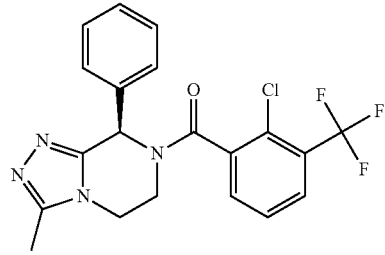 [SMILES: Cc1nnc2n1CCN(C(=O)c1cccc(C(F)(F)F)c1Cl)[C@@H]2c1ccccc1]

The desired product was prepared in an analogous manner to example 53. The racemic product was separated via chiral SFC (Stationary phase: CHIRALPAK AD-H 5 μm 250×20 mm), (Mobile phase: 65% $CO_2$, 35% iPrOH) yielding the desired product. $^1$H NMR (400 MHz, $CDCl_3$) δ 7.84-7.74 (m, 1H), 7.58-7.28 (m, 7H), 6.15-5.99; 5.19-5.05 (m, 1H), 4.17-3.31 (m, 4H), 2.53-2.43 (m, 3H). MS (ESI) mass calcd. $C_{20}H_{16}ClF_3N_4O$, 420.1; m/z found, 421.0 [M+H]$^+$.

Example 68: (S)-(2,3-dichlorophenyl)(3-(4-fluoropyridin-2-yl)-6-methyl-5,6-dihydro-[1,2,4]triazolo[4,3-a]pyrazin-7(8H)-yl)methanone To a solution of (S)-3-(4-iodopyridin-2-yl)-6-methyl-5,6,7,8-tetrahydro-[1,2,4]triazolo[4,3-a]pyrazine (30 mg, 0.088 mmol) (generated in a manor analogous to Intermediate 21E wherein 4-iodopicolinohydrazide was used in place of 4-fluorobenzhydrazide) in $CH_2Cl_2$ (1 mL) was added triethylamine (0.04 mL, 0.3 mmol) and 2,3-dichlorobenzoyl chloride (24 mg, 0.11 mmol). The reaction was allowed to stir at rt for 30 min and then evaporated in vacuo. The residue was chromatographed ($SiO_2$, 0-10% 2 N $NH_3$ in MeOH)/$CH_2Cl_2$). After concentration in vacuo the resulting residue was dissolved in dry THF (0.2 mL) and tetrabutylammonium fluoride THF solution (0.041 mL, 0.041 mmol) was added. The reaction was heated to 120° C. for 5 min in the microwave. An additional 0.041 mmol TBAF was added and the reaction was heated in the microwave to 150° C. for 5 min, followed by 160° C. for 30 min and 165° C. for 40 min, and finally 160° C. for 90 min. The reaction was purified by prep HPLC (C18 XSelect 19×100 5 μm, Mobile phase Gradient from 80% 0.1% $NH_4CO_3H/NH_4OH$ pH 9 solution in Water, 20% $CH_3CN$ to 0% 0.1% $NH_4CO_3H/NH_4OH$ pH 9 solution in Water, 100% $CH_3CN$) 1.6 mg, 9.6%). MS (ESI) mass calcd. $C_{18}H_{14}Cl_2FN_5O$, 405.1; m/z found, 405.0.

Example 69: (S)-(2,3-dichlorophenyl)(3-(5-fluoro-pyridin-2-yl)-6-methyl-5,6-dihydro-[1,2,4]triazolo[4,3-a]pyrazin-7(8H)-yl)methanone

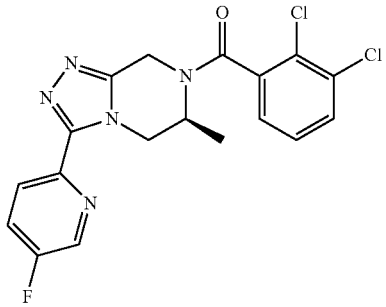 [SMILES: C[C@H]1Cn2c(nnc2-c2ccc(F)cn2)CN1C(=O)c1cccc(Cl)c1Cl]

2,3-Dichlorobenzoyl chloride (94.3 mg, 0.45 mmol) was added to a stirred solution of (S)-3-(5-fluoro-2-pyridyl)-6-methyl-5,6,7,8-tetrahydro-[1,2,4]triazolo[4,3-a]pyrazine (70 mg, 0.30 mmol) (prepared as described in Example 54, Intermediate 54B, replacing 4-methoxy-pyridine-2-carboxylic acid hydrazide with 5-fluoro-pyridine-2-carboxylic acid hydrazide in step for intermediate 54A) and triethylamine (0.21 mL, 1.50 mmol) in $CH_2Cl_2$ (2 mL) under nitrogen at 0° C. The reaction mixture was slowly warmed to room temperature and stirred for 30 additional min. The reaction mixture was quenched with water and extracted with $CH_2Cl_2$. The organic layers were separated, dried ($Na_2SO_4$), filtered and the solvent concentrated in vacuo. The crude product was purified by column chromatography (silica, MeOH in EtOAc 0:100 to 10:90), the desired fractions were collected and the solvent evaporated in vacuo to yield the desired compound with some impurities. This was purified by RP HPLC on (C18 Sunfire 30×100 5um). Mobile phase (Gradient from 50% 0.1% $NH_4CO_2CH_3$ solution in Water, 40% $CH_3CN$ to 40% 0.1% $NH_4CO_2CH_3$ solution in Water, 50% $CH_3CN$), yielding (S)-(2,3-dichlorophenyl)(3-(5-fluoropyridin-2-yl)-6-methyl-5,6-dihydro-[1,2,4]triazolo[4,3-a]pyrazin-7(8H)-yl)methanone (31.3 mg, 24.4%). MS (ESI) mass calcd. $C_{18}H_{14}Cl_2FN_5O$, 405.1; m/z found, 406.0 [M+H]$^+$. $^1$H NMR (500 MHz, CDCl$_3$) δ ppm 1.20 (d, J=6.6 Hz, 0.75H), 1.38 (d, J=6.9 Hz, 0.75H), 1.38 (d, J=6.9 Hz, 0.45H), 1.42 (d, J=7.2 Hz, 1.05H), 4.07-4.18 (m, 0.45H), 4.21 (dd, J=13.6, 4.6 Hz, 0.15H), 4.38-4.49 (m, 0.80H), 4.53-4.83 (m, 1.80H), 4.92-5.06 (m, 0.85H), 5.52-5.61 (m, 0.55H), 5.81 (d, J=18.5 Hz, 0.25H), 5.94 (d, J=18.2 Hz, 0.15H), 7.17-7.39 (m, 2H), 7.54-7.60 (m, 2H), 8.34-8.44 (m, 1.30H), 8.50 (d, J=2.6 Hz, 0.70H).

Example 70: (S)-(2-chloro-3-(trifluoromethyl)phenyl)(3-(5-fluoropyridin-2-yl)-6-methyl-5,6-dihydro-[1,2,4]triazolo[4,3-a]pyrazin-7(8H)-yl)methanone

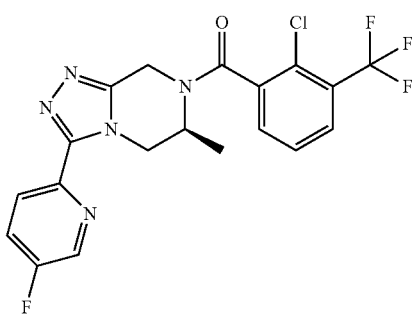 [SMILES: C[C@H]1Cn2c(nnc2-c2ccc(F)cn2)CN1C(=O)c1cccc(C(F)(F)F)c1Cl]

2-Chloro-3-(trifluoromethyl)benzoyl chloride (159.4 mg, 0.66 mmol) was added to a stirred solution of (S)-3-(5-fluoro-2-pyridyl)-6-methyl-5,6,7,8-tetrahydro-[1,2,4]triazolo[4,3-a]pyrazine (102 mg, 0.44 mmol) and triethylamine (0.30 mL, 2.19 mmol) in $CH_2Cl_2$ (3 mL) at 0° C. The reaction mixture was slowly warmed to room temperature and stirred for 90 min. The reaction mixture was quenched with water and extracted with $CH_2Cl_2$. The organic layers were separated, dried ($Na_2SO_4$), filtered and the solvent concentrated in vacuo. The crude product was purified by column chromatography (silica, MeOH in EtOAc 0/100 to 10/90), the desired fractions were collected and the solvent evaporated in vacuo. The product containing some impurities was purified by RP HPLC on (C18 Sunfire 30×100 5 um). Mobile phase (Gradient from 60% 0.1% $NH_4CO_2CH_3$ solution in Water, 40% $CH_3CN$ to 40% 0.1% $NH_4CO_2CH_3$ solution in Water, 60% $CH_3CN$), yielding (S)-(2-chloro-3-(trifluoromethyl)phenyl)(3-(5-fluoropyridin-2-yl)-6-methyl-5,6-dihydro-[1,2,4]triazolo[4,3-a]pyrazin-7(8H)-yl)methanone (0.27 g, 44.2%). MS (ESI) mass calcd. $C_{19}H_{14}ClF_4N_5O$, 439.1; m/z found, 440.0 [M+H]$^+$. $^1$H NMR (400 MHz, CDCl$_3$) δ ppm 1.22 (d, J=6.9 Hz, 0.75H), 1.39 (d, J=7.2 Hz, 0.45H), 1.40 (d, J=6.7 Hz, 0.60H), 1.43 (d, J=7.2 Hz, 1.20H), 4.04-4.14 (m, 0.40H), 4.21 (dd, J=13.6, 4.6 Hz, 0.15H), 4.39-4.49 (m, 0.85H), 4.56-4.85 (m, 1.80H), 4.93-5.09 (m, 0.85H), 5.53-5.63 (m, 0.55H), 5.82 (d, J=18.3 Hz, 0.25H), 5.96 (d, J=18.3 Hz, 0.15H), 7.45-7.61 (m, 3H), 7.79-7.86 (m, 1H), 8.33-8.44 (m, 1.40H), 8.51 (d, J=2.8 Hz, 0.60H). [α]=+60.6° (589 nm, c 0.5 w/v %, DMF, 20° C.).

Example 71: ((S)-(2-chloro-3-(trifluoromethyl)phenyl)(3-(5-methoxypyridin-2-yl)-6-methyl-5,6-dihydro-[1,2,4]triazolo[4,3-a]pyrazin-7(8H)-yl)methanone

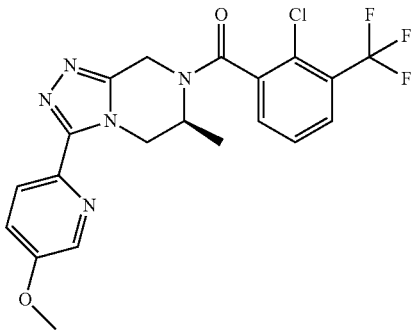

2-Chloro-3-(trifluoromethyl)benzoyl chloride (127.8 mg, 0.526 mmol) was added to a stirred solution of (S)-3-(5-methoxy-2-pyridyl)-6-methyl-5,6,7,8-tetrahydro-[1,2,4]triazolo[4,3-a]pyrazine (86 mg, 0.35 mmol) (prepared as described in Example 54, Intermediate 54B, replacing 4-methoxy-pyridine-2-carboxylic acid hydrazide with 5-methoxy-pyridine-2-carboxylic acid hydrazide in step for intermediate 54A) and triethylamine (0.24 mL, 1.75 mmol) in $CH_2Cl_2$ (3 mL) under nitrogen at 0° C. The reaction mixture was slowly warmed to room temperature and stirred for 30 min. The reaction mixture was quenched with water and extracted with $CH_2Cl_2$. The organic layers were separated, dried ($Na_2SO_4$), filtered and the solvent concentrated in vacuo. The crude product was purified twice by column chromatography (silica, MeOH in EtOAc 0:100 to 10:90), the desired fractions were collected and the solvent evaporated in vacuo. Final purification was performed by RP HPLC on (C18 Sunfire 30×100 5um). Mobile phase (Gradient from 60% 0.1% $NH_4CO_2CH_3$ solution in Water, 40% $CH_3CN$ to 40% 0.1% $NH_4CO_2CH_3$ solution in Water, 60% $CH_3CN$), yielding (S)-(2-chloro-3-(trifluoromethyl)phenyl)(3-(5-methoxypyridin-2-yl)-6-methyl-5,6-dihydro-[1,2,4]triazolo[4,3-a]pyrazin-7(8H)-yl)methanone (35.9 mg, 22.6%). MS (ESI) mass calcd. $C_{20}H_{17}ClF_3N_5O_2$, 451.1; m/z found, 452.1[M+H]$^+$. $^1$H NMR (500 MHz, CDCl$_3$) δ ppm 1.20 (d, J=6.9 Hz, 0.75H), 1.38 (dd, J=6.9, 2.0 Hz, 1.20H), 1.43 (d, J=7.2 Hz, 1.05H), 3.90-3.92 (m, 1.30H), 3.93 (s, 1.70H), 4.01-4.12 (m, 0.40H), 4.19 (dd, J=13.6, 4.6 Hz, 0.15H), 4.37-4.47 (m, 0.85H), 4.54-4.90 (m, 1.85H), 4.95-5.11 (m, 0.85H), 5.51-5.61 (m, 0.50H), 5.79 (d, J=18.2 Hz, 0.25H), 5.94 (d, J=18.2 Hz, 0.15H), 7.30-7.38 (m, 1H), 7.45-7.60 (m, 2H), 7.78-7.85 (m, 1H), 8.20-8.35 (m, 2H).

Example 72: (S)-(2,3-dichlorophenyl)(3-(5-methoxypyridin-2-yl)-6-methyl-5,6-dihydro-[1,2,4]triazolo[4,3-a]pyrazin-7(8H)-yl)methanone

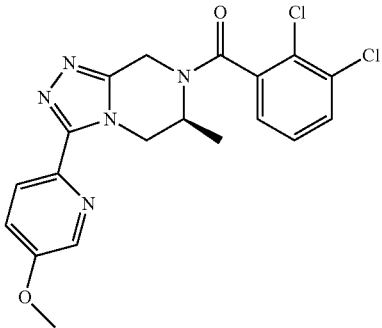 [SMILES: COc1ccc(-c2nnc3n2C[C@H](C)N(C(=O)c2cccc(Cl)c2Cl)C3)nc1]

The desired product was prepared in an analogous manner to Example 71, using 2,3-dichlorobenzoyl chloride instead of 2-chloro-3-(trifluoromethyl)benzoyl chloride. Further purification was not required. MS (ESI) mass calcd. $C_{19}H_{17}Cl_2N_5O_2$, 417.1; m/z found, 418.0 [M+H]$^+$. $^1$H NMR (500 MHz, CDCl$_3$) δ ppm 1.19 (d, J=6.9 Hz, 0.75H), 1.37 (d, J=6.6 Hz, 0.75H), 1.37 (d, J=6.9 Hz, 0.45H), 1.41 (d, J=6.9 Hz, 1.05H), 3.89-3.92 (m, 1.20H), 3.93 (s, 1.80H), 4.04-4.16 (m, 0.40H), 4.19 (dd, J=13.4, 4.8 Hz, 0.15H), 4.35-4.48 (m, 0.85H), 4.52-4.83 (m, 1.85H), 4.93-5.09 (m, 0.85H), 5.48-5.60 (m, 0.50H), 5.78 (d, J=18.2 Hz, 0.25H), 5.92 (d, J=18.2 Hz, 0.15H), 7.15-7.39 (m, 3H), 7.52-7.60 (m, 1H), 8.19-8.36 (m, 2H).

Example 73: (S)-(2,3-dichlorophenyl)(3-(5-fluoropyrimidin-2-yl)-6-methyl-5,6-dihydro-[1,2,4]triazolo[4,3-a]pyrazin-7(8H)-yl)methanone

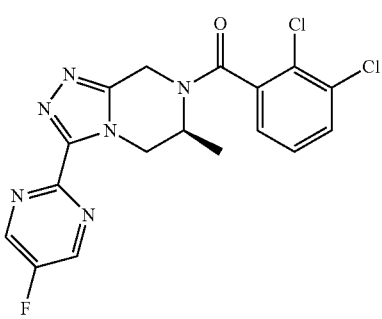 [SMILES: C[C@H]1Cn2c(nnc2-c2ncc(F)cn2)CN1C(=O)c1cccc(Cl)c1Cl]

2,3-Dichlorobenzoyl chloride (60 mg, 0.29 mmol) was added to a stirred solution of (S)-3-(5-fluoropyrimidin-2-yl)-6-methyl-5,6,7,8-tetrahydro-[1,2,4]triazolo[4,3-a]pyrazine (67 mg, 0.29 mmol) (prepared as described in Example 54, Intermediate 54B, replacing 4-methoxy-pyridine-2-carboxylic acid hydrazide with 5-fluoropyrimidine-2-carboxylic acid hydrazide in step for intermediate 54A) and triethylamine (0.20 mL, 1.43 mmol) in $CH_2Cl_2$ (15 mL) under nitrogen at 0° C. The reaction mixture was slowly warmed to room temperature and stirred for 1 h. The reaction mixture was quenched with water and extracted with $CH_2Cl_2$. The organic layers were separated, dried ($Na_2SO_4$), filtered and the solvent concentrated in vacuo. The crude product was purified by column chromatography (silica, MeOH in EtOAc 0:100 to 10:90), and the desired fractions were collected and the solvent evaporated in vacuo to yield (S)-(2,3-dichlorophenyl)(3-(5-fluoropyrimidin-2-yl)-6-methyl-5,6-dihydro-[1,2,4]triazolo[4,3-a]pyrazin-7(8H)-yl)methanone (45 mg, 38.5%). MS (ESI) mass calcd. $C_{17}H_{13}Cl_2FN_6O$, 406.1; m/z found, 406.9 [M+H]$^+$. $^1$H NMR (400 MHz, CDCl$_3$) δ ppm 1.21 (d, J=6.7 Hz, 0.75H), 1.38 (d, J=6.7 Hz, 0.60H), 1.39 (d, J=7.2 Hz, 0.60H), 1.43 (d, J=7.2 Hz, 1.05H), 4.10-4.27 (m, 0.60H), 4.38-4.98 (m, 3.35H), 5.55-5.65 (m, 0.60H), 5.85 (d, J=18.5 Hz, 0.25H), 5.97 (d, J=18.5 Hz, 0.20H), 7.17-7.41 (m, 2H), 7.55-7.62 (m, 1H), 8.74 (s, 0.45H), 8.74 (s, 0.45H), 8.78 (br s, 1H), M.P. 258.9° C. [α]=+56.8° (589 nm, c 0.48 w/v %, DMF, 20° C.).

Example 74: (S)-(2,3-dichlorophenyl)(3-(5-fluoropyrimidin-2-yl)-6-methyl-5,6-dihydro-[1,2,4]triazolo[4,3-a]pyrazin-7(8H)-yl)methanone

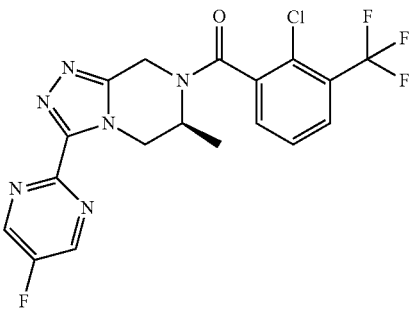 [SMILES: C[C@H]1Cn2c(nnc2-c2ncc(F)cn2)CN1C(=O)c1cccc(C(F)(F)F)c1Cl]

The desired product was prepared in an analogous manner to Example 73, using 2-chloro-3-(trifluoromethyl)benzoyl chloride instead of 2,3-dichlorobenzoyl chloride. MS (ESI) mass calcd. $C_{18}H_{13}ClF_4N_6O$, 440.1; m/z found, 441.0 [M+H]$^+$. $^1$H NMR (400 MHz, CDCl$_3$) δ ppm 1.22 (d, J=6.9 Hz, 0.75H), 1.40 (dd, J=6.9, 1.2 Hz, 1.05H), 1.44 (d, J=6.9 Hz, 1.20H), 4.06-4.19 (m, 0.55H), 4.23 (dd, J=13.5, 4.5 Hz, 0.15H), 4.39-4.53 (m, 0.80H), 4.59-5.01 (m, 2.50H), 5.56-5.67 (m, 0.60H), 5.86 (d, J=18.7 Hz, 0.25H), 5.99 (d, J=18.3 Hz, 0.15H), 7.46-7.60 (m, 2H), 7.80-7.87 (m, 1H), 8.73 (s, 0.30H), 8.75 (s, 0.50H), 8.78 (s, 1.20H). M.P.>300° C. [α]=+51.0° (589 nm, c 0.44 w/v %, DMF, 20° C.).

Example 75: (±)-(2-chloro-3-(trifluoromethyl)phenyl)(8-phenyl-3-(trifluoromethyl)-5,6-dihydro-[1,2,4]triazolo[4,3-a]pyrazin-7(8H)-yl)methanone

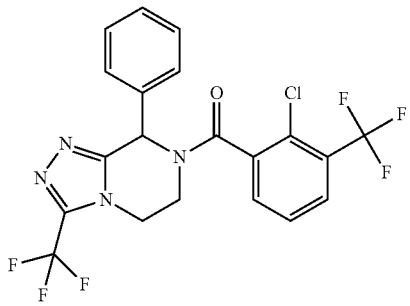 [SMILES: O=C(c1cccc(C(F)(F)F)c1Cl)N1CCn2c(nnc2C(F)(F)F)C1c1ccccc1]

The desired product was prepared in an analogous manner to example 108 (using trifluoroacetic anhydride instead of difluoroacetic anhydride in Step) and was purified via basic HPLC (Agilent prep system, Waters XBridge C18 5 um 50×100 mm column, 5-95% MeCN/20 nM NH$_4$OH over 22 min at 80 mL/min) to provide the racemic product (6.8 mg, 25%). $^1$H NMR (500 MHz, CDCl$_3$) δ 7.87-7.75 (m, 1H), 7.61-7.29 (m, 7H), 6.25-6.08; 5.22-5.09 (m, 1H), 4.39-3.35 (m, 4H). MS (ESI) mass calcd. C$_{20}$H$_{13}$ClF$_6$N$_4$O, 474.1; m/z found, 475.1 [M+H]$^+$.

Example 76: (S)-(2-chloro-3-(trifluoromethyl)phenyl)(3-cyclopropyl-8-phenyl-5,6-dihydro-[1,2,4]triazolo[4,3-a]pyrazin-7(8H)-yl)methanone

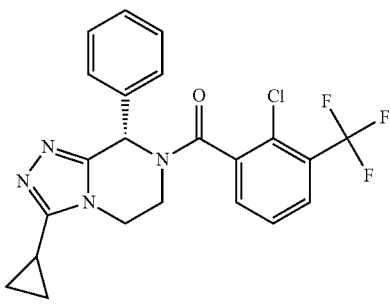 [SMILES: O=C(c1cccc(C(F)(F)F)c1Cl)N1CCn2c(C3CC3)nnc2[C@@H]1c1ccccc1]

The desired product was prepared in an analogous manner to example 53 (using cyclopropanecarbohydrazide instead of acetic hydrazide in Step F.) The racemic product was separated via chiral SFC (Stationary phase: CHIRALPAK AD-H 5 μm 250×20 mm), (Mobile phase: 70% CO$_2$, 30% iPrOH) yielding the desired product. $^1$H NMR (400 MHz, CDCl$_3$) δ 7.86-7.71 (m, 1H), 7.60-7.29 (m, 7H), 6.15-5.99; 5.20-5.02 (m, 1H), 4.25-3.30 (m, 4H), 1.78-1.68 (m, 1H), 1.28-1.16 (m, 2H), 1.16-0.99 (m, 2H). MS (ESI) mass calcd. C$_{22}$H$_{18}$ClF$_3$N$_4$O, 446.1; m/z found, 447.1 [M+H]$^+$.

Example 77: (R)-(2-chloro-3-(trifluoromethyl)phenyl)(3-cyclopropyl-8-phenyl-5,6-dihydro-[1,2,4]triazolo[4,3-a]pyrazin-7(8H)-yl)methanone

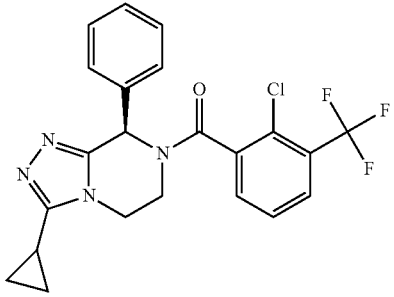 [SMILES: O=C(c1cccc(C(F)(F)F)c1Cl)N1CCn2c(C3CC3)nnc2[C@H]1c1ccccc1]

The desired product was prepared in an analogous manner to example 53 (using cyclopropanecarbohydrazide instead of acetic hydrazide in Step F.) The racemic product was separated via chiral SFC (Stationary phase: CHIRALPAK AD-H 5 μm 250×20 mm), (Mobile phase: 70% CO$_2$, 30% iPrOH) yielding the desired product. $^1$H NMR (400 MHz, CDCl$_3$) δ 7.88-7.68 (m, 1H), 7.60-7.29 (m, 7H), 6.19-5.93; 5.21-5.03 (m, 1H), 4.26-3.31 (m, 4H), 1.79-1.67 (m, 1H), 1.28-1.16 (m, 2H), 1.16-1.02 (m, 2H). MS (ESI) mass calcd. C$_{22}$H$_{18}$ClF$_3$N$_4$O, 446.1; m/z found, 447.0 [M+H]$^+$.

Example 78: (S)-(2-chloro-3-(trifluoromethyl)phenyl)(3-(5-methoxypyrimidin-2-yl)-6-methyl-5,6-dihydro-[1,2,4]triazolo[4,3-a]pyrazin-7(8H)-yl)methanone

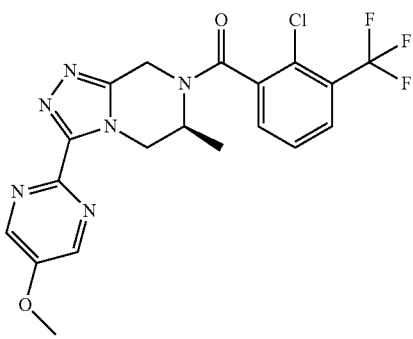 [SMILES: COc1cnc(-c2nnc3n2C[C@H](C)N(C(=O)c2cccc(C(F)(F)F)c2Cl)C3)nc1]

The desired product was prepared in an analogous manner to Example 74, replacing (S)-3-(5-fluoropyrimidin-2-yl)-6-methyl-5,6,7,8-tetrahydro-[1,2,4]triazolo[4,3-a]pyrazine with (S)-3-(5-methoxypyrimidin-2-yl)-6-methyl-5,6,7,8-tetrahydro-[1,2,4]triazolo[4,3-a]pyrazine. MS (ESI) mass calcd. C$_{19}$H$_{16}$ClF$_3$N$_6$O2, 452.1; m/z found, 453.0 [M+H]$^+$. $^1$H NMR (400 MHz, CDCl$_3$) δ ppm 1.21 (d, J=6.9 Hz, 0.75H), 1.39 (d, J=7.4 Hz, 0.45H), 1.39 (d, J=6.7 Hz, 0.60H), 1.43 (d, J=7.2 Hz, 1.20H), 3.99 (s, 0.60H), 4.00 (s, 0.75H), 4.02 (s, 1.65H), 4.04-4.16 (m, 0.55H), 4.20 (dd, J=13.8, 4.5 Hz, 0.15H), 4.37-4.50 (m, 0.80H), 4.57-5.03 (m, 2.50H), 5.54-5.64 (m, 0.60H), 5.83 (d, J=18.5 Hz, 0.25H), 5.97 (d, J=18.3 Hz, 0.15H), 7.45-7.60 (m, 2H), 7.78-7.88 (m, 1H), 8.50 (s, 0.30H), 8.52 (s, 0.50H), 8.55 (s, 1.20H), M.P. 129.4° C.

Example 79: (±)-(2-chloro-3-(trifluoromethyl)phenyl)(3-(furan-2-yl)-8-phenyl-5,6-dihydro-[1,2,4]triazolo[4,3-a]pyrazin-7(8H)-yl)methanone

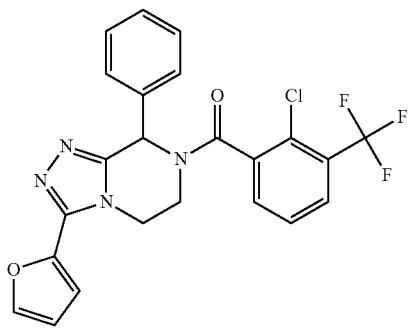 [SMILES: O=C(c1cccc(C(F)(F)F)c1Cl)N1CCn2c(-c3ccco3)nnc2C1c1ccccc1]

The desired product was prepared in an analogous manner to example 53 (using oxazole-2-carbohydrazide instead of acetic hydrazide in Step F.) $^1$H NMR (500 MHz, CDCl$_3$) δ 7.86-7.71 (m, 1H), 7.63-7.59 (m, 1H), 7.57-7.28 (m, 7H), 7.21-7.13 (m, 1H), 6.65-6.54 (m, 1H), 6.26-6.00; 5.17-5.04 (m, 1H), 4.61-3.36 (m, 4H). MS (ESI) mass calcd. C$_{23}$H$_{16}$ClF$_3$N$_4$O$_2$, 472.1; m/z found, 473.1 [M+H]$^+$.

Example 80: (±)-(2-chloro-3-(trifluoromethyl)phenyl)(3-(1-hydroxyethyl)-8-phenyl-5,6-dihydro-[1,2,4]triazolo[4,3-a]pyrazin-7(8H)-yl)methanone

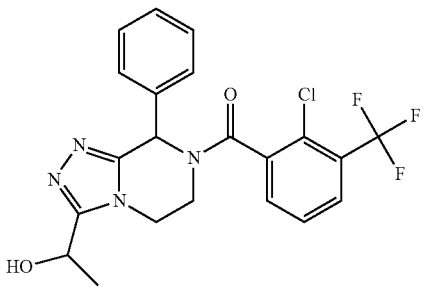 [SMILES: CC(O)c1nnc2n1CCN(C(=O)c1cccc(C(F)(F)F)c1Cl)C2c1ccccc1]

The desired product was prepared in an analogous manner to example 53 (using 2-hydroxypropanehydrazide instead of acetic hydrazide in Step F.) $^1$H NMR (500 MHz, CDCl$_3$) δ 7.83-7.74 (m, 1H), 7.59-7.29 (m, 7H), 6.16-5.99; 5.15-4.97 (m, 2H), 4.47-2.76 (m, 5H), 1.79-1.65 (m, 3H). MS (ESI) mass calcd. C$_{21}$H$_{18}$ClF$_3$N$_4$O$_2$, 450.1; m/z found, 451.2 [M+H]$^+$.

Example 81: (R)-(3-(tert-butyl)-8-phenyl-5,6-dihydro-[1,2,4]triazolo[4,3-a]pyrazin-7(8H)-yl)(2-chloro-3-(trifluoromethyl)phenyl)methanone

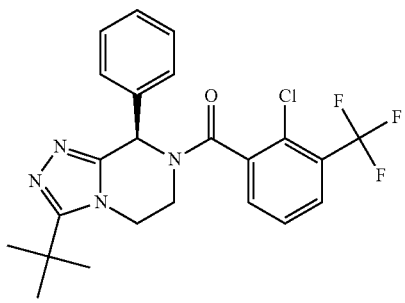 [SMILES: CC(C)(C)c1nnc2n1CCN(C(=O)c1cccc(C(F)(F)F)c1Cl)[C@@H]2c1ccccc1]

The desired product was prepared in an analogous manner to example 53 (using pivalohydrazide instead of acetic hydrazide in Step F.) The racemic product was separated via chiral SFC (Stationary phase: CHIRALPAK AD-H 5 μm 250×20 mm), (Mobile phase: 80% CO$_2$, 20% iPrOH) yielding the desired product. $^1$H NMR (400 MHz, CDCl$_3$) δ 7.86-7.71 (m, 1H), 7.60-7.28 (m, 7H), 6.20-6.01; 5.13-4.91 (m, 1H), 4.36-3.31 (m, 4H), 1.53-1.46 (m, 9H). MS (ESI) mass calcd. C$_{23}$H$_{22}$ClF$_3$N$_4$O, 462.1; m/z found, 463.1 [M+H]$^+$.

Example 82: (S)-(3-(tert-butyl)-8-phenyl-5,6-dihydro-[1,2,4]triazolo[4,3-a]pyrazin-7(8H)-yl)(2-chloro-3-(trifluoromethyl)phenyl)methanone

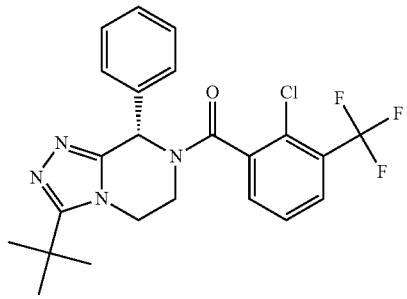 [SMILES: CC(C)(C)c1nnc2n1CCN(C(=O)c1cccc(C(F)(F)F)c1Cl)[C@H]2c1ccccc1]

The desired product was prepared in an analogous manner to example 53 (using pivalohydrazide instead of acetic hydrazide in Step F.) The racemic product was separated via chiral SFC (Stationary phase: CHIRALPAK AD-H 5 μm 250×20 mm), (Mobile phase: 80% CO$_2$, 20% iPrOH) yielding the desired product. $^1$H NMR (400 MHz, CDCl$_3$) δ 7.84-7.72 (m, 1H), 7.58-7.28 (m, 7H), 6.20-6.01; 5.12-4.96 (m, 1H), 4.34-3.29 (m, 4H), 1.53-1.45 (m, 9H). MS (ESI) mass calcd. C$_{23}$H$_{22}$ClF$_3$N$_4$O, 462.1; m/z found, 463.1 [M+H]$^+$.

Example 83: (R)-(2-chloro-3-(trifluoromethyl)phenyl)(3-(furan-2-yl)-8-phenyl-5,6-dihydro-[1,2,4]triazolo[4,3-a]pyrazin-7(8H)-yl)methanone

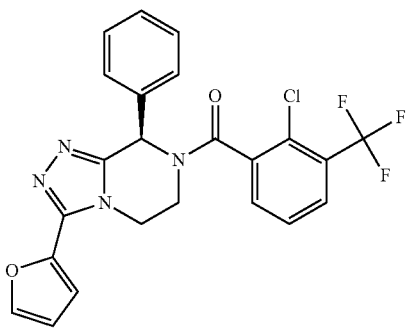 [SMILES: O=C(c1cccc(C(F)(F)F)c1Cl)N1CCn2c(-c3ccco3)nnc2[C@H]1c1ccccc1]

The desired product was prepared in an analogous manner to example 53 (using oxazole-2-carbohydrazide instead of acetic hydrazide in Step F.) The racemic product was separated via chiral SFC (Stationary phase: CHIRALPAK AD-H 5 μm 250×20 mm), (Mobile phase: 68% CO$_2$, 32% iPrOH) yielding the desired product. $^1$H NMR (400 MHz, CDCl$_3$) δ 7.85-7.74 (m, 1H), 7.65-7.30 (m, 8H), 7.21-7.13 (m, 1H), 6.65-6.52 (m, 1H), 6.23-6.04; 5.19-5.05 (m, 1H), 4.61-3.34 (m, 4H). MS (ESI) mass calcd. $C_{23}H_{16}ClF_3N_4O_2$, 472.1; m/z found, 473.1 [M+H]$^+$.

Example 84: (S)-(2-chloro-3-(trifluoromethyl)phenyl)(3-(furan-2-yl)-8-phenyl-5,6-dihydro-[1,2,4]triazolo[4,3-a]pyrazin-7(8H)-yl)methanone

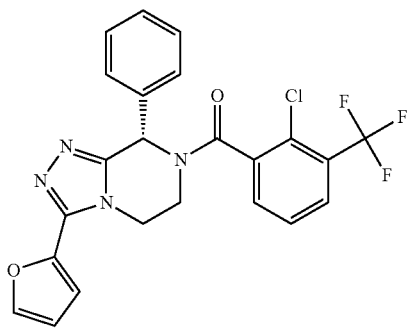 [SMILES: O=C(c1cccc(C(F)(F)F)c1Cl)N1CCn2c(-c3ccco3)nnc2[C@@H]1c1ccccc1]

The desired product was prepared in an analogous manner to example 53 (using oxazole-2-carbohydrazide instead of acetic hydrazide in Step F.) The racemic product was separated via chiral SFC (Stationary phase: CHIRALPAK AD-H 5 μm 250×20 mm), (Mobile phase: 68% $CO_2$, 32% iPrOH) yielding the desired product. $^1$H NMR (400 MHz, CDCl$_3$) δ 7.85-7.75 (m, 1H), 7.64-7.28 (m, 8H), 7.21-7.14 (m, 1H), 6.64-6.57 (m, 1H), 6.20-6.08; 5.21-5.01 (m, 1H), 4.64-3.35 (m, 4H). MS (ESI) mass calcd. $C_{23}H_{16}ClF_3N_4O_2$, 472.1; m/z found, 473.0 [M+H]$^+$.

Example 85: (±)-(2-chloro-3-(trifluoromethyl)phenyl)(3-methyl-8-(pyridin-2-yl)-5,6-dihydro-[1,2,4]triazolo[4,3-a]pyrazin-7(8H)-yl)methanone

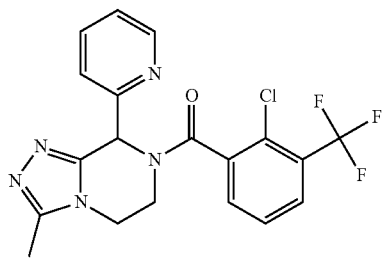 [SMILES: Cc1nnc2n1CCN(C(=O)c1cccc(C(F)(F)F)c1Cl)C2c1ccccn1]

To a solution of 3-methyl-8-(pyridin-2-yl)-5,6,7,8-tetrahydro-[1,2,4]triazolo[4,3-a]pyrazine (200 mg, 0.766 mmol) in 5 mL of DCM was added triethylamine (0.639 mL, 4.596 mmol). The resulting reaction mixture was stirred for 5 min at room temperature and then cooled to 0° C. 2-chloro-3-(trifluoromethyl)benzoyl chloride (372 mg, 1.532 mmol) was subsequently added and the reaction was stirred at 0° C. for 20 min. The reaction was quenched with water and warmed to room temperature then extracted three times with DCM. The combined organic layers were dried using MgSO$_4$ and concentrated into a residue, which was purified via basic HPLC (Agilent prep system, Waters XBridge C18 5 um 50×100 mm column, 5-95% MeCN/20 nM NH$_4$OH over 22 min at 80 mL/min) to provide the racemic product (114 mg, 35.2%). $^1$H NMR (500 MHz, CDCl$_3$) δ 8.68-8.39 (m, 1H), 7.97-7.12 (m, 6H), 5.98-5.90; 5.23-5.09 (m, 1H), 4.47-3.43 (m, 4H), 2.51-2.39 (m, 3H). MS (ESI) mass calcd. $C_{19}H_{15}ClF_3N_5O$, 421.1; m/z found, 422.0 [M+H]$^+$.

Example 86: (R)-(2-chloro-3-(trifluoromethyl)phenyl)(3-ethyl-8-phenyl-5,6-dihydro-[1,2,4]triazolo[4,3-a]pyrazin-7(8H)-yl)methanone

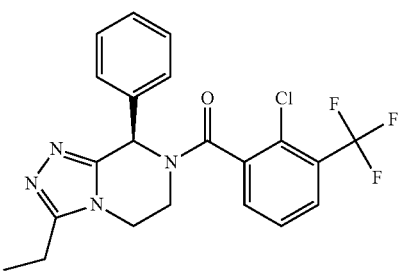 [SMILES: CCc1nnc2n1CCN(C(=O)c1cccc(C(F)(F)F)c1Cl)[C@@H]2c1ccccc1]

The desired product was prepared in an analogous manner to example 53 (using propionohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, CDCl$_3$) δ 7.84-7.73 (m, 1H), 7.58-7.28 (m, 7H), 6.20-6.01; 5.19-5.02 (m, 1H), 4.17-3.30 (m, 4H), 2.89-2.64 (m, 2H), 1.49-1.37 (m, 3H). MS (ESI) mass calcd. $C_{21}H_{18}ClF_3N_4O$, 434.1; m/z found, 435.4 [M+H]$^+$.

Example 87: (S)-(2-chloro-3-(trifluoromethyl)phenyl)(3-ethyl-8-phenyl-5,6-dihydro-[1,2,4]triazolo[4,3-a]pyrazin-7(8H)-yl)methanone

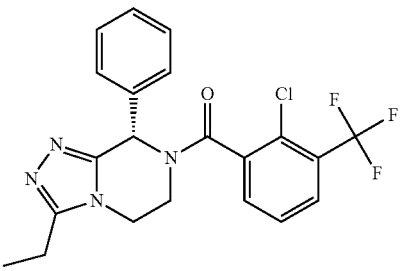 [SMILES: CCc1nnc2n1CCN(C(=O)c1cccc(C(F)(F)F)c1Cl)[C@H]2c1ccccc1]

The desired product was prepared in an analogous manner to example 53 (using propionohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, CDCl$_3$) δ 7.87-7.71 (m, 1H), 7.60-7.27 (m, 7H), 6.20-6.01; 5.19-5.01 (m, 1H), 4.16-3.28 (m, 4H), 2.88-2.67 (m, 2H), 1.48-1.39 (m, 3H). MS (ESI) mass calcd. $C_{21}H_{18}ClF_3N_4O$, 434.1; m/z found, 435.2 [M+H]$^+$.

Example 88: (R)-(2-chloro-3-(trifluoromethyl)phenyl)(3-isopropyl-8-phenyl-5,6-dihydro-[1,2,4]triazolo[4,3-a]pyrazin-7(8H)-yl)methanone

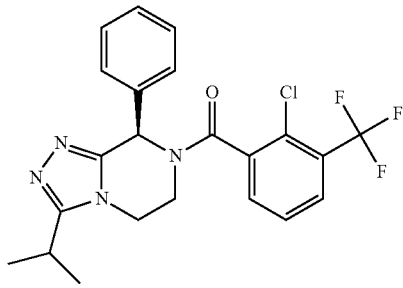 [SMILES: CC(C)c1nnc2n1CCN(C(=O)c1cccc(C(F)(F)F)c1Cl)[C@@H]2c1ccccc1]

The desired product was prepared in an analogous manner to example 53 (using isobutyrohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, $CDCl_3$) δ 7.84-7.74 (m, 1H), 7.58-7.28 (m, 7H), 6.19-6.01; 5.17-5.00 (m, 1H), 4.21-3.30 (m, 4H), 3.08-2.92 (m, 1H), 1.52-1.44 (m, 3H), 1.44-1.37 (m, 3H). MS (ESI) mass calcd. $C_{22}H_{20}ClF_3N_4O$, 448.1; m/z found, 449.3 $[M+H]^+$.

Example 89: (S)-(2-chloro-3-(trifluoromethyl)phenyl)(3-isopropyl-8-phenyl-5,6-dihydro-[1,2,4]triazolo[4,3-a]pyrazin-7(8H)-yl)methanone

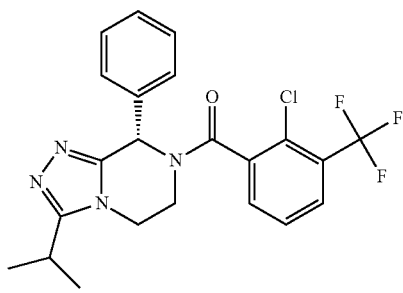 [SMILES: CC(C)c1nnc2n1CCN(C(=O)c1cccc(C(F)(F)F)c1Cl)[C@H]2c1ccccc1]

The desired product was prepared in an analogous manner to example 53 (using isobutyrohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, $CDCl_3$) δ 7.84-7.73 (m, 1H), 7.58-7.27 (m, 7H), 6.19-6.01; 5.19-5.02 (m, 1H), 4.20-3.28 (m, 4H), 3.09-2.92 (m, 1H), 1.51-1.44 (m, 3H), 1.43-1.37 (m, 3H). MS (ESI) mass calcd. $C_{22}H_{20}ClF_3N_4O$, 448.1; m/z found, 449.4 $[M+H]^+$.

Example 90: (±)-(2,3-dichlorophenyl)(8-phenyl-3-(trifluoromethyl)-5,6-dihydro-[1,2,4]triazolo[4,3-a]pyrazin-7(8H)-yl)methanone

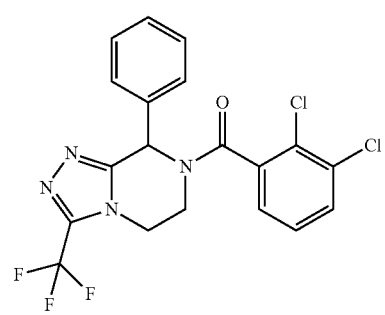 [SMILES: O=C(c1cccc(Cl)c1Cl)N1CCn2c(nnc2C(F)(F)F)C1c1ccccc1]

The desired product was prepared in an analogous manner to example 108 (using trifluoroacetic anhydride instead of difluoroacetic anhydride in Step C and 2,3-dichlorobenzoyl chloride instead of 2-chloro-3-(trifluoromethyl)benzoyl chloride in Step E) and was purified via basic HPLC (Agilent prep system, Waters XBridge C18 5 μm 50×100 mm column, 5-95% MeCN/20 nM $NH_4OH$ over 22 min at 80 mL/min) to provide the racemic product (100 mg, 55%). $^1$H NMR (500 MHz, $CDCl_3$) δ 7.61-7.52 (m, 12H), 7.52-7.17 (m, 7H), 6.34-6.11; 5.20-5.05 (m, 1H), 4.40-3.32 (m, 4H). MS (ESI) mass calcd. $C_{19}H_{13}Cl_2F_3N_4O$, 440.1; m/z found, 441.1 $[M+H]^+$.

Example 91: (R)-(2-chloro-3-(trifluoromethyl)phenyl)(3-methyl-8-(pyridin-2-yl)-5,6-dihydro-[1,2,4]triazolo[4,3-a]pyrazin-7(8H)-yl)methanone

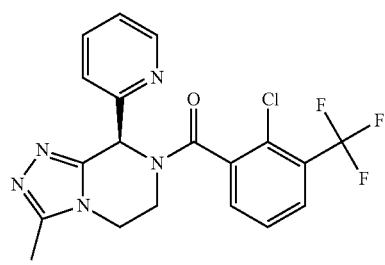 [SMILES: Cc1nnc2n1CCN(C(=O)c1cccc(C(F)(F)F)c1Cl)[C@@H]2c1ccccn1]

The desired product was prepared in an analogous manner to example 85. The racemic product was separated via chiral SFC (Stationary phase: CHIRALPAK AD-H 5 μm 250×20 mm), (Mobile phase: 60% $CO_2$, 40% iPrOH) yielding the desired product. $^1$H NMR (400 MHz, $CDCl_3$) δ 8.63-8.44 (m, 1H), 7.97-7.13 (m, 6H), 5.99-5.91; 5.26-5.10 (m, 1H), 4.50-3.52 (m, 4H), 2.51-2.43 (m, 3H). MS (ESI) mass calcd. $C_{19}H_{15}ClF_3N_5O$, 421.1; m/z found, 421.8 $[M+H]^+$.

Example 92: (S)-(2-chloro-3-(trifluoromethyl)phenyl)(3-methyl-8-(pyridin-2-yl)-5,6-dihydro-[1,2,4]triazolo[4,3-a]pyrazin-7(8H)-yl)methanone

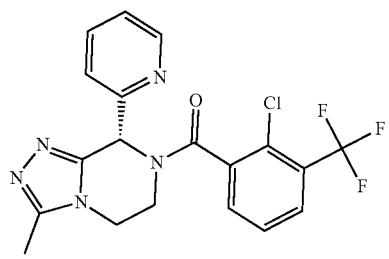 [SMILES: Cc1nnc2n1CCN(C(=O)c1cccc(C(F)(F)F)c1Cl)[C@H]2c1ccccn1]

The desired product was prepared in an analogous manner to example 85. The racemic product was separated via chiral SFC (Stationary phase: CHIRALPAK AD-H 5 μm 250×20 mm), (Mobile phase: 60% $CO_2$, 40% iPrOH) yielding the desired product. $^1$H NMR (400 MHz, $CDCl_3$) δ 8.63-8.44 (m, 1H), 7.97-7.14 (m, 6H), 5.99-5.94; 5.24-5.10 (m, 1H), 4.49-3.53 (m, 4H), 2.52-2.41 (m, 3H). MS (ESI) mass calcd. $C_{19}H_{15}ClF_3N_5O$, 421.1; m/z found, 421.8 [M+H]$^+$.

Example 93: (R)-(2-chloro-3-(trifluoromethyl)phenyl)(3-cyclobutyl-8-phenyl-5,6-dihydro-[1,2,4]triazolo[4,3-a]pyrazin-7(8H)-yl)methanone

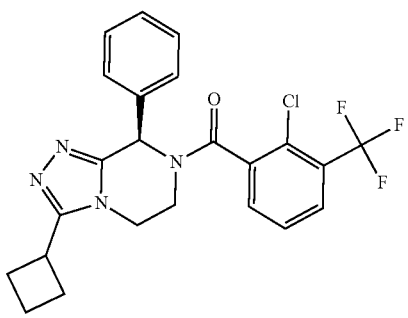 [SMILES: O=C(c1cccc(C(F)(F)F)c1Cl)N1CCn2c(C3CCC3)nnc2[C@H]1c1ccccc1]

The desired product was prepared in an analogous manner to example 53 (using cyclobutanecarbohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (500 MHz, $CDCl_3$) δ 7.83-7.74 (m, 1H), 7.56-7.28 (m, 7H), 6.18-5.97; 5.13-4.98 (m, 1H), 4.08-3.27 (m, 5H), 2.66-2.49 (m, 2H), 2.50-2.34 (m, 2H), 2.21-2.00 (m, 2H). MS (ESI) mass calcd. $C_{23}H_{20}ClF_3N_4O$, 460.1; m/z found, 461.1 [M+H]$^+$.

Example 94: (S)-(2-chloro-3-(trifluoromethyl)phenyl)(3-cyclobutyl-8-phenyl-5,6-dihydro-[1,2,4]triazolo[4,3-a]pyrazin-7(8H)-yl)methanone

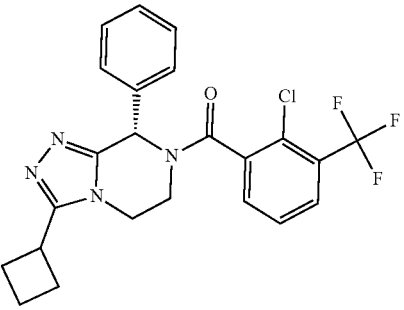 [SMILES: O=C(c1cccc(C(F)(F)F)c1Cl)N1CCn2c(C3CCC3)nnc2[C@@H]1c1ccccc1]

The desired product was prepared in an analogous manner to example 53 (using cyclobutanecarbohydrazide instead of acetic hydrazide in Step F.) The racemic product was separated via chiral SFC (Stationary phase: CHIRALPAK AD-H 5 μm 250×20 mm), (Mobile phase: 70% $CO_2$, 30% iPrOH) yielding the desired product. $^1$H NMR (500 MHz, $CDCl_3$) δ 7.83-7.73 (m, 1H), 7.56-7.28 (m, 7H), 6.16-5.98; 5.13-4.98 (m, 1H), 4.08-3.24 (m, 5H), 2.68-2.49 (m, 2H), 2.49-2.34 (m, 2H), 2.23-2.00 (m, 2H). MS (ESI) mass calcd. $C_{23}H_{20}ClF_3N_4O$, 460.1; m/z found, 461.1 [M+H]$^+$.

Examples 95 and 96 were prepared as described in Example 108, substituting trifluoroacetic anhydride for difluoroacetic anhydride in Step C and 2-chloro-4-fluoro-3-trifluoromethyl benzoic acid for 2-chloro-3-(trifluoromethyl)benzoic acid in Step E. The racemic mixture was separated by prep HPLC (Stationary phase: CHIRALPAK AD-H 5 μm 250×20 mm), Mobile phase: 80% $CO_2$, 20% EtOH) to provide the (R) and (5) enantiomers.

Example 95: (R*)-(2-chloro-4-fluoro-3-(trifluoromethyl)phenyl)(8-phenyl-3-(trifluoromethyl)-5,6-dihydro-[1,2,4]triazolo[4,3-a]pyrazin-7(8H)-yl)methanone

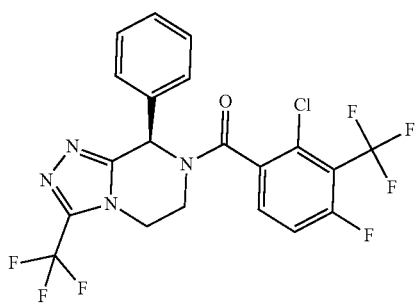 [SMILES: O=C(c1ccc(F)c(C(F)(F)F)c1Cl)N1CCn2c(nnc2C(F)(F)F)[C@H]1c1ccccc1]

$^1$H NMR (500 MHz, $CDCl_3$) δ 7.60-7.13 (m, 7H), 6.21-6.23; 6.10-6.04; 5.20-5.07 (m, 1H), 4.38-4.15; 4.02-3.88; 3.78-3.38 (m, 4H). MS (ESI) mass calcd. $C_{20}H_{12}ClF_7N_4O$, 492.1; m/z found, 492.0.

Example 96: (S*)-(2-chloro-4-fluoro-3-(trifluoromethyl)phenyl)(8-phenyl-3-(trifluoromethyl)-5,6-dihydro-[1,2,4]triazolo[4,3-a]pyrazin-7(8H)-yl)methanone

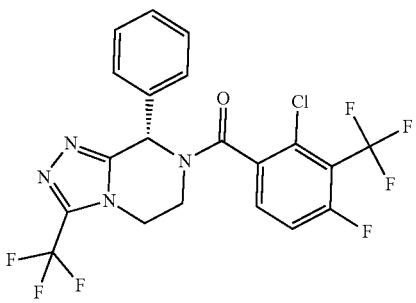 [SMILES: O=C(c1ccc(F)c(C(F)(F)F)c1Cl)N1CCn2c(nnc2C(F)(F)F)[C@@H]1c1ccccc1]

¹H NMR (500 MHz, CDCl₃) δ 7.60-7.13 (m, 7H), 6.21-6.23; 6.10-6.04; 5.20-5.07 (m, 1H), 4.38-4.15; 4.02-3.88; 3.78-3.38 (m, 4H). MS (ESI) mass calcd. C₂₀H₁₂ClF₇N₄O, 492.1; m/z found, 492.0.

Example 97: (R)-(2-chloro-3-(trifluoromethyl)phenyl)(8-phenyl-3-(trifluoromethyl)-5,6-dihydro-[1,2,4]triazolo[4,3-a]pyrazin-7(8H)-yl)methanone

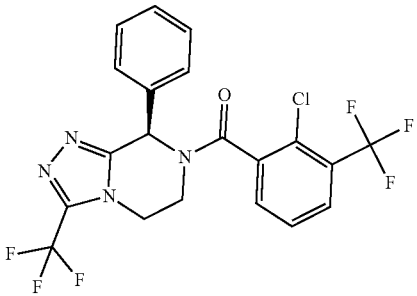 [SMILES: O=C(c1cccc(C(F)(F)F)c1Cl)N1CCn2c(nnc2C(F)(F)F)[C@H]1c1ccccc1]

The desired product was prepared in an analogous manner to example 108 (using trifluoracetic anhydride instead of difluoroacetic anhydride in Step C) and was separated via chiral SFC (Stationary phase: CHIRALPAK AD-H 5 μm 250×20 mm), (Mobile phase: 80% CO₂, 20% iPrOH) yielding the desired product. ¹H NMR (400 MHz, CDCl₃) δ 7.86-7.77 (m, 1H), 7.60-7.32 (m, 7H), 6.26-6.08; 5.23-5.09 (m, 1H), 4.40-3.36 (m, 4H). MS (ESI) mass calcd. C₂₀H₁₃ClF₆N₄O, 474.1; m/z found, 474.7 [M+H]⁺.

Example 98: (S)-(2-chloro-3-(trifluoromethyl)phenyl)(8-phenyl-3-(trifluoromethyl)-5,6-dihydro-[1,2,4]triazolo[4,3-a]pyrazin-7(8H)-yl)methanone

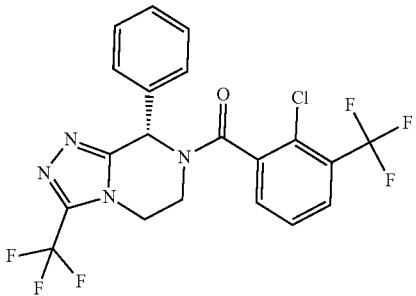 [SMILES: O=C(c1cccc(C(F)(F)F)c1Cl)N1CCn2c(nnc2C(F)(F)F)[C@@H]1c1ccccc1]

The desired product was separated from example 97 via chiral SFC (Stationary phase: CHIRALPAK AD-H 5 μm 250×20 mm), (Mobile phase: 80% CO₂, 20% iPrOH) yielding the desired product. ¹H NMR (400 MHz, CDCl₃) δ 7.86-7.76 (m, 1H), 7.60-7.31 (m, 7H), 6.26-6.07; 5.23-5.09 (m, 1H), 4.41-3.36 (m, 4H). MS (ESI) mass calcd. C₂₀H₁₃ClF₆N₄O, 474.1; m/z found, 474.8 [M+H]⁺.

Examples 99 and 100 were prepared as described in Example 108, substituting trifluoracetic anhydride for difluoroacetic anhydride in Step C and 3-chloro-2-(trifluoromethyl)isonicotinic acid for 2-chloro-3-(trifluoromethyl)benzoic acid in Step E. The racemic mixture was separated by prep HPLC (Stationary phase: CHIRALPAK AD-H 5 μm 250×20 mm), Mobile phase: 80% CO₂, 20% EtOH) to provide the (R) and (S) enantiomers.

Example 99: (R*)-(3-chloro-2-(trifluoromethyl)pyridin-4-yl)(8-phenyl-3-(trifluoromethyl)-5,6-dihydro-[1,2,4]triazolo[4,3-a]pyrazin-7(8H)-yl)methanone

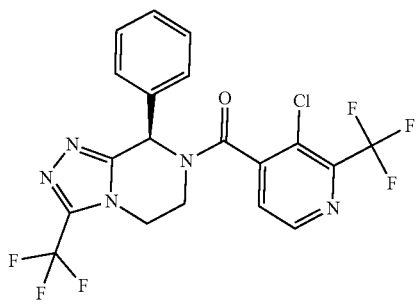 [SMILES: O=C(c1ccnc(C(F)(F)F)c1Cl)N1CCn2c(nnc2C(F)(F)F)[C@H]1c1ccccc1]

¹H NMR (500 MHz, CDCl₃) δ 8.78-8.59 (m, 1H), 7.61-7.20 (m, 6H), 6.20-6.12; 6.04-5.92; 5.21-5.06 (m, 1H), 4.42-4.16; 4.07-3.93; 3.81-3.41 (m, 4H). MS (ESI) mass calcd. C₁₉H₁₂ClF₆N₅O, 475.1; m/z found, 475.9 [M+H]⁺.

Example 100 (S*)-(3-chloro-2-(trifluoromethyl)pyridin-4-yl)(8-phenyl-3-(trifluoromethyl)-5,6-dihydro-[1,2,4]triazolo[4,3-a]pyrazin-7(8H)-yl)methanone

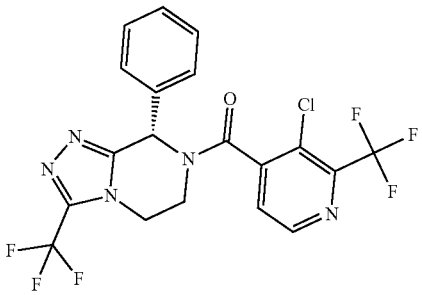 [SMILES: O=C(c1ccnc(C(F)(F)F)c1Cl)N1CCn2c(nnc2C(F)(F)F)[C@@H]1c1ccccc1]

¹H NMR (500 MHz, CDCl₃) δ 8.78-8.59 (m, 1H), 7.61-7.20 (m, 6H), 6.20-6.12; 6.04-5.92; 5.21-5.06 (m, 1H), 4.42-4.16; 4.07-3.93; 3.81-3.41 (m, 4H). MS (ESI) mass calcd. C₁₉H₁₂ClF₆N₅O, 475.1; m/z found, 475.9 [M+H]⁺.

Example 101: (±)-(2-chloro-3-(trifluoromethyl)phenyl)(8-(4-fluorophenyl)-3-methyl-5,6-dihydro-[1,2,4]triazolo[4,3-a]pyrazin-7(8H)-yl)methanone

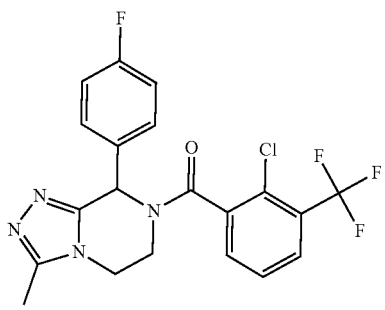 [SMILES: Cc1nnc2n1CCN(C(=O)c1cccc(C(F)(F)F)c1Cl)C2c1ccc(F)cc1]

To a solution of 8-(4-fluorophenyl)-3-methyl-5,6,7,8-tetrahydro-[1,2,4]triazolo[4,3-a]pyrazine (120 mg, 0.435 mmol) in 5 mL of DCM was added triethylamine (0.363 mL, 2.610 mmol). The resulting reaction mixture was stirred for 5 min at room temperature and then cooled to 0° C. 2-chloro-3-(trifluoromethyl)benzoyl chloride (211 mg, 0.870 mmol) was subsequently added and the reaction was stirred at 0° C. for 20 min. The reaction was quenched with water and warmed to room temperature then extracted three times with DCM. The combined organic layers were dried using MgSO$_4$ and concentrated into a residue, which was purified via basic HPLC (Agilent prep system, Waters XBridge C18 5 um 50×100 mm column, 5-95% MeCN/20 nM NH$_4$OH over 22 min at 80 mL/min) to provide the racemic product (124 mg, 65%). $^1$H NMR (500 MHz, CDCl$_3$) δ 7.85-7.75 (m, 1H), 7.61-7.33 (m, 4H), 7.10-6.99 (m, 2H), 6.12-5.92; 5.19-5.04 (m, 1H), 4.14-3.27 (m, 4H), 2.51-2.41 (m, 3H). MS (ESI) mass calcd. C$_{20}$H$_{15}$ClF$_4$N$_4$O, 438.1; m/z found, 439.2 [M+H]$^+$.

Example 102: (R)-(2,3-dichlorophenyl)(8-phenyl-3-(trifluoromethyl)-5,6-dihydro-[1,2,4]triazolo[4,3-a]pyrazin-7(8H)-yl)methanone

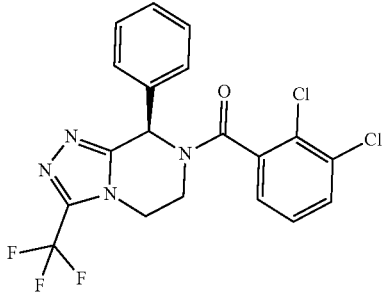 [SMILES: O=C(c1cccc(Cl)c1Cl)N1CCn2c(nnc2C(F)(F)F)[C@H]1c1ccccc1]

The desired product was prepared in an analogous manner to example 108 (using trifluoracetic anhydride instead of difluoroacetic anhydride in Step C and 2,3-dichlorobenzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 75% CO$_2$, 25% iPrOH) yielding the desired product. $^1$H NMR (400 MHz, CDCl$_3$) δ 7.61-7.52 (m, 1H), 7.52-7.19 (m, 7H), 6.34-6.11; 5.19-5.08 (m, 1H), 4.40-3.32 (m, 4H). MS (ESI) mass calcd. C$_{19}$H$_{13}$Cl$_2$F$_3$N$_4$O, 440.0; m/z found, 440.8 [M+H]$^+$.

Example 103: (S)-(2,3-dichlorophenyl)(8-phenyl-3-(trifluoromethyl)-5,6-dihydro-[1,2,4]triazolo[4,3-a]pyrazin-7(8H)-yl)methanone

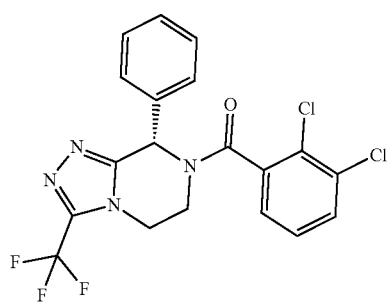 [SMILES: O=C(c1cccc(Cl)c1Cl)N1CCn2c(nnc2C(F)(F)F)[C@@H]1c1ccccc1]

The desired product was separated from example 102 via chiral SFC (Stationary phase: CHIRALPAK AD-H 5 μm 250×20 mm), (Mobile phase: 75% CO$_2$, 25% iPrOH) yielding the desired product. $^1$H NMR (400 MHz, CDCl$_3$) δ 7.61-7.53 (m, 1H), 7.53-7.19 (m, 7H), 6.33-6.12; 5.19-5.08 (m, 1H), 4.40-3.31 (m, 4H). MS (ESI) mass calcd. C$_{19}$H$_{13}$Cl$_2$F$_3$N$_4$O, 440.0; m/z found, 440.8 [M+H]$^+$.

Example 104: (R)-(2,3-dichlorophenyl)(8-(4-fluorophenyl)-3-methyl-5,6-dihydro-[1,2,4]triazolo[4,3-a]pyrazin-7(8H)-yl)methanone

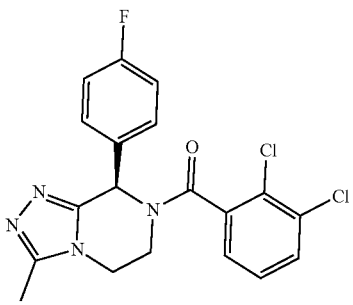 [SMILES: Cc1nnc2n1CCN(C(=O)c1cccc(Cl)c1Cl)[C@@H]2c1ccc(F)cc1]

The desired product was prepared in an analogous manner to example 101 (using 2,3-dichlorobenzoyl chloride instead of 2-chloro-3-(trifluoromethyl)benzoyl chloride.) The racemic product was separated via chiral SFC (Stationary phase: CHIRALPAK AD-H 5 μm 250×20 mm), (Mobile phase: 75% CO$_2$, 25% iPrOH) yielding the desired product. $^1$H NMR (400 MHz, CDCl$_3$) δ 7.60-7.51 (m, 1H), 7.47-7.15 (m, 4H), 7.10-6.98 (m, 2H), 6.20-5.98; 5.20-5.02 (m, 1H), 4.14-3.23 (m, 4H), 2.53-2.40 (m, 3H). MS (ESI) mass calcd. C$_{19}$H$_{15}$Cl$_2$FN$_4$O, 404.1; m/z found, 404.8 [M+H]$^+$.

Example 105: (S)-(2,3-dichlorophenyl)(8-(4-fluorophenyl)-3-methyl-5,6-dihydro-[1,2,4]triazolo[4,3-a]pyrazin-7(8H)-yl)methanone

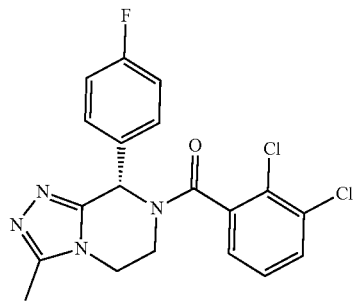 [SMILES: Cc1nnc2n1CCN(C(=O)c1cccc(Cl)c1Cl)[C@H]2c1ccc(F)cc1]

The desired product was prepared in an analogous manner to example 101 (using 2,3-dichlorobenzoyl chloride instead of 2-chloro-3-(trifluoromethyl)benzoyl chloride.) The racemic product was separated via chiral SFC (Stationary phase: CHIRALPAK AD-H 5 µm 250×20 mm), (Mobile phase: 75% $CO_2$, 25% iPrOH) yielding the desired product. $^1$H NMR (400 MHz, $CDCl_3$) δ 7.60-7.50 (m, 1H), 7.47-7.16 (m, 4H), 7.10-6.98 (m, 2H), 6.20-5.99; 5.18-5.03 (m, 1H), 4.16-3.21 (m, 4H), 2.53-2.44 (m, 3H). MS (ESI) mass calcd. $C_{19}H_{15}Cl_2FN_4O$, 404.1; m/z found, 404.7 $[M+H]^+$.

Example 106: (R)-(2-chloro-3-(trifluoromethyl)phenyl)(3-cyclopropyl-8-(4-fluorophenyl)-5,6-dihydro-[1,2,4]triazolo[4,3-a]pyrazin-7(8H)-yl)methanone

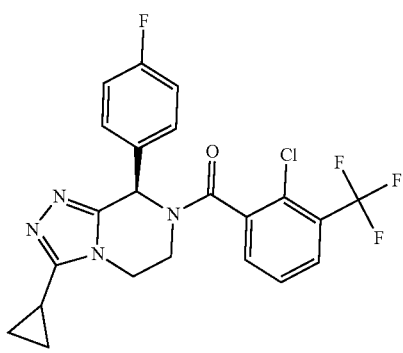 [SMILES: O=C(c1cccc(C(F)(F)F)c1Cl)N1CCn2c(C3CC3)nnc2[C@H]1c1ccc(F)cc1]

The desired product was prepared in an analogous manner to example 101 (using 3-cyclopropyl-8-(4-fluorophenyl)-5,6,7,8-tetrahydro-[1,2,4]triazolo[4,3-a]pyrazine instead of 8-(4-fluorophenyl)-3-methyl-5,6,7,8-tetrahydro-[1,2,4]triazolo[4,3-a]pyrazine.) The racemic product was separated via chiral SFC (Stationary phase: CHIRALPAK AD-H 5 µm 250×20 mm), (Mobile phase: 75% $CO_2$, 25% iPrOH) yielding the desired product. $^1$H NMR (400 MHz, $CDCl_3$) δ 7.86-7.75 (m, 1H), 7.59-7.27 (m, 4H), 7.11-6.98 (m, 2H), 6.13-5.92; 5.20-5.05 (m, 1H), 4.25-3.27 (m, 4H), 1.79-1.65 (m, 1H), 1.29-1.17 (m, 2H), 1.16-1.04 (m, 2H). MS (ESI) mass calcd. $C_{22}H_{17}ClF_4N_4O$, 464.1; m/z found, 464.8 $[M+H]^+$.

Example 107: (S)-(2-chloro-3-(trifluoromethyl)phenyl)(3-cyclopropyl-8-(4-fluorophenyl)-5,6-dihydro-[1,2,4]triazolo[4,3-a]pyrazin-7(8H)-yl)methanone

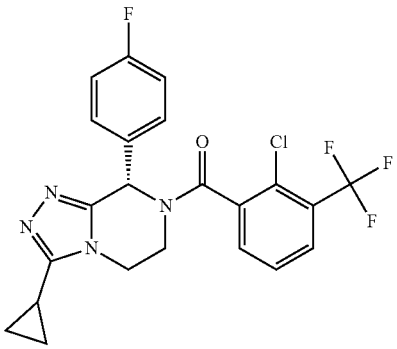 [SMILES: O=C(c1cccc(C(F)(F)F)c1Cl)N1CCn2c(C3CC3)nnc2[C@@H]1c1ccc(F)cc1]

The desired product was prepared in an analogous manner to example 101 (using 3-cyclopropyl-8-(4-fluorophenyl)-5,6,7,8-tetrahydro-[1,2,4]triazolo[4,3-a]pyrazine instead of 8-(4-fluorophenyl)-3-methyl-5,6,7,8-tetrahydro-[1,2,4]triazolo[4,3-a]pyrazine.) The racemic product was separated via chiral SFC (Stationary phase: CHIRALPAK AD-H 5 µm 250×20 mm), (Mobile phase: 75% $CO_2$, 25% iPrOH) yielding the desired product. $^1$H NMR (400 MHz, $CDCl_3$) δ 7.86-7.75 (m, 1H), 7.60-7.27 (m, 4H), 7.11-6.98 (m, 2H), 6.12-5.92; 5.22-5.05 (m, 1H), 4.25-3.25 (m, 4H), 1.81-1.65 (m, 1H), 1.33-1.17 (m, 2H), 1.17-1.02 (m, 2H). MS (ESI) mass calcd. $C_{22}H_{17}ClF_4N_4O$, 464.1; m/z found, 464.8 $[M+H]^+$.

Example 108: (R)-(2-chloro-3-(trifluoromethyl)phenyl)(3-(difluoromethyl)-8-phenyl-5,6-dihydro-[1,2,4]triazolo[4,3-a]pyrazin-7(8H)-yl)methanone

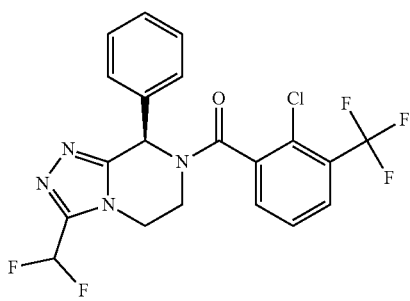

Intermediate 108A: 2-chloro-3-phenylpyrazine

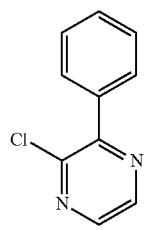 [SMILES: Clc1nccnc1-c1ccccc1]

Step A: 2-chloro-3-phenylpyrazine. To a solution of 2,3-dichloropyrazine (1.50 g, 10.07 mmol) and phenylboronic acid (1.23 g, 10.07 mmol) in 35 mL of DME was added Na$_2$CO$_3$ (1.07 g, 10.07 mmol) in 15 mL of water. N2 gas was bubbled through the reaction mixture for 15 min then the flask was equipped with a condenser and purged with N$_2$ for another 15 in before adding tetrakis(triphenylphosphine)palladium (581.75 mg, 0.503 mmol). The resulting reaction mixture was heated to reflux (85° C.) and allowed to stir overnight. The reaction was cooled to rt and diluted with 80 mL of water then extracted three times with DCM. The combined organic extracts were dried with MgSO$_4$, filtered and concentrated under reduced pressure. The resulting yellow residue was purified via silica gel chromatography (0-30% ethyl acetate/hexanes) to provide the desired product (1.39 g, 72%) as a white solid. MS (ESI) mass calcd. C$_{10}$H$_7$ClN$_2$, 190.63; m/z found, 191.0 [M+H]$^+$.

Intermediate 108B: 2-hydrazinyl-3-phenylpyrazine

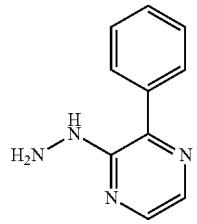 [SMILES: NNc1nccnc1-c1ccccc1]

Step B: 2-hydrazinyl-3-phenylpyrazine. A neat suspension of 2-chloro-3-phenylpyrazine (1.39 g, 7.23 mmol) in hydrazine monohydrate (3.6 mL, 72.78 mmol) was placed in microwave vial and irradiates at 120° C. for 1 hour. The resulting reaction mixture was cooled down to rt and diluted with 30 mL of water and then extracted three times with 30 mL of DCM. The combined organic extracts were dried using MgSO$_4$ and concentrated under reduced pressure to provide the desired product (1.21 g, 89%). MS (ESI) mass calcd. C$_{10}$H$_{10}$N$_4$, 186.2; m/z found, 187.2 [M+H]$^+$.

Intermediate 108C: 3-(difluoromethyl)-8-phenyl-[1,2,4]triazolo[4,3-a]pyrazine

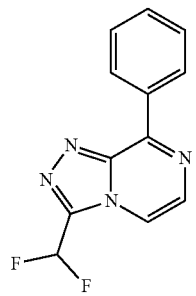 [SMILES: FC(F)c1nnc2c(-c3ccccc3)nccn12]

Step C: 3-(difluoromethyl)-8-phenyl-[1,2,4]triazolo[4,3-a]pyrazine. A neat residue of 2-hydrazinyl-3-phenylpyrazine (665 mg, 3.571 mmol) was cooled to 0° C. and Difluoroacetic anhydride (4.44 mL, 35.71 mmol) was added dropwise. The resulting reaction mixture was allowed to stir at room temperature for 2 hours then concentrated into a brown residue under reduced pressure. The brown residue was suspended in 4 mL of polyphosphoric acid to form a gelatinous mixture, which was heated to 140° C. and stirred overnight The reaction mixture was then neutralized to pH 7 with NaOH pellets and ice water. The resulting aqueous solution was extracted three times with ethyl acetate. The combined organic extracts were dried with MgSO$_4$ and concentrated into a brown residue which was purified via silica gel chromatography (0-50% ethyl acetate/hexanes) to provide the desired product (500 mg, 57%). $^1$H NMR (500 MHz, CDCl$_3$) δ 8.84-8.77 (m, 2H), 8.20 (d, J=4.6 Hz, 1H), 8.12 (d, J=4.6 Hz, 1H), 7.60-7.53 (m, 3H), 7.45-7.22 (m, 1H). MS (ESI) mass calcd. C$_{12}$H$_8$F$_2$N$_4$, 246.2; m/z found, 274.1 [M+H]$^+$.

Intermediate 108D: 3-(difluoromethyl)-8-phenyl-5,6,7,8-tetrahydro-[1,2,4]triazolo[4,3-a]pyrazine

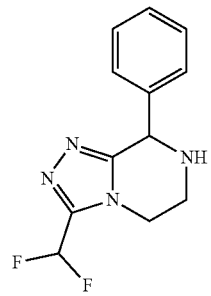 [SMILES: FC(F)c1nnc2n1CCNC2c1ccccc1]

Step D: 3-(difluoromethyl)-8-phenyl-5,6,7,8-tetrahydro-[1,2,4]triazolo[4,3-a]pyrazine. To a round-bottom flask containing a solution of 3-(difluoromethyl)-8-phenyl-[1,2,4]triazolo[4,3-a]pyrazine (500 mg, 2.031 mmol) in 5 mL ethanol was added 10% palladium on carbon (wet Degussa powder) (108 mg, 0.102 mmol). The resulting reaction vessel was purged with N$_2$ gas and fitted with a hydrogen balloon (1 atm), then the reaction mixture was stirred at rt overnight. The reaction mixture was then filtered through a pad of celite and concentrated under reduced pressure to provide the desired product (470 mg, 92%). MS (ESI) mass calcd. C$_{12}$H$_{12}$F$_2$N$_4$, 250.2; m/z found, 251.1 [M+H]$^+$.

Example 108: (R)-(2-chloro-3-(trifluoromethyl)phenyl)(3-(difluoromethyl)-8-phenyl-5,6-dihydro-[1,2,4]triazolo[4,3-a]pyrazin-7(8H)-yl)methanone

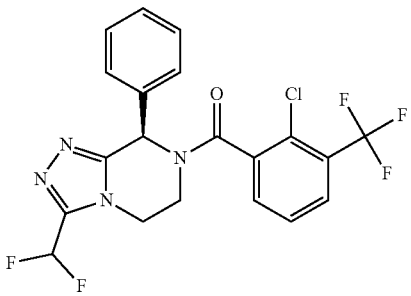 [SMILES: O=C(c1cccc(C(F)(F)F)c1Cl)N1CCn2c(C(F)F)nnc2[C@H]1c1ccccc1]

Step E: (R)-(2-chloro-3-(trifluoromethyl)phenyl)(3-(difluoromethyl)-8-phenyl-5,6-dihydro-[1,2,4]triazolo[4,3-a]pyrazin-7(8H)-yl)methanone. To a solution of 3-(difluoromethyl)-8-phenyl-5,6,7,8-tetrahydro-[1,2,4]triazolo[4,3-a]

pyrazine (150 mg, 0.600 mmol) in 5 mL of DCM was added triethylamine (0.25 mL, 1.798 mmol). The resulting reaction mixture was stirred for 5 min at room temperature and then cooled to 0° C. 2-chloro-3-(trifluoromethyl)benzoyl chloride (291 mg, 1.200 mmol) was subsequently added and the reaction was stirred at 0° C. for 20 min. The reaction was quenched with water and warmed to room temperature then extracted three times with DCM. The combined organic layers were dried using MgSO$_4$ and concentrated into a residue, which was purified via basic HPLC (Agilent prep system, Waters XBridge C18 5 µm 50×100 mm column, 5-95% MeCN/20 nM NH$_4$OH over 22 min at 80 mL/min) to provide the racemic product (132 mg, 48.2%). The racemic product was separated via chiral SFC (Stationary phase: CHIRALPAK AD-H 5 µm 250×20 mm), (Mobile phase: 70% CO$_2$, 30% iPrOH) yielding the desired product. $^1$H NMR (400 MHz, CDCl$_3$) δ 7.87-7.77 (m, 1H), 7.61-7.32 (m, 7H), 7.14-6.84 (m, 1H), 6.29-6.08; 5.17-5.10 (m, 1H), 4.43-3.27 (m, 4H). MS (ESI) mass calcd. C$_{20}$H$_{14}$ClF$_5$N$_4$O, 456.1; m/z found, 456.8 [M+H]$^+$.

Example 109: (S)-(2-chloro-3-(trifluoromethyl)phenyl)(3-(difluoromethyl)-8-phenyl-5,6-dihydro-[1,2,4]triazolo[4,3-a]pyrazin-7(8H)-yl)methanone

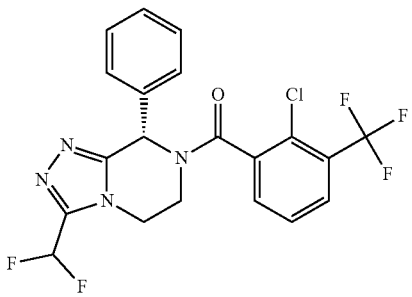 [SMILES: O=C(c1cccc(C(F)(F)F)c1Cl)N1CCn2c(C(F)F)nnc2[C@@H]1c1ccccc1]

The desired product was separated from example 108 via chiral SFC (Stationary phase: CHIRALPAK AD-H 5 µm 250×20 mm), (Mobile phase: 70% CO$_2$, 30% iPrOH) yielding the desired product. $^1$H NMR (400 MHz, CDCl$_3$) δ 7.87-7.76 (m, 1H), 7.60-7.30 (m, 7H), 7.14-6.84 (m, 1H), 6:30-6.09; 5.17-5.07 (m, 1H), 4.44-3.31 (m, 4H). MS (ESI) mass calcd. C$_{20}$H$_{14}$ClF$_5$N$_4$O, 456.1; m/z found, 456.8 [M+H]$^+$.

Example 110: (R)-(2,3-dichlorophenyl)(3-(difluoromethyl)-8-phenyl-5,6-dihydro-[1,2,4]triazolo[4,3-a]pyrazin-7(8H)-yl)methanone

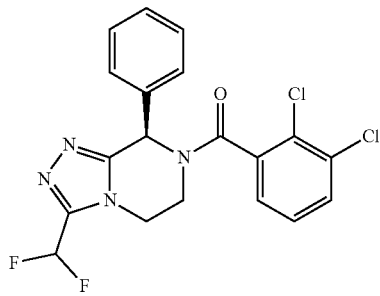 [SMILES: O=C(c1cccc(Cl)c1Cl)N1CCn2c(C(F)F)nnc2[C@H]1c1ccccc1]

The desired product was prepared in an analogous manner to example 108 (using 2,3-dichlorobenzoyl chloride instead of 2-chloro-3-(trifluoromethyl)benzoyl chloride in Step E) and was separated via chiral SFC (Stationary phase: CHIRALPAK AD-H 5 µm 250×20 mm), (Mobile phase: 70% CO$_2$, 30% iPrOH) yielding the desired product. $^1$H NMR (400 MHz, CDCl$_3$) δ 7.61-7.51 (m, 1H), 7.49-7.18 (m, 7H), 7.14-6.84 (m, 1H), 6.30-6.09; 5.15-5.08 (m, 1H), 4.44-3.28 (m, 4H). MS (ESI) mass calcd. C$_{19}$H$_{14}$Cl$_2$F$_2$N$_4$O, 422.1; m/z found, 422.8 [M+H]$^+$.

Example 111: (S)-(2,3-dichlorophenyl)(3-(difluoromethyl)-8-phenyl-5,6-dihydro-[1,2,4]triazolo[4,3-a]pyrazin-7(8H)-yl)methanone

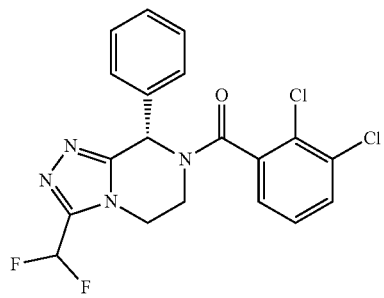 [SMILES: O=C(c1cccc(Cl)c1Cl)N1CCn2c(C(F)F)nnc2[C@@H]1c1ccccc1]

The desired product was separated from example 110 via chiral SFC (Stationary phase: CHIRALPAK AD-H 5 µm 250×20 mm), (Mobile phase: 70% CO$_2$, 30% iPrOH) yielding the desired product. $^1$H NMR (400 MHz, CDCl$_3$) δ 7.61-7.51 (m, 1H), 7.50-7.18 (m, 7H), 7.14-6.84 (m, 1H), 6:30-6.09; 5.17-5.07 (m, 1H), 4.44-3.31 (m, 4H). MS (ESI) mass calcd. C$_{19}$H$_{14}$Cl$_2$F$_2$N$_4$O, 422.1; m/z found, 422.8 [M+H]$^+$.

Example 112: (R)-(2,3-dichlorophenyl)(3-methyl-8-(pyridin-2-yl)-5,6-dihydro-[1,2,4]triazolo[4,3-a]pyrazin-7(8H)-yl)methanone

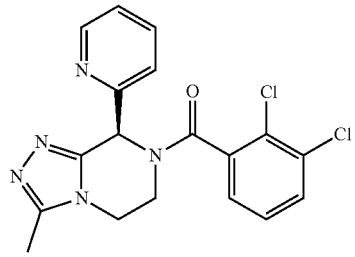 [SMILES: Cc1nnc2n1CCN(C(=O)c1cccc(Cl)c1Cl)[C@@H]2c1ccccn1]

The desired product was prepared in an analogous manner to example 85 (using 2,3-dichlorobenzoyl chloride instead of 2-chloro-3-(trifluoromethyl)benzoyl chloride.) The racemic product was separated via chiral SFC (Stationary phase: CHIRALPAK AD-H 5 µm 250×20 mm), (Mobile phase: 75% CO$_2$, 25% iPrOH) yielding the desired product. $^1$H NMR (400 MHz, CDCl$_3$) δ 8.62-8.43 (m, 1H), 7.96-7.09 (m, 6H), 6.10-5.94; 5.20-5.07 (m, 1H), 4.45-3.57 (m, 4H), 2.52-2.39 (m, 3H). MS (ESI) mass calcd. C$_{18}$H$_{15}$Cl$_2$N$_5$O, 387.1; m/z found, 387.7 [M+H]$^+$.

Example 113: (S)-(2,3-dichlorophenyl)(3-methyl-8-(pyridin-2-yl)-5,6-dihydro-[1,2,4]triazolo[4,3-a]pyrazin-7(8H)-yl)methanone

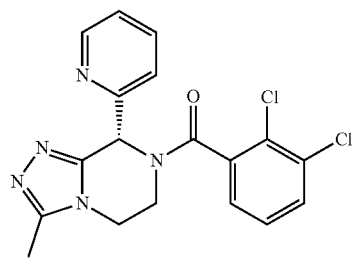 [SMILES: Cc1nnc2n1CCN(C(=O)c1cccc(Cl)c1Cl)[C@H]2c1ccccn1]

The desired product was prepared in an analogous manner to example 85 (using 2,3-dichlorobenzoyl chloride instead of 2-chloro-3-(trifluoromethyl)benzoyl chloride.) The racemic product was separated via chiral SFC (Stationary phase: CHIRALPAK AD-H 5 μm 250×20 mm), (Mobile phase: 75% $CO_2$, 25% iPrOH) yielding the desired product. $^1$H NMR (400 MHz, $CDCl_3$) δ 8.61-8.42 (m, 1H), 7.94-7.08 (m, 6H), 6.11-5.90; 5.22-5.07 (m, 1H), 4.46-3.57 (m, 4H), 2.54-2.41 (m, 3H). MS (ESI) mass calcd. $C_{18}H_{15}Cl_2N_5O$, 387.1; m/z found, 387.7 $[M+H]^+$.

Example 114: (R)-(2-chloro-3-(trifluoromethyl)phenyl)(8-(4-fluorophenyl)-3-methyl-5,6-dihydro-[1,2,4]triazolo[4,3-a]pyrazin-7(8H)-yl)methanone

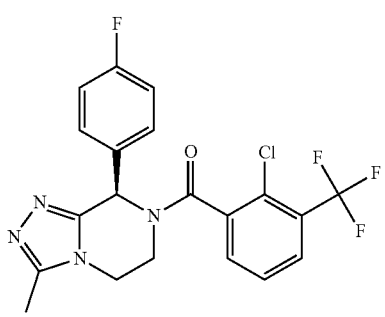

The desired product was prepared in an analogous manner to example 101. The racemic product was separated via chiral SFC (Stationary phase: CHIRALPAK AD-H 5 μm 250×20 mm), (Mobile phase: 80% $CO_2$, 20% iPrOH) yielding the desired product. $^1$H NMR (400 MHz, $CDCl_3$) δ 7.85-7.75 (m, 1H), 7.57-7.27 (m, 4H), 7.11-6.99 (m, 2H), 6.13-5.93; 5.20-5.07 (m, 1H), 4.15-3.27 (m, 4H), 2.52-2.43 (m, 3H). MS (ESI) mass calcd. $C_{20}H_{15}ClF_4N_4O$, 438.1; m/z found, 438.7 $[M+H]^+$.

Example 115: (S)-(2-chloro-3-(trifluoromethyl)phenyl)(8-(4-fluorophenyl)-3-methyl-5,6-dihydro-[1,2,4]triazolo[4,3-a]pyrazin-7(8H)-yl)methanone

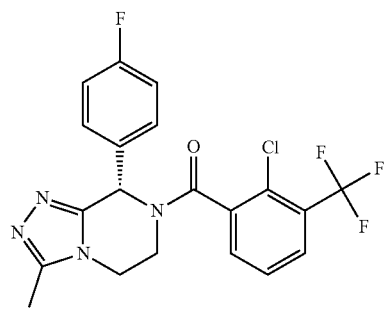

The desired product was prepared in an analogous manner to example 101. The racemic product was separated via chiral SFC (Stationary phase: CHIRALPAK AD-H 5 μm 250×20 mm), (Mobile phase: 80% $CO_2$, 20% iPrOH) yielding the desired product. $^1$H NMR (400 MHz, $CDCl_3$) δ 7.86-7.76 (m, 1H), 7.57-7.27 (m, 4H), 7.11-6.99 (m, 2H), 6.12-5.94; 5.20-5.04 (m, 1H), 4.15-3.26 (m, 4H), 2.53-2.41 (m, 3H). MS (ESI) mass calcd. $C_{20}H_{15}ClF_4N_4O$, 438.1; m/z found, 438.7 $[M+H]^+$.

Example 116: (R)-(8-(4-fluorophenyl)-3-methyl-5,6-dihydro-[1,2,4]triazolo[4,3-a]pyrazin-7(8H)-yl)(2-methyl-3-(trifluoromethyl)phenyl)methanone

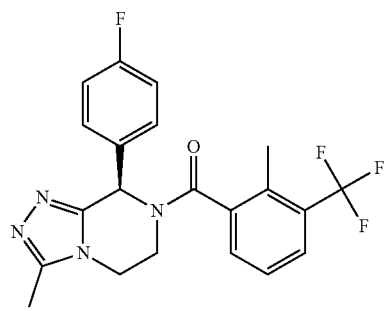 [SMILES: Cc1c(C(=O)N2CCn3c(C)nnc3[C@H]2c2ccc(F)cc2)cccc1C(F)(F)F]

The desired product was prepared in an analogous manner to example 101 (using 2-methyl-3-(trifluoromethyl)benzoyl chloride instead of 82-chloro-3-(trifluoromethyl)benzoyl chloride.) The racemic product was separated via chiral SFC (Stationary phase: CHIRALPAK AD-H 5 μm 250×20 mm), (Mobile phase: 75% $CO_2$, 25% iPrOH) yielding the desired product. $^1$H NMR (400 MHz, $CDCl_3$) δ 7.76-7.66 (m, 1H), 7.47-7.27 (m, 4H), 7.11-6.96 (m, 2H), 6.21-5.93; 5.21-5.12 (m, 1H), 4.13-3.28 (m, 4H), 2.53-2.18 (m, 6H). MS (ESI) mass calcd. $C_{21}H_{18}F_4N_4O$, 418.1; m/z found, 418.8 $[M+H]^+$.

Example 117: (S)-(8-(4-fluorophenyl)-3-methyl-5,6-dihydro-[1,2,4]triazolo[4,3-a]pyrazin-7(8H)-yl)(2-methyl-3-(trifluoromethyl)phenyl)methanone

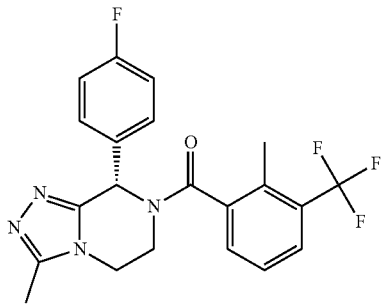 [SMILES: Cc1c(C(=O)N2CCn3c(C)nnc3[C@@H]2c2ccc(F)cc2)cccc1C(F)(F)F]

The desired product was prepared in an analogous manner to example 101 (using 2-methyl-3-(trifluoromethyl)benzoyl chloride instead of 82-chloro-3-(trifluoromethyl)benzoyl chloride.) The racemic product was separated via chiral SFC (Stationary phase: CHIRALPAK AD-H 5 μm 250×20 mm), (Mobile phase: 75% $CO_2$, 25% iPrOH) yielding the desired product. $^1$H NMR (400 MHz, $CDCl_3$) δ 7.77-7.65 (m, 1H), 7.47-7.27 (m, 4H), 7.13-6.98 (m, 2H), 6.21-5.92; 5.20-5.14 (m, 1H), 4.15-3.29 (m, 4H), 2.55-2.16 (m, 6H). MS (ESI) mass calcd. $C_{21}H_{18}F_4N_4O$, 418.1; m/z found, 418.8 $[M+H]^+$.

Example 118: (R)-(2-chloro-4-fluorophenyl)(8-phenyl-3-(trifluoromethyl)-5,6-dihydro-[1,2,4]triazolo[4,3-a]pyrazin-7(8H)-yl)methanone

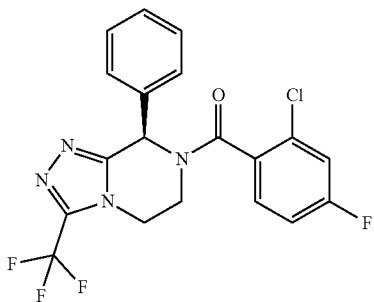 [SMILES: O=C(c1ccc(F)cc1Cl)N1CCn2c(nnc2C(F)(F)F)[C@H]1c1ccccc1]

The desired product was prepared in an analogous manner to example 108 (using trifluoracetic anhydride instead of difluoroacetic anhydride in Step C and 2-chloro-4-fluorobenzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, $CDCl_3$) δ 7.54-7.48 (m, 1H), 7.46-7.02 (m, 7H), 6.17-6.09; 5.18-5.10 (m, 1H), 4.38-3.29 (m, 4H). MS (ESI) mass calcd. $C_{19}H_{13}ClF_4N_4O$, 424.1; m/z found, 424.7 $[M+H]^+$.

Example 119: (S)-(2-chloro-4-fluorophenyl)(8-phenyl-3-(trifluoromethyl)-5,6-dihydro-[1,2,4]triazolo[4,3-a]pyrazin-7(8H)-yl)methanone

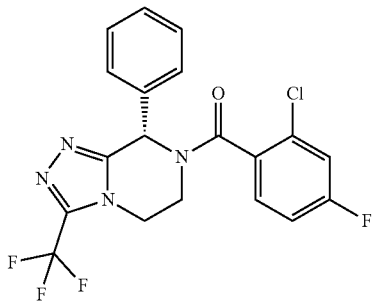 [SMILES: O=C(c1ccc(F)cc1Cl)N1CCn2c(nnc2C(F)(F)F)[C@@H]1c1ccccc1]

The desired product was separated from example 118 via chiral SFC (Stationary phase: CHIRALPAK AD-H 5 μm 250×20 mm), (Mobile phase: 70% $CO_2$, 30% iPrOH) yielding the desired product. $^1$H NMR (500 MHz, $CDCl_3$) δ 7.55-7.46 (m, 1H), 7.45-7.01 (m, 7H), 6.17-6.09; 5.18-5.10 (m, 1H), 4.36-3.33 (m, 4H). MS (ESI) mass calcd. $C_{19}H_{13}ClF_4N_4O$, 424.1; m/z found, 424.7 $[M+H]^+$.

Example 120: (R)-(2,4-dichlorophenyl)(8-phenyl-3-(trifluoromethyl)-5,6-dihydro-[1,2,4]triazolo[4,3-a]pyrazin-7(8H)-yl)methanone

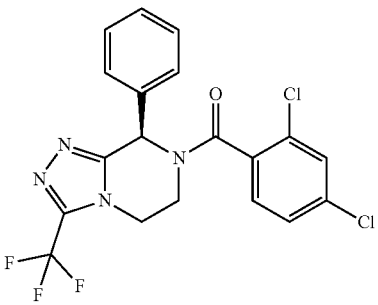 [SMILES: O=C(c1ccc(Cl)cc1Cl)N1CCn2c(nnc2C(F)(F)F)[C@H]1c1ccccc1]

The desired product was prepared in an analogous manner to example 108 (using trifluoracetic anhydride instead of difluoroacetic anhydride in Step C and 2,4-dichlorobenzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 70% $CO_2$, 30% iPrOH) yielding the desired product. $^1$H NMR (500 MHz, $CDCl_3$) δ 7.53-7.47 (m, 1H), 7.47-7.30 (m, 7H), 6.15-6.09; 5.17-5.09 (m, 1H), 4.37-3.30 (m, 4H). MS (ESI) mass calcd. $C_{19}H_{13}Cl_2F_3N_4O$, 440.0; m/z found, 440.7 $[M+H]^+$.

Example 121: (S)-(2,4-dichlorophenyl)(8-phenyl-3-(trifluoromethyl)-5,6-dihydro-[1,2,4]triazolo[4,3-a]pyrazin-7(8H)-yl)methanone

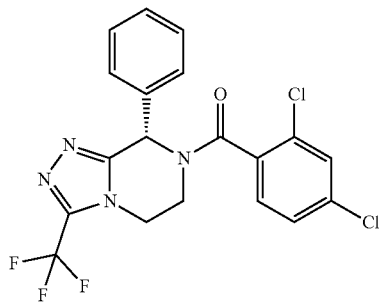 [SMILES: O=C(c1ccc(Cl)cc1Cl)N1CCn2c(nnc2C(F)(F)F)[C@@H]1c1ccccc1]

The desired product was separated from example 120 via chiral SFC (Stationary phase: CHIRALPAK AD-H 5 μm 250×20 mm), (Mobile phase: 70% $CO_2$, 30% iPrOH) yielding the desired product. $^1$H NMR (400 MHz, $CDCl_3$) δ 7.54-7.47 (m, 1H), 7.47-7.29 (m, 7H), 6.15-6.09; 5.17-5.08 (m, 1H), 4.37-3.31 (m, 4H). MS (ESI) mass calcd. $C_{19}H_{13}Cl_2F_3N_4O$, 440.0; m/z found, 440.7 [M+H]$^+$.

Example 122: (R)-(2-methyl-3-(trifluoromethyl)phenyl)(8-phenyl-3-(trifluoromethyl)-5,6-dihydro-[1,2,4]triazolo[4,3-a]pyrazin-7(8H)-yl)methanone

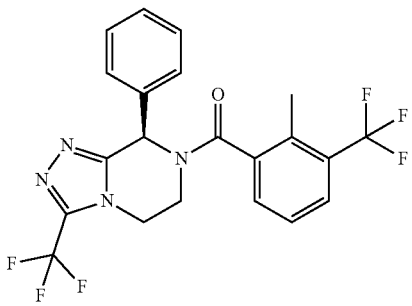 [SMILES: Cc1c(C(=O)N2CCn3c(nnc3C(F)(F)F)[C@H]2c2ccccc2)cccc1C(F)(F)F]

The desired product was prepared in an analogous manner to example 108 (using trifluoracetic anhydride instead of difluoroacetic anhydride in Step C and 2-methyl-3-(trifluoromethyl)benzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 80% $CO_2$, 20% iPrOH) yielding the desired product. $^1$H NMR (500 MHz, $CDCl_3$) δ 7.77-7.68 (m, 1H), 7.60-7.27 (m, 7H), 6.31-6.06; 5.25-5.15 (m, 1H), 4.43-3.40 (m, 4H), 2.51-2.18 (m, 3H). MS (ESI) mass calcd. $C_{21}H_{16}F_6N_4O$, 454.1; m/z found, 454.8 [M+H]$^+$.

Example 123: (S)-(2-methyl-3-(trifluoromethyl)phenyl)(8-phenyl-3-(trifluoromethyl)-5,6-dihydro-[1,2,4]triazolo[4,3-a]pyrazin-7(8H)-yl)methanone

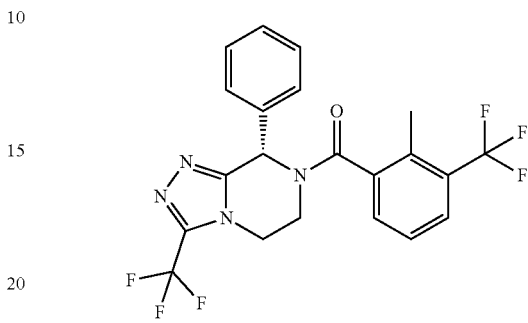

The desired product was separated from example 122 via chiral SFC (Stationary phase: CHIRALPAK AD-H 5 μm 250×20 mm), (Mobile phase: 80% $CO_2$, 20% iPrOH) yielding the desired product. $^1$H NMR (400 MHz, $CDCl_3$) δ 7.78-7.67 (m, 1H), 7.60-7.28 (m, 7H), 6.33-6.06; 5.26-5.14 (m, 1H), 4.43-3.37 (m, 4H), 2.51-2.16 (m, 3H). MS (ESI) mass calcd. $C_{21}H_{16}F_6N_4O$, 454.1; m/z found, 454.8 [M+H]$^+$.

Example 124: (R)-(2,3-dichloro-4-fluorophenyl)(8-phenyl-3-(trifluoromethyl)-5,6-dihydro-[1,2,4]triazolo[4,3-a]pyrazin-7(8H)-yl)methanone

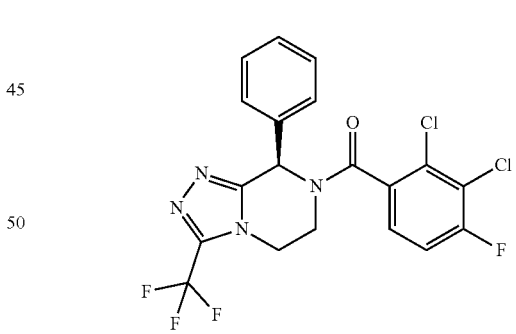

The desired product was prepared in an analogous manner to example 108 (using trifluoracetic anhydride instead of difluoroacetic anhydride in Step C and 2,3-dichloro-4-fluorobenzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 75% $CO_2$, 25% iPrOH) yielding the desired product. $^1$H NMR (500 MHz, $CDCl_3$) δ 7.51-7.47 (m, 1H), 7.43-7.13 (m, 6H), 6.33-6.06; 5.17-5.09 (m, 1H), 4.37-3.34 (m, 4H). MS (ESI) mass calcd. $C_{19}H_{12}Cl_2F_4N_4O$, 458.0; m/z found, 458.7 [M+H]$^+$.

Example 125: (S)-(2,3-dichloro-4-fluorophenyl)(8-phenyl-3-(trifluoromethyl)-5,6-dihydro-[1,2,4]triazolo[4,3-a]pyrazin-7(8H)-yl)methanone

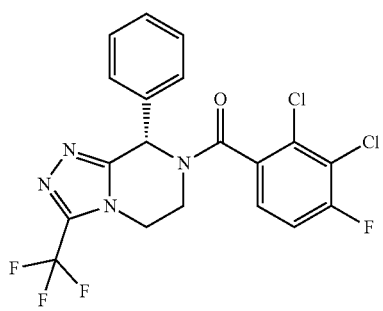 [SMILES: O=C(c1ccc(F)c(Cl)c1Cl)N1CCn2c(nnc2C(F)(F)F)[C@@H]1c1ccccc1]

The desired product was separated from example 124 via chiral SFC (Stationary phase: CHIRALPAK AD-H 5 μm 250×20 mm), (Mobile phase: 75% CO$_2$, 25% iPrOH) yielding the desired product. $^1$H NMR (400 MHz, CDCl$_3$) δ 7.52-7.46 (m, 1H), 7.44-7.11 (m, 6H), 6.33-6.08; 5.17-5.09 (m, 1H), 4.39-3.32 (m, 4H). MS (ESI) mass calcd. C$_{19}$H$_{12}$Cl$_2$F$_4$N$_4$O, 458.0; m/z found, 458.7 [M+H]$^+$.

Example 126 (±)-(8-(1H-pyrazol-5-yl)-3-(trifluoromethyl)-5,6-dihydro-[1,2,4]triazolo[4,3-a]pyrazin-7(8H)-yl)(2-chloro-3-(trifluoromethyl)phenyl)methanone

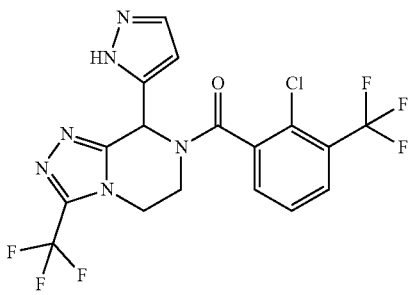 [SMILES: O=C(c1cccc(C(F)(F)F)c1Cl)N1CCn2c(nnc2C(F)(F)F)C1c1ccn[nH]1]

The desired product was prepared in an analogous manner to example 108 (using 1-(2-tetrahydropyranyl)-1H-pyrazole-5-boronic acid pinacol ester instead of phenylboronic acid in Step A and trifluoracetic anhydride instead of difluoroacetic anhydride in Step C) and was purified via basic HPLC (Agilent prep system, Waters XBridge C18 5 μm 50×100 mm column, 5-95% MeCN/20 nM NH$_4$OH over 22 min at 80 mL/min) yielding the desired product. $^1$H NMR (500 MHz, CDCl$_3$) δ 7.87-7.74 (m, 1H), 7.61-7.41 (m, 3H), 12.01-10.82 (m, 1H), 7.41-7.37; 6.50-6.14 (m, 2H), 6.13-6.03; 5.16-5.04 (m, 1H), 4.48-3.50 (m, 4H). MS (ESI) mass calcd. C$_{17}$H$_{11}$ClF$_6$N$_6$O, 464.1; m/z found, 465.1 [M+H]$^+$.

Example 127: (±)-(2-chloro-3-(trifluoromethyl)phenyl)(8-(pyridin-3-yl)-3-(trifluoromethyl)-5,6-dihydro-[1,2,4]triazolo[4,3-a]pyrazin-7(8H)-yl)methanone

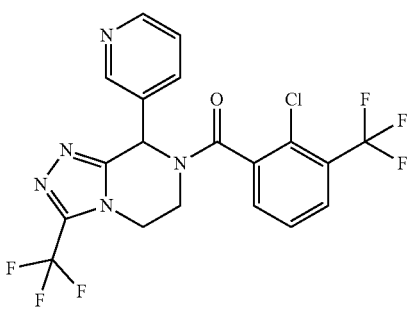

The desired product was prepared in an analogous manner to example 108 (using 1-(2-tetrahydropyranyl)-1H-pyrazole-5-boronic acid pinacol ester instead of phenylboronic acid in Step A and trifluoracetic anhydride instead of difluoroacetic anhydride in Step C) and was purified via basic HPLC (Agilent prep system, Waters XBridge C18 5 μm 50×100 mm column, 5-95% MeCN/20 nM NH$_4$OH over 22 min at 80 mL/min) yielding the desired product. $^1$H NMR (500 MHz, CDCl$_3$) δ 8.68-8.54 (m, 2H), 7.92-7.29 (m, 4H), 6.20-6.11; 5.28-5.14 (m, 1H), 4.43-3.30 (m, 4H). MS (ESI) mass calcd. C$_{19}$H$_{12}$ClF$_6$N$_5$O, 475.1; m/z found, 476.1 [M+H]$^+$.

Example 128: (R)-(2-fluoro-3-(trifluoromethyl)phenyl)(8-phenyl-3-(trifluoromethyl)-5,6-dihydro-[1,2,4]triazolo[4,3-a]pyrazin-7(8H)-yl)methanone

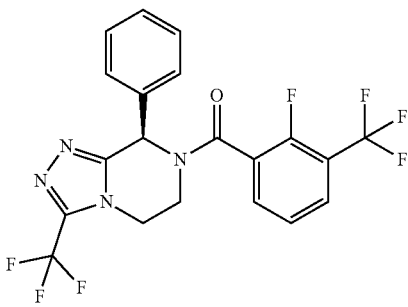

The desired product was prepared in an analogous manner to example 108 (using trifluoracetic anhydride instead of difluoroacetic anhydride in Step C and 2-fluoro-3-(trifluoromethyl)benzoyl chloride instead of 2-chloro-3-(trifluoromethyl)benzoyl chloride in Step E) and was separated via chiral SFC (Stationary phase: CHIRALPAK AD-H 5 μm 250×20 mm), (Mobile phase: 85% CO$_2$, 15% iPrOH) yielding the desired product. $^1$H NMR (400 MHz, CDCl$_3$) δ 7.83-7.67 (m, 1H), 7.60-7.29 (m, 7H), 6.29-6.21; 5.19-5.09 (m, 1H), 4.38-3.38 (m, 4H). MS (ESI) mass calcd. C$_{20}$H$_{13}$F$_7$N$_4$O, 458.1; m/z found, 458.7 [M+H]$^+$.

Example 129: (S)-(2-fluoro-3-(trifluoromethyl)phenyl)(8-phenyl-3-(trifluoromethyl)-5,6-dihydro-[1,2,4]triazolo[4,3-a]pyrazin-7(8H)-yl)methanone

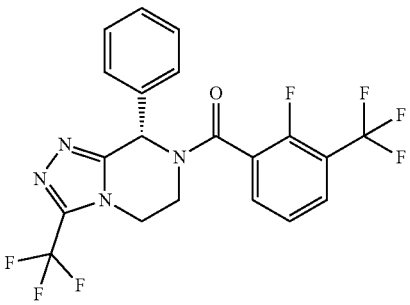 [SMILES: O=C(c1cccc(C(F)(F)F)c1F)N1CCn2c(nnc2C(F)(F)F)[C@@H]1c1ccccc1]

The desired product was separated from example 128 via chiral SFC (Stationary phase: CHIRALPAK AD-H 5 μm 250×20 mm), (Mobile phase: 85% CO$_2$, 15% iPrOH) yielding the desired product. $^1$H NMR (400 MHz, CDCl$_3$) δ 7.82-7.67 (m, 1H), 7.62-7.28 (m, 7H), 6.30-6.21; 5.19-5.09 (m, 1H), 4.39-3.35 (m, 4H). MS (ESI) mass calcd. C$_{20}$H$_{13}$F$_7$N$_4$O, 458.1; m/z found, 458.7 [M+H]$^+$.

Example 130: (±)-(2-chloro-3-(trifluoromethyl)phenyl)(6-methyl-8-phenyl-3-(trifluoromethyl)-5,6-dihydro-[1,2,4]triazolo[4,3-a]pyrazin-7(8H)-yl)methanone

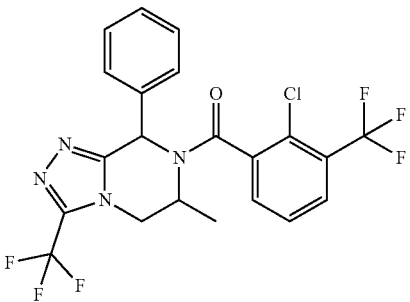 [SMILES: CC1Cn2c(nnc2C(F)(F)F)C(c2ccccc2)N1C(=O)c1cccc(C(F)(F)F)c1Cl]

Intermediate 130A: 6-methyl-8-phenyl-3-(trifluoromethyl)-5,6,7,8-tetrahydro-[1,2,4]triazolo[4,3-a]pyrazine

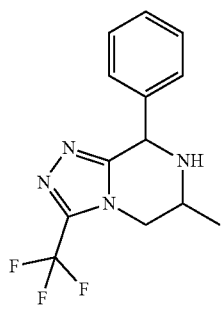 [SMILES: CC1Cn2c(nnc2C(F)(F)F)C(c2ccccc2)N1]

Step A: 6-methyl-8-phenyl-3-(trifluoromethyl)-5,6,7,8-tetrahydro-[1,2,4]triazolo[4,3-a]pyrazine. The desired product was prepared in an analogous manner to example 108 (using 2,3-dichloro-5-methylpyrazine instead of 2,3-dichloropyrazine in Step A and trifluoracetic anhydride instead of difluoroacetic anhydride in Step C) yielding the desired product (502 mg, 46%). MS (ESI) mass calcd. C$_{13}$H$_{13}$F$_3$N$_4$, 282.2; m/z found, 283.2 [M+H]$^+$.

Example 130: (±)-(2-chloro-3-(trifluoromethyl)phenyl)(6-methyl-8-phenyl-3-(trifluoromethyl)-5,6-dihydro-[1,2,4]triazolo[4,3-a]pyrazin-7(8H)-yl)methanone

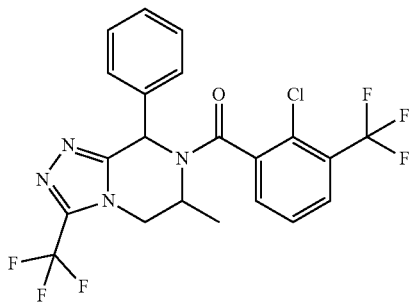

Step 130B: (±)-(2-chloro-3-(trifluoromethyl)phenyl)(6-methyl-8-phenyl-3-(trifluoromethyl)-5,6-dihydro-[1,2,4]triazolo[4,3-a]pyrazin-7(8H)-yl)methanone. In a flask purged with N$_2$ was added 6-methyl-8-phenyl-3-(trifluoromethyl)-5,6,7,8-tetrahydro-[1,2,4]triazolo[4,3-a]pyrazine (54 mg, 0.191 mmol) followed by 1 mL of THF. The resulting solution was cooled to −78° C. and n-butylLithium (2.0M in cyclohexane) (115 uL, 0.23 mmol) was added. The solution was left to stir at −78° C. for 15 minutes then a 1 mL solution of 2-chloro-3-(trifluoromethyl)benzoyl chloride (70 mg, 0.287 mmol) in THF was added drop-wise. Upon complete addition, the reaction mixture was left to stir at −78° C. for 30 minutes then quenched with addition of 3 mL of water. The resulting reaction mixture was extracted three times with DCM and the combined organic layers were dried with MgSO$_4$ then concentrated under reduced pressure. The resulting residue was purified via basic HPLC (Agilent prep system, Waters XBridge C18 5 um 50×100 mm column, 5-95% MeCN/20 nM NH$_4$OH over 22 min at 80 mL/min) yielding the desired product. $^1$H NMR (500 MHz, CDCl$_3$) δ 7.74-7.21 (m, 8H), 5.65-5.25; (m, 1H), 4.23-3.12 (m, 3H), 1.41-1.34 (m, 3H). MS (ESI) mass calcd. C$_{21}$H$_{15}$ClF$_6$N$_4$O, 488.1; m/z found, [M+H]$^+$.

Example 131 (±)-Benzyl-3-(trifluoromethyl)-5,6-dihydro-[1,2,4]triazolo[4,3-a]pyrazin-7(8H)-yl)(2-chloro-3-(trifluoromethyl)phenyl)methanone

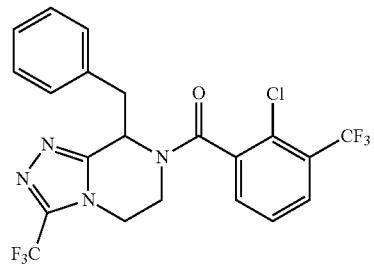 [SMILES: O=C(c1cccc(C(F)(F)F)c1Cl)N1CCn2c(nnc2C(F)(F)F)C1Cc1ccccc1]

Intermediate 131A: 3-(trifluoromethyl)-5,6-dihydro-[1,2,4]triazolo[4,3-a]pyrazine 7-oxide

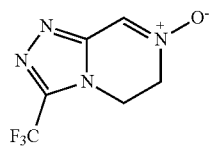

Step A: 3-(trifluoromethyl)-5,6-dihydro-[1,2,4]triazolo[4,3-a]pyrazine 7-oxide. To a stirring mixture of 3-(trifluoromethyl)-5,6,7,8-tetrahydro-[1,2,4]triazolo[4,3-a]pyrazine (5.00 g, 26.0 mmol) and sodium tungstate dihydrate (0.343 g, 1.04 mmol) in water (5 mL) at 0° C. was added 30% hydrogen peroxide soln (6.1 mL) dropwise over 15 min. The reaction was warmed to rt, kept at rt for 5 min, then cooled again over an ice bath. After 20 min sodium bisulfite (1 g) was added portionwise followed by $CH_2Cl_2$ (300 mL), MeOH (30 mL) and NaCl to saturate the mixture. After stirring for 16 h the solids were allowed to settle and the liquids were decanted away. The solids were washed with 10% MeOH/$CH_2Cl_2$. The organics were combined, dried with $Na_2SO_4$, filtered and concentrated in vacuo. The residue was purified by flash chromatography ($SiO_2$, 0-10% (10% 2N $NH_3$/MeOH)/DCM) to obtain the product as a yellow oil (5.36 g, 26%). $^1$H NMR (500 MHz, $CH_3OD$) δ 8.16-8.13 (m, 1H), 4.71-4.64 (m, 2H), 4.52-4.44 (m, 2H). MS (ESI) mass calcd. $C_6H_5F_3N_4O$, 206.04; m/z found, 206.9 [M+H]$^+$.

Intermediate 131B: 8-benzyl-3-(trifluoromethyl)-5,6-dihydro-[1,2,4]triazolo[4,3-a]pyrazin-7(8H)-ol

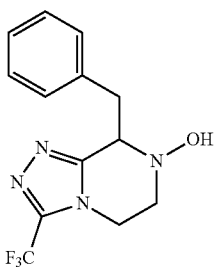 [SMILES: ON1CCn2c(nnc2C(F)(F)F)C1Cc1ccccc1]

Step B: 8-benzyl-3-(trifluoromethyl)-5,6-dihydro-[1,2,4]triazolo[4,3-a]pyrazin-7(8H)-ol. To a solution of 3-(trifluoromethyl)-5,6-dihydro-[1,2,4]triazolo[4,3-a]pyrazine 7-oxide (626 mg, 3.04 mmol) in THF (5 mL) at 0° C. was added benzylmagnesium chloride in THF (3.8 mL, 7.6 mmol). After stirring for 30 min at 0° C. saturated ammonium chloride was added. The layers were separated and the water layer was extracted two times more with methylene chloride. The organic layers were combined, dried over anhydrous $Na_2SO_4$, filtered and concentrated. The residue was purified by flash chromatography ($SiO_2$, 0-10% (10% 2N $NH_3$/MeOH)/DCM) to obtain the product as a yellow oil (750 mg, 83%). MS (ESI) mass calcd. $C_{13}H_{13}F_3N_4O$, 298.10; m/z found, 299.7 [M+H]$^+$.

Intermediate 131C: 8-benzyl-3-(trifluoromethyl)-5,6,7,8-tetrahydro-[1,2,4]triazolo[4,3-a]pyrazine

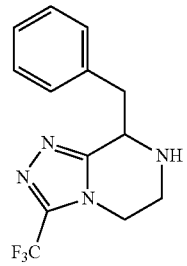

Step C: 8-benzyl-3-(trifluoromethyl)-5,6,7,8-tetrahydro-[1,2,4]triazolo[4,3-a]pyrazine. To a solution of (8-benzyl-3-(trifluoromethyl)-5,6-dihydro-[1,2,4]triazolo[4,3-a]pyrazin-7(8H)-ol (750 mg, 2.52 mmol) in acetic acid (5 mL) and water (5 mL) was added zinc dust (839 mg, 12.6 mmol). The reaction was stirred at 60° C. for 30 min followed by the addition of more zinc (800 mg). The reaction was allowed to stir at 40° C. for 72 h after which time it was filtered over celite. The filtrate was evaporated in vacuo followed by the addition of $CH_2Cl_2$ and aq $NaHCO_3$ (sat). The layers were separated and the water layer was extracted two times more with methylene chloride. The organic layers were combined, dried over anhydrous $Na_2SO_4$, filtered and concentrated. The residue was purified by flash chromatography ($SiO_2$, 0-10% (10% 2N $NH_3$/MeOH)/DCM) to obtain the title compound (413 mg, 58%). $^1$H NMR (400 MHz, $CD_3OD$) δ 7.36-7.19 (m, 5H), 4.39 (dd, J=9.5, 3.8 Hz, 1H), 4.22-4.13 (m, 1H), 4.10-4.00 (m, 1H), 3.61-3.53 (dd, J=14.0, 3.7 Hz, 1H), 3.12-2.97 (m, 2H). MS (ESI) mass calcd. $C_{13}H_{13}F_3N_4$, 282.11; m/z found, 283.6 [M+H]$^+$.

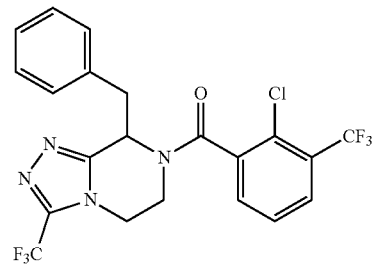

Step D: (8-benzyl-3-(trifluoromethyl)-5,6-dihydro-[1,2,4]triazolo[4,3-a]pyrazin-7(8H)-yl)(2-chloro-3-(trifluoromethyl)phenyl)methanone. To a solution of 8-benzyl-3-(trifluoromethyl)-5,6,7,8-tetrahydro-[1,2,4]triazolo[4,3-a]pyrazine (93 mg, 0.32 mmol) in $CH_2Cl_2$ (1 mL) was added triethylamine (0.1 mL, 0.7 mmol) and 2-chloro-3-(trifluoromethyl)benzoyl chloride. The reaction was allowed to stir at rt for 30 min and then evaporated in vacuo. The residue was dissolved MeOH and purified by prep HPLC to afford the title compound as a white solid (95 mg, 59%). MS (ESI): mass calcd. for $C_{21}H_{15}ClF_6N_4O$, 488.08; m/z found, 489.1 [M+H]$^+$.

Example 132: (S)-(2,3-dichlorophenyl)(3-(4-hydroxypyridin-2-yl)-6-methyl-5,6-dihydro-[1,2,4]triazolo[4,3-a]pyrazin-7(8H)-yl)methanone (precursor for the radiolabeling of (5)-(2,3-dichlorophenyl)(3-(4-[$^{11}$C]methoxypyridin-2-yl)-6-methyl-5,6-dihydro-[1,2,4]triazolo[4,3-a]pyrazin-7(8H)-yl)methanon

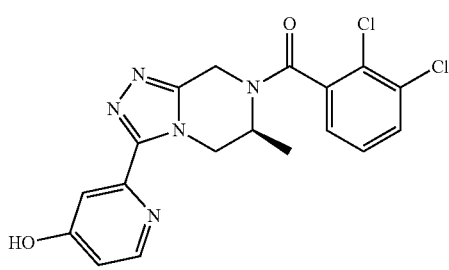 [SMILES: C[C@H]1Cn2c(nnc2-c2cc(O)ccn2)CN1C(=O)c1cccc(Cl)c1Cl]

Iodotrimethylsilane (71.45 µL, 0.502 mmol) was added to a solution of (S)-(2,3-dichlorophenyl)(3-(4-methoxypyridin-2-yl)-6-methyl-5,6-dihydro-[1,2,4]triazolo[4,3-a]pyrazin-7(8H)-yl)methanone (70 mg, 0.167 mmol) in CH$_3$CN (1 mL). The mixture was stirred at 150° C. for 6 min under microwave irradiation. MeOH (0.1 mL) was added and the solvents were evaporated in vacuo. The crude was purified by column chromatography (silica, MeOH in EtOAc 0:100 to 10:90), the desired fractions were collected and the solvent evaporated in vacuo. The residue was diluted into a mixture of water and CH$_2$Cl$_2$. The organic layer was separated, dried (Na$_2$SO$_4$), filtered and the solvent was evaporated in vacuo. Finally, the compound was triturated with diisopropyl ether to afford (S)-(2,3-dichlorophenyl)(3-(4-hydroxypyridin-2-yl)-6-methyl-5,6-dihydro-[1,2,4]triazolo[4,3-a]pyrazin-7(8H)-yl)methanone (41.4 mg, 61.2%).

Radiosynthesis, Biodistribution and Radiometabolite Analysis

HPLC analysis was performed on a LaChrom Elite HPLC system (Hitachi, Armstadt, Germany) connected to a UV spectrometer set at 220 nm. For the analysis of radiolabeled compounds, the HPLC eluate, after passage through the UV detector, was led over a shielded 3-inch NaI(Tl) scintillation detector connected to a multichannel analyser (Gabi box, Raytest, Straubenhardt, Germany). The output signal was recorded and analysed using a GINA Star data acquisition system (Raytest, Straubenhardt, Germany). Radioactivity in samples of biodistribution studies, cell uptake experiments and radiometabolite analysis was quantified using an automated gamma counter equipped with a 3-inch NaI(Tl) well crystal coupled to a multichannel analyser (Wallac 2480 Wizard, Wallac, Turku, Finland). Results were corrected for background radiation, physical decay and counter dead time.

Animals were housed in individually ventilated cages in a thermoregulated (~22° C.), humidity-controlled facility under a 12 h/12 h light/dark cycle with access to food and water ad libitum. All animal experiments were conducted according to the Belgian code of practice for the care and use of animals, after approval from the KU Leuven University Ethics Committee for Animals.

Radiosynthesis of (S)-(2,3-dichlorophenyl)(3-(4-[$^{11}$C]methoxypyridin-2-yl)-6-methyl-5,6-dihydro-[1,2,4]triazolo[4,3-a]pyrazin-7(8H)-yl)methanone (Example [$^{11}$C]55)

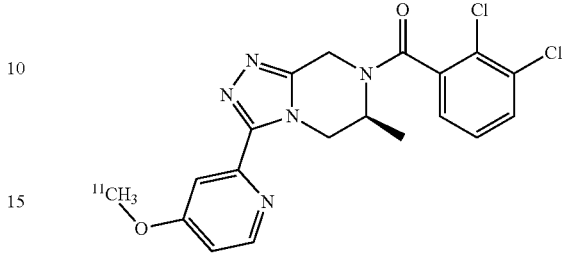

Carbon-11 was produced via a [$^{14}$N(p,α)$^{11}$C] nuclear reaction. The target gas, which was a mixture of N$_2$ (95%) and H$_2$ (5%), was irradiated using 18-MeV protons at a beam current of 25 µA. The irradiation was done for about 30 min to yield [$^{11}$C]methane ([$^{11}$C]CH$_4$). The [$^{11}$C]CH$_4$ was then transferred to a home-built recirculation synthesis module and trapped on a Porapak column that was immersed in liquid nitrogen. After flushing with helium, the condensed [$^{11}$C]CH$_4$ was converted to the gaseous phase by bringing the Porapak loop to room temperature. This [$^{11}$C]CH$_4$ was then reacted with vaporous I$_2$ at 650° C. to convert it to [$^{11}$C]methyl iodide ([$^{11}$C]MeI). Subsequently, the [$^{11}$C]MeI was passed over a silver triflate column (6 mm×50 mm) at 180° C. The resulting [$^{11}$C]methyl-triflate ([$^{11}$C]MeOTf) was bubbled with a flow of helium through a solution of the precursor (S)-(2,3-dichlorophenyl)(3-(4-hydroxypyridin-2-yl)-6-methyl-5,6-dihydro-[1,2,4]triazolo[4,3-a]pyrazin-7(8H)-yl)methanone (0.2 mg) and Cs$_2$CO$_3$ (1-3 mg) in anhydrous DMF (0.2 mL). When the amount of radioactivity in the reaction vial had stabilized, the reaction mixture was left at room temperature for 3 min. The crude mixture was diluted with water (0.6 mL) and injected onto an HPLC system (XBridge C18, 5 µm, 4.6 mm×150 mm; Waters) eluted with a mixture of 0.05 M NaOAc (pH 5.5) and EtOH (60:40 v/v) at a flow rate of 1 mL/min. UV detection of the HPLC eluate was performed at 254 nm. The radiolabeled product was collected after 11 min. The collected peak corresponding to the desired radioligand, (Example [$^{11}$C] 55), was then diluted with saline (Mini Plasco®, Braun, Melsungen, Germany) to obtain a final EtOH concentration of 10% and the solution was sterile filtered through 0.22 µm membrane filter (Millex®-GV, Millipore).

Chemical and radiochemical purity of Example [$^{11}$C]55) formulation was analyzed on an analytical HPLC system consisting of an XBridge C$_{18}$ column (3.5 µm, 3.0 mm×100 mm, Waters) eluted with a mixture of 0.05 M NaOAc (pH 5.5) and CH$_3$CN (70:30 v/v) at a flow rate of 0.8 mL/min. UV detection was performed at 220 nm. The crude radiolabeling mixture was purified using semi-preparative RP-HPLC affording (S)-(2,3-dichlorophenyl)(3-(4-[11C]methoxypyridin-2-yl)-6-methyl-5,6-dihydro-[1,2,4]triazolo[4,3-a]pyrazin-7(8H)-yl)methanone in good radiochemical yields (40-60%, relative to starting radioactivity of [$^{11}$C] MeOTf, non-decay corrected, n=12), with a radiochemical purity of >98% and an average specific radioactivity of 233±99 GBq/µmol at end of synthesis (EOS) (n=12). The identity of the radiotracer was confirmed by co-elution with the non-radioactive analogue after co-injection onto an analytical HPLC system Radiosynthesis of (S)-(2,3-dichlorophenyl)(3-(4-[$^{18}$F]fluoropyridin-2-yl)-6-methyl-5,6-dihydro-[1,2,4]triazolo[4,3-a]pyrazin-7(8H)-yl)methanone (Example [$^{18}$F]68)

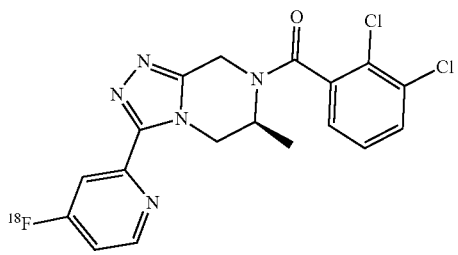 [SMILES: C[C@H]1Cn2c(nnc2-c2cc([18F])ccn2)CN1C(=O)c1cccc(Cl)c1Cl]

Fluorine-18 was produced via a [$^{18}$O (p,n)$^{18}$F] nuclear reaction in a Cyclone 18/9 cyclotron (Ion Beam Applications, Louvain-la-Neuve, Belgium). After irradiation, [$^{18}$F]F$^-$ was trapped on a SepPak Light Accell plus QMA anion exchange cartridge (Waters) and eluted with a kryptofix 222 14 mg/K$_2$CO$_3$ 1.2 mg dissolved in 750 µl CH$_3$CN/H$_2$O mixture (95:5 v/v) into the reaction vial. The solvent was evaporated under a stream of helium at 80° C. by applying microwave heating (Resonance instruments 521, Skokie Illinois USA) with a power of 50 W and further dried by azeotropic distillation of traces of water using CH$_3$CN (1 mL in four fractions) at the above applied microwave settings. Finally, the residue was dried under a stream of helium at 50 W until complete dryness.

A solution of the precursor (S)-(2,3-dichlorophenyl)(3-(4-chloropyridin-2-yl)-6-methyl-5,6-dihydro-[1,2,4]triazolo[4,3-a]pyrazin-7(8H)-yl)methanone (1.5 mg), which was prepared in an analogous manner to Example 68, in DMSO (0.5 mL) was added to the dried [$^{18}$F]F$^-$/K$_2$CO$_3$/kryptofix residue and the mixture was heated using microwave irradiation at 50 W and (temperature setting 170° C.) for 3 min. Next, the crude mixture was diluted with a mixture of EtOH/NaOAc 0.025M pH 5.5 (17/83 v/v; 0.5 mL) and injected onto the HPLC system. The HPLC system consisted of an XBridge column (C18, 5 µm, 4.6 mm×150 mm; Waters) that was eluted with a mixture of EtOH/NaOAc 0.025M pH 5.5 (35/65 v/v) at a flow rate of 1 mL/min. UV detection of the HPLC eluate was performed at 254 nm. The radiolabeled product (S)-(2,3-dichlorophenyl)(3-(4-[$^{18}$F]fluoropyridin-2-yl)-6-methyl-5,6-dihydro-[1,2,4]triazolo[4,3-a]pyrazin-7(8H)-yl)methanone, (Example [$^{18}$F]68), was collected after a total synthesis time of 45 min with an average radiochemical yield of 15% and a specific activity of 22 GBq/µmol.

Radiochemical purity and identity was assayed using an HPLC system consisting of an XBridge column (C18, 3µ, 3.0×100 mm; Waters) eluted with NaOAc 0.05M pH 5.5/CH$_3$CN (70:30) at a flow rate of 0.8 ml/min. The radioligand had a retention time of 7.7 min and had a radiochemical purity>98%.

Biodistribution Studies

The biodistribution studies were performed in healthy female Wistar rats (body weight, 185-220 g) at 2, 30 and 60 min after tracer injection (n=3/time point). Rats were anesthetized with isoflurane (2.5% in oxygen at a flow rate of 1 L/min) and injected with the radioligand via a tail vein. The animals were sacrificed by decapitation at the indicated time points. Blood and major organs were collected in tared tubes and weighed. The radioactivity in the dissected organs and blood was counted using an automated gamma counter. For calculation of total blood radioactivity, blood mass was assumed to be 7% of the body mass.

Biodistribution Study of [$^{11}$C]55

Table 2 presents the percentage injected dose (% ID) in the different organs and body fluids at 2, 30 and 60 min after radiotracer injection. 10.0% of the injected dose was detected in the blood at 2 min after injection, which cleared to 5.3% at 60 min after tracer injection. The total initial brain uptake of [$^{11}$C]55 was 0.6% at 2 min after injection and this cleared to 0.4% at 60 min after tracer injection. At 60 min after tracer injection, 43.8% of the injected dose was retained in the liver and the intestines. Urinary excretion of the radiotracer was minimal, with 2.9% ID in urine and kidneys at 60 min after injection.

Table 3 shows the standardized uptake values (SUV) for different brain regions and blood. At 2 min after tracer injection, the radioactivity concentration in the cerebellum was highest of all brain regions. Clear wash-out was observed between 2 and 30 min after tracer injection for all brain regions with relative wash-out ratios higher than 1.3 (2 min-to-30 min). The radioactivity concentration at 30 and 60 min after tracer injection was comparable for all studied brain regions, and also for total brain and the blood at the three studied time points.

TABLE 2

Biodistribution of [$^{11}$C]55 in normal rats at 2, 30 and 60 minutes after tracer injection.

| | % ID$^a$ | | |
|---|---|---|---|
| | 2 min | 30 min | 60 min |
| urine | 0.1 ± 0.1 | 0.9 ± 0.0 | 1.1 ± 0.5 |
| kidneys | 4.5 ± 0.8 | 1.9 ± 0.1 | 1.8 ± 0.2 |
| liver | 34.8 ± 2.1 | 19.4 ± 0.5 | 17.1 ± 0.3 |
| spleen + pancreas | 1.4 ± 0.4 | 0.6 ± 0.1 | 0.6 ± 0.1 |
| lungs | 2.1 ± 0.3 | 1.0 ± 0.1 | 1.1 ± 0.4 |
| heart | 1.3 ± 0.2 | 0.4 ± 0.0 | 0.4 ± 0.1 |
| intestines | 14.0 ± 1.8 | 23.8 ± 1.1 | 26.7 ± 9.1 |
| stomach | 1.7 ± 0.3 | 2.1 ± 1.0 | 5.1 ± 3.4 |
| cerebrum | 0.5 ± 0.0 | 0.3 ± 0.0 | 0.3 ± 0.1 |
| cerebellum | 0.1 ± 0.0 | 0.1 ± 0.0 | 0.1 ± 0.0 |
| blood | 10.0 ± 2.4 | 5.2 ± 0.6 | 5.3 ± 0.6 |
| carcass | 35.1 ± 4.1 | 46.9 ± 0.5 | 43.2 ± 5.3 |

$^a$Percentage of injected dose calculated as counts per minute (cpm) in organ/total cpm recovered. Data are expressed as mean ± SD; n = 3 per time point.

TABLE 3

[$^{11}$C]55 concentration in the different rat brain regions and blood at 2, 30 and 60 minutes after tracer injection.

| | SUV$^a$ | | |
|---|---|---|---|
| | 2 min | 30 min | 60 min |
| striatum | 0.78 ± 0.0 | 0.45 ± 0.0 | 0.50 ± 0.1 |
| hippocampus | 0.74 ± 0.0 | 0.43 ± 0.0 | 0.52 ± 0.1 |
| cortex | 0.80 ± 0.2 | 0.58 ± 0.1 | 0.65 ± 0.1 |
| rest of cerebrum | 0.86 ± 0.0 | 0.46 ± 0.0 | 0.53 ± 0.1 |
| whole cerebrum | 0.83 ± 0.0 | 0.46 ± 0.0 | 0.54 ± 0.1 |
| cerebellum | 1.02 ± 0.1 | 0.53 ± 0.0 | 0.59 ± 0.1 |
| blood | 1.42 ± 0.3 | 0.74 ± 0.1 | 0.75 ± 0.1 |

$^a$Calculated as (radioactivity in cpm in organ/weight of organ in grams)/(total cpm recovered/body weight rat in grams). Data are expressed as mean ± SD; n = 3 per time point.

Rat Plasma Radiometabolite Analysis of [$^{11}$C]55

Radiometabolites of [$^{11}$C]55 in plasma of normal female Wistar rats (n=2) were quantified at 30 min after tracer injection. The Chromolith C18 column was eluted with gradient mixtures of 0.05 M NaOAc (pH 5.5) (A) and $CH_3CN$ (B) (0-4 min: isocratic 0% B and flow rate of 0.5 mL/min; 4-14 min: linear gradient 0% B to 90% B and flow rate of 1 mL/min; and 14-17 min: isocratic 90% B and flow rate of 1 mL/min). UV detection was done at 220 nm. The reconstructed radiochromatogram demonstrated two peaks, corresponding to intact [$^{11}$C]55 eluting at 10 min and a polar radiometabolite eluting at 2 min (chromatograms not shown). 30 min after radiotracer injection, 70±6% of the recovered radioactivity in the plasma was in the form of intact tracer and 30±6% was in the form of polar radiometabolite(s). The fraction of more lipophilic radiometabolites eluting after the intact tracer was negligible (<1.5%).

Perfused Rat Brain Radiometabolite Analysis of [$^{11}$C]55

Radiometabolites of [$^{11}$C]55 in perfused cerebrum and cerebellum of normal female Wistar rats (n=2) were quantified at 30 min after tracer injection. Homogenates were analysed using an analytical XBridge column ($C_{18}$, 5 μm, 3×100 mm; Waters) eluted with a mixture of 0.05 M sodium acetate (pH 5.5) and $CH_3CN$ (65:35 v/v) at a flow rate of 0.8 mL/min. UV detection was performed at 220 nm. The reconstructed radiochromatograms from perfused rat cerebellum and cerebrum HPLC analysis at 30 min post tracer injection showed only one radioactive peak corresponding to intact [$^{11}$C]55 eluting at 9 min (chromatograms not shown). Both the fraction of more polar and more lipophilic radiometabolites were negligible (<2%).

The studies using [$^{18}$F]68, were performed in a manner analogus manner to those performed with [$^{11}$C]55 and the results of those experiments are shown in Tables 4 and 5.

Biodistribution Study of [$^{18}$F]68

TABLE 4

Biodistribution of [$^{18}$F] 68 in normal rats at 2, 30 and 60 minutes after tracer injection.
% ID[a]

|  | 2 min | 30 min | 60 min |
| --- | --- | --- | --- |
| urine | 0.1 ± 0.0 | 8.4 ± 1.8 | 8.4 ± 1.8 |
| kidneys | 3.3 ± 0.5 | 1.1 ± 0.2 | 0.9 ± 0.1 |
| liver | 34.6 ± 2.4 | 7.5 ± 0.6 | 3.61 ± 0.3 |
| spleen + pancreas | 1.3 ± 0.2 | 0.3 ± 0.1 | 0.2 ± 0.0 |
| lungs | 1.6 ± 0.1 | 0.7 ± 0.1 | 0.6 ± 0.2 |
| heart | 0.9 ± 0.1 | 0.2 ± 0.0 | 0.1 ± 0.0 |
| intestines | 10.6 ± 2.1 | 20.9 ± 6.0 | 11.2 ± 0.6 |
| stomach | 1.5 ± 0.5 | 1.6 ± 0.9 | 10.7 ± 3.3 |
| cerebrum | 0.6 ± 0.0 | 0.1 ± 0.0 | 0.1 ± 0.0 |
| cerebellum | 0.1 ± 0.0 | 0.0 ± 0.0 | 0.0 ± 0.0 |
| blood | 6.8 ± 0.6 | 4.3 ± 0.3 | 2.0 ± 0.5 |
| carcass | 40.8 ± 0.8 | 56.6 ± 2.8 | 60.4 ± 2.3 |
| bone[b] | 8.8 ± 0.8 | 44.5 ± 3.8 | 64.5 ± 5.9 |

[a]Percentage of injected dose calculated as counts per minute (cpm) in organ/total cpm recovered. Data are expressed as mean ± SD; n = 3 per time point.
[b]calculated to estimated total bone tissue (% ID/g bone * body mass* 0.12)

TABLE 5

[$^{18}$F]68 concentration in the different rat brain regions and blood at 2, 30 and 60 minutes after tracer injection.
SUV[a]

|  | 2 min | 30 min | 60 min |
| --- | --- | --- | --- |
| striatum | 1.19 ± 0.13 | 0.24 ± 0.05 | 0.19 ± 0.03 |
| hippocampus | 1.11 ± 0.10 | 0.23 ± 0.04 | 0.19 ± 0.03 |

TABLE 5-continued

[$^{18}$F]68 concentration in the different rat brain regions and blood at 2, 30 and 60 minutes after tracer injection.
SUV[a]

|  | 2 min | 30 min | 60 min |
| --- | --- | --- | --- |
| cortex | 1.27 ± 0.13 | 0.94 ± 0.29 | 0.69 ± 0.17 |
| rest of cerebrum | 1.20 ± 0.11 | 0.31 ± 0.06 | 0.25 ± 0.04 |
| whole cerebrum | 1.20 ± 0.11 | 0.31 ± 0.06 | 0.25 ± 0.04 |
| cerebellum | 1.21 ± 0.22 | 0.33 ± 0.07 | 0.38 ± 0.08 |
| blood | 0.97 ± 0.08 | 0.61 ± 0.04 | 0.29 ± 0.07 |

[a]Calculated as (radioactivity in cpm in organ/weight of organ in grams)/(total cpm recovered/body weight rat in grams). Data are expressed as mean ± SD; n = 3 per time point.

Pharmacological Examples

The in vitro affinity of the compounds of the invention for the rat and human P2X7 receptor was determined using a human peripheral blood mononuclear cells (PBMCs), a human whole blood assay, a $Ca^{2+}$ flux and radioligand binding assay in recombinant human P2X7 cells and recombinant rat P2X7 cells. In Table 6, when the data cell has been left blank, it is intended to mean that the compound was not tested in that assay. The data represented in Tables 2 may represent a value from a single determination or when the experiment was run more than once, the data represent averages from between 2-12 runs.

P2X7 Antagonism in Human Peripheral Blood Mononuclear Cells (PBMCs) and Human Whole Blood.

Human blood was collected using a blood donor program. PBMCs were isolated from blood using a Ficoll density gradient technique. Briefly, blood was laid on Ficoll solution and centrifuged at RT for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Human Whole Blood experiments, 150 μl of human blood was platted on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5' triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbent assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Tables 2, this data is represented by PBMC 1 μM (% control) and PBMC 10 μM (% control) and human whole blood $IC_{50}$ (μM). Data are analyzed and graphed on Graphpad Prism 5. For analysis, each concentration point is averaged from triplicate values and the averaged values are plotted on Graphpad Prism. The $IC_{50}$ for each compound is then uploaded into 3DX.

P2X7 Antagonism in Recombinant Human P2X7 Cells or Recombinant Rat P2X7 Cells: (a) $Ca^{2+}$ Flux and (b) Radioligand Binding (a) $Ca^{2+}$ flux: $1321N_1$ cells expressing the recombinant human or rat P2X7 channel was cultured in HyQ DME/ (HyClone/Dulbecco's Modified Eagle Medium) high glucose supplemented with 10% Fetal Bovine Serum (FBS) and appropriate selection marker. Cells were seeded at a density of 25000 cells/well (96-well clear bottom black walled plates) in 100 μl volume/well. On the day of the experiment, cell plates were washed with assay buffer, containing (in mM): 130 NaCl, 2 KCl, 1 CaCl$_2$), 1 MgCl$_2$, 10 HEPES, 5 glucose; pH 7.40 and 300 mOs. After the wash, cells were loaded with the Calcium-4 dye (Molecular Device) and incubated in the dark for 60 minutes. Test compounds were prepared at 250× the test concentration in neat DMSO. Intermediate 96-well compound plates were prepared by transferring 1.2 μL of the compound into 300 μL of assay buffer. A further 3× dilution occurred when transferring 50 μL/well of the compound plate to 100 μL/well in the cell plate. Cells were incubated with test compounds and dye for 30 minutes. Calcium dye fluorescence was monitored in FLIPR as the cells were challenged by adding 50 μL/well of BzATP (final concentration is 250 μM BzATP (human and rat)). The fluorescence change was measured 180 seconds after adding the agonist. Peak fluorescence was plotted as a function of BzATP concentration using Origin 7 software and the resultant IC$_{50}$ is shown in Tables 2 under the column headings FLIPR (human) IC$_{50}$ (μM) and FLIPR (rat) IC$_{50}$ (μM).

(b) Radioligand binding: human or rat P2X7-1321N1 cells were collected and frozen @ −80° C. On the day of the experiment, cell membrane preparations were made according to standard published methods. The total assay volume was 100 μl: 10 μl compound (10×)+(b) 40 μl tracer (2.5×)+50 μl membrane (2×). The tracer used for the assay was tritiated A-804598. The compound can be prepared as described in the literature. (Donnelly-Roberts, D. Neuropharmacology 2008, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The IC$_{50}$ generated in the binding assay was corrected for tracer concentration and affinity of the tracer to derive at the affinity (K) of the test compounds. The data are presented in Table 6 under the headings: P2X7 human K (μM) and P2X7 rat K (μM). Data are analyzed and graphed on Graphpad Prism 5. For analysis, each concentration point is averaged from triplicate values and the averaged values are plotted on Graphpad Prism.

TABLE 6*

P2X7 activity of the compounds of Formula (I) in a panel of in-vitro assays

| Ex # | PBMC 1 μM (% control) | PBMC 10 μM (% control) | P2X7 human K$_i$ (μM) | P2X7 rat K$_i$ (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 1 | −11.8 | nt | 0.0550 | nt | 0.0065 | 1.2070 | nt |
| 2 | 15.0 | 7.1 | 0.0214 | 0.0093 | 0.0013 | 0.8153 | 0.009 |
| 3 | 100.4 | nt | nt | 1.7783 | >10 | >10 | nt |
| 4 | 98.2 | nt | nt | nt | nt | nt | nt |
| 5 | 88.7 | nt | nt | nt | nt | nt | nt |
| 6 | 100.4 | nt | nt | 0.5012 | 1.2589 | 15.8489 | nt |
| 7 | 99.9 | nt | nt | 0.3162 | 1.9953 | 10.0000 | nt |
| 8 | 13.9 | nt | 0.0427 | nt | 0.0286 | 0.1600 | nt |
| 9 | 16.1 | nt | 0.0437 | nt | 0.0179 | 1.0233 | nt |
| 10 | 6.5 | nt | 0.0955 | nt | 0.0152 | 0.0198 | nt |
| 11 | 1.4 | nt | 0.0468 | nt | 0.0070 | 1.3772 | nt |
| 12 | nt | 15.0 | 0.0158 | 0.0045 | 0.0035 | 0.1023 | nt |
| 13 | nt | 14.9 | 1.5849 | 0.3162 | 0.2972 | >10 | nt |
| 14 | nt | 8.9 | 0.0316 | 0.0050 | 0.0109 | 0.0240 | nt |
| 15 | nt | 49.4 | 3.1623 | 0.5012 | 8.5114 | >10 | nt |
| 16 | nt | 14.4 | 0.1000 | nt | 0.0195 | 0.0177 | nt |
| 17 | nt | 3.0 | 0.0794 | nt | 0.0060 | 0.0650 | nt |
| 18 | nt | 102.4 | nt | nt | 1.4656 | 2.2387 | nt |
| 19 | nt | 7.1 | 0.0251 | 0.0079 | 0.0064 | 0.0062 | 0.182 |
| 20 | nt | 10.6 | 0.0398 | nt | 0.0105 | 0.0512 | nt |
| 21 | nt | 7.0 | 0.0282 | nt | 0.0102 | 0.0091 | 0.035 |
| 22 | nt | 2.9 | 0.0200 | nt | 0.0100 | 0.0050 | 0.016 |
| 23 | nt | 6.2 | 0.0631 | nt | 0.0146 | 0.0092 | 0.006 |
| 24 | nt | 8.9 | 0.0219 | nt | 0.0068 | 0.0047 | 0.025 |
| 25 | nt | 4.7 | 0.0372 | nt | 0.0100 | 7.8886 | nt |
| 26 | nt | 28.0 | nt | nt | 4.1305 | 3.9537 | nt |
| 27 | nt | 20.4 | nt | nt | 1.6634 | 2.9648 | nt |
| 28 | nt | 19.8 | nt | nt | 7.4817 | 3.7757 | nt |
| 29 | nt | −0.5 | nt | nt | 3.5481 | 2.9717 | nt |
| 30 | nt | −9.6 | 0.0501 | nt | 0.0838 | 0.9268 | 1.585 |
| 31 | nt | −11.8 | 0.0079 | nt | 0.0067 | 0.0753 | 0.016 |
| 33 | nt | 5.9 | 0.3162 | nt | 0.3681 | 2.3496 | nt |
| 34 | nt | 18.1 | nt | nt | 12.8529 | >10 | nt |
| 35 | nt | 19.9 | nt | nt | >10 | >10 | nt |
| 36 | nt | 8.1 | 0.1259 | nt | 0.0553 | 0.0111 | nt |
| 37 | nt | 4.8 | 0.2512 | nt | 0.1718 | 4.5920 | nt |
| 38 | nt | 25.6 | nt | 0.0562 | 9.9312 | 7.6736 | nt |
| 39 | nt | 22.0 | nt | nt | 2.4322 | 9.4406 | nt |
| 40 | nt | 39.8 | nt | nt | 9.0365 | 14.7571 | nt |
| 41 | nt | 33.5 | nt | nt | >10 | 10.6905 | nt |
| 42 | nt | 28.3 | nt | 0.0186 | 2.1257 | 9.2257 | nt |
| 43 | nt | 31.7 | nt | 0.1334 | 9.7051 | >10 | nt |
| 44 | nt | 8.4 | nt | nt | 3.9174 | 1.4588 | nt |
| 45 | nt | 11.7 | nt | nt | 1.8155 | 0.4083 | nt |
| 46 | nt | 4.4 | nt | nt | 2.5410 | 2.4210 | nt |

TABLE 6*-continued

P2X7 activity of the compounds of Formula (I) in a panel of in-vitro assays

| Ex # | PBMC 1 μM (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 47 | nt | 36.0 | nt | nt | 10.3753 | 1.6069 | nt |
| 48 | nt | 31.2 | nt | nt | 1.6634 | 0.6368 | nt |
| 49 | nt | 20.4 | nt | nt | 4.1115 | 2.7290 | nt |
| 50 | nt | 41.0 | nt | nt | 10.0000 | 1.6827 | nt |
| 51 | nt | 17.5 | nt | nt | 1.9320 | 0.5781 | nt |
| 52 | nt | 40.5 | nt | nt | 7.0469 | 2.0893 | nt |
| 53 | nt | 6.8 | 0.0158 | 0.0398 | 0.0020 | 0.0628 | 0.079 |
| 54 | nt | 0.8 | 0.0141 | 0.0100 | 0.0197 | 1.8239 | nt |
| 55 | nt | −1.3 | 0.0063 | 0.0010 | 0.0126 | 0.0200 | nt |
| 56 | nt | 102.0 | nt | nt | nt | nt | nt |
| 57 | nt | 83.5 | nt | nt | nt | nt | nt |
| 58 | nt | 93.9 | nt | nt | nt | nt | nt |
| 59 | nt | 69.8 | nt | nt | nt | nt | nt |
| 60 | nt | 54.0 | nt | nt | nt | nt | nt |
| 61 | nt | 29.3 | nt | nt | 0.3396 | >10 | nt |
| 62 | nt | 83.0 | nt | nt | nt | nt | nt |
| 63 | nt | 81.5 | nt | nt | nt | nt | nt |
| 64 | nt | 81.2 | nt | nt | nt | nt | nt |
| 65 | nt | 23.9 | nt | nt | >10 | >10 | nt |
| 66 | nt | −0.5 | 0.0079 | 0.0020 | 0.0027 | 0.0269 | nt |
| 67 | nt | −3.7 | 0.3162 | nt | 0.4831 | 2.0464 | nt |
| 68 | nt | 7.3 | 0.0063 | 0.0016 | 0.0052 | 0.0066 | nt |
| 69 | nt | 5.6 | 0.0032 | 0.0025 | 0.0031 | 0.3350 | nt |
| 70 | nt | 10.8 | 0.0126 | 0.0040 | 0.0069 | 0.0077 | nt |
| 71 | nt | 16.1 | nt | nt | 1.2218 | >10 | nt |
| 72 | nt | 25.9 | nt | 0.1778 | 8.5901 | >10 | nt |
| 73 | nt | 52.6 | nt | nt | 0.0068 | 0.1072 | nt |
| 74 | nt | 39.9 | nt | nt | 0.0049 | 0.0101 | nt |
| 75 | nt | 23.8 | 0.0288 | 0.0251 | 0.0529 | 0.5416 | nt |
| 76 | nt | 22.6 | 0.0100 | 0.0050 | 0.0067 | 0.0168 | nt |
| 77 | nt | 14.8 | nt | nt | 0.5888 | 1.1092 | nt |
| 78 | nt | 32.3 | nt | nt | 0.0143 | 6.6069 | nt |
| 79 | nt | −0.9 | 0.1000 | nt | 0.0151 | 0.0071 | nt |
| 80 | nt | 10.7 | 0.0200 | nt | 0.0563 | 0.3954 | nt |
| 81 | nt | 10.1 | 0.0501 | 0.0089 | 0.0113 | 0.0270 | nt |
| 82 | nt | 1.6 | nt | nt | 0.9594 | 1.8493 | nt |
| 83 | nt | 17.6 | nt | nt | 1.7906 | 0.9977 | nt |
| 84 | nt | 32.6 | 0.0200 | nt | 0.0025 | 0.0031 | nt |
| 85 | nt | 11.0 | 0.0398 | nt | 0.0301 | 1.0186 | nt |
| 86 | nt | 12.3 | 0.0126 | 0.0100 | 0.0023 | 0.0585 | nt |
| 87 | nt | 12.3 | nt | nt | 3.8107 | 9.9312 | nt |
| 88 |   | 7.4 | 0.0200 | 0.0251 | 0.0102 | 0.1662 |   |
| 89 | nt | 10.3 | nt | nt | 0.9795 | >10 | nt |
| 90 | nt | 2.3 | 0.0200 | nt | 0.0119 | 0.9638 | nt |
| 91 | nt | 1.9 | 0.0316 | nt | 0.0075 | 2.1316 | nt |
| 92 | nt | 37.1 | nt | nt | 0.7551 | 17.6604 | nt |
| 93 | nt | 7.9 | 0.0158 | 0.0063 | 0.0081 | 0.0178 | nt |
| 94 | nt | −3.8 | nt | nt | 0.4335 | 2.1577 | nt |
| 95 | nt | 8.9 | 0.0316 | nt | 0.0097 | 0.2113 | nt |
| 96 | nt | 43.6 | nt | nt | 4.8865 | >10 | nt |
| 97 | nt | −1.7 | 0.0126 | 0.0047 | 0.0078 | 0.0428 | nt |
| 98 | nt | 44.1 | nt | nt | 5.5081 | >10 | nt |
| 99 | nt | 4.9 | 0.0174 | 0.0063 | 0.0091 | 0.0348 | nt |
| 100 | nt | 102.0 | nt | nt | nt | nt | nt |
| 101 | nt | 12.3 | 0.0316 | nt | 0.0278 | 5.0583 | nt |
| 102 | nt | −20.1 | 0.0100 | 0.0295 | 0.0105 | 0.4883 | nt |
| 103 | nt | 15.0 | nt | nt | 1.3964 | >10 | nt |
| 104 | nt | 59.1 | nt | nt | 4.4771 | >10 | nt |
| 105 | nt | −16.6 | 0.0219 | nt | 0.0986 | 9.9541 | nt |
| 106 | nt | 26.7 | nt | nt | >10 | >10 | nt |
| 107 | nt | −25.8 | 0.0100 | nt | 0.0128 | 0.1782 | nt |
| 108 | nt | −4.2 | 0.0058 | 0.0100 | 0.0086 | 0.0816 | nt |
| 109 | nt | 42.7 | nt | nt | >10 | >10 | nt |
| 110 | nt | −2.2 | 0.0079 | 0.0166 | 0.0034 | 0.4406 | nt |
| 111 | nt | 67.2 | nt | nt | >10 | >10 | nt |
| 112 | nt | 6.8 | 0.0447 | nt | 0.1340 | 2.8249 | nt |
| 113 | nt | 54.0 | nt | nt | 3.8107 | >10 | nt |
| 114 | nt | 15.6 | nt | nt | 4.0832 | >10 | nt |
| 115 | nt | −9.9 | 0.0100 | nt | 0.0080 | 0.6227 | nt |
| 116 | nt | 59.5 | nt | nt | nt | nt | nt |
| 117 | nt | 2.5 | 0.0200 | nt | 0.0640 | 7.0307 | nt |
| 118 | nt | −22.9 | nt | nt | 0.9205 | 19.6336 | nt |

TABLE 6*-continued

P2X7 activity of the compounds of Formula (I) in a panel of in-vitro assays

| Ex # | PBMC 1 µM (% control) | PBMC 10 µM (% control) | P2X7 human $K_i$ (µM) | P2X7 rat $K_i$ (µM) | FLIPR (human) $IC_{50}$ (µM) | FLIPR (rat) $IC_{50}$ (µM) | Human whole blood $IC_{50}$ (µM) |
|---|---|---|---|---|---|---|---|
| 119 | nt | 87.3 | nt | nt | nt | nt | nt |
| 120 | nt | −16.0 | 0.0501 | nt | 0.4764 | >10 | nt |
| 121 | nt | 79.6 | nt | nt | nt | nt | nt |
| 122 | nt | −5.4 | 0.0100 | nt | 0.0098 | 0.2618 | nt |
| 123 | nt | 88.6 | nt | nt | nt | nt | nt |
| 124 | nt | −28.8 | 0.0079 | nt | 0.0106 | 0.2884 | nt |
| 125 | nt | −14.1 | nt | nt | 11.7219 | >10 | nt |
| 126 | nt | 2.1 | nt | nt | 1.5488 | >10 | nt |
| 127 | nt | 10.4 | 0.1259 | nt | 0.2553 | 28.2488 | nt |
| 128 | nt | 2.0 | 0.0501 | nt | 0.0685 | 0.2911 | nt |
| 129 | nt | 114.8 | nt | nt | nt | nt | nt |
| 130 | nt | 12.4 | nt | nt | >10 | >10 | nt |
| 131 | nt | nt | nt | nt | nt | nt | nt |

*means not tested

What is claimed:

1. A compound of Formula (I):

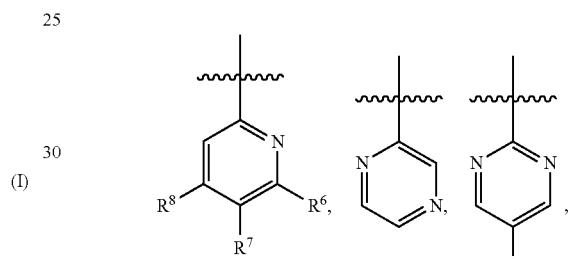

or an enantiomer or diastereomer thereof;
wherein:
$R^a$ is

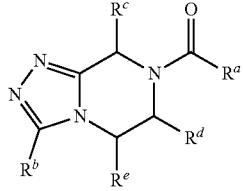

$R^1$ is halo or $C_1$-$C_3$alkyl;

$R^2$ is independently selected from the group consisting of: halo, and $C_1$-$C_3$perhaloalkyl;

$R^3$ is H;

$R^4$ is halo, $R^5$ is halo or $C_1$-$C_3$perhaloalkyl;

$R^b$ is independently selected from the group consisting of:

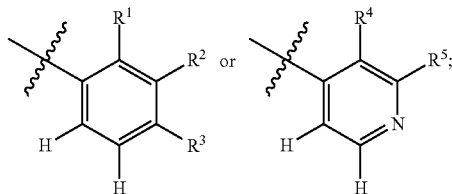

Wherein:

$R^6$ is H or halo;

$R^7$ is H or halo;

$R^{13}$ is independently selected from the group consisting of: H, halo and $OC_1$-$C_3$alkyl;

$R^8$ is independently selected from the group consisting of: H, halo, and $OC_1$-$C_3$alkyl;

$R^c$ is selected from the group consisting of:

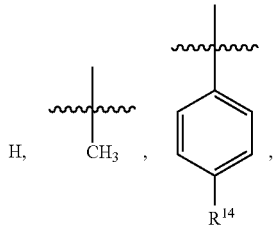

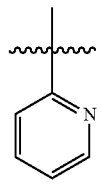, 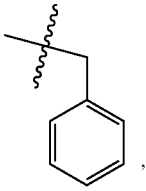,

-continued

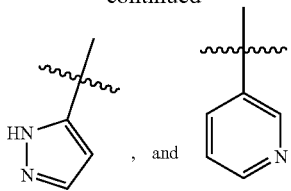, and $R^{14}$ is H or halo;
$R^d$ is H or $C_1$-$C_3$alkyl, and
$R^e$ is H, provided that two of $R^c$, $R^d$ and $R^e$ are H and one of $R^e$, $R^d$ and $R^e$ is not H,
  wherein the compound is a R enantiomer when $R^e$ is not H, and the compound is a S enantiomer when $R^d$ is not H,
or a pharmaceutically acceptable salt thereof.

2. The compound of claim 1, wherein $R^a$ is

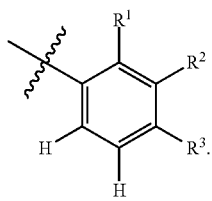

3. The compound of claim 1, wherein $R^a$ is

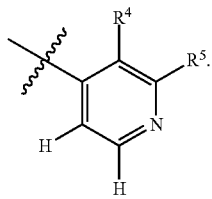

4. The compound of claim 1, wherein $R^a$ is

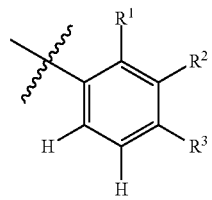

and $R^1$ is halo.

5. The compound of claim 1, wherein $R^a$ is

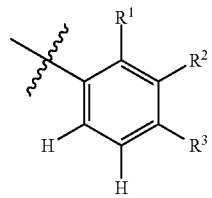

and $R^1$ is $C_1$-$C_3$alkyl.

6. The compound of claim 1, wherein $R^a$ is

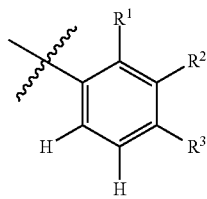

and $R^2$ is $C_1$-$C_3$perhaloalkyl.

7. The compound of claim 1, wherein $R^a$ is

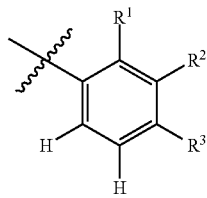

and $R^2$ is halo.

8. The compound of claim 1, wherein $R^a$ is

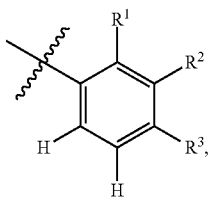

$R^1$ is halo and $R^2$ is $C_1$-$C_3$perhaloalkyl.

9. The compound of claim 1, wherein $R^a$ is

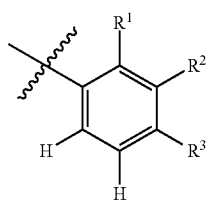

and $R^1$ and $R^2$ are halo.

10. The compound of claim 1, wherein $R^a$ is

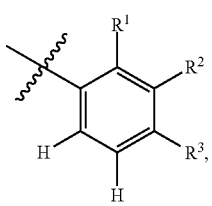

$R^1$ and $R^2$ are halo.

11. The compound of claim 1, wherein $R^a$ is

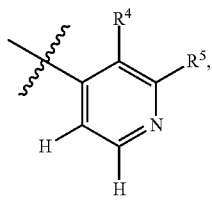

$R^4$ is halo and $R^5$ is $C_1$-$C_3$perhaloalkyl.

12. The compound of claim 1, wherein RD is independently selected from the group consisting of:

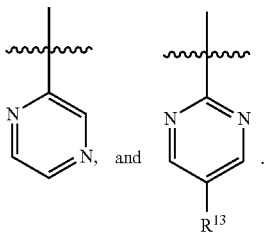

13. The compound of claim 1, wherein $R^b$ is

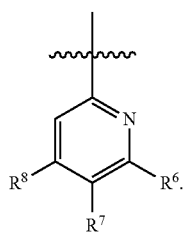

14. The compound of claim 1, wherein $R^b$ is

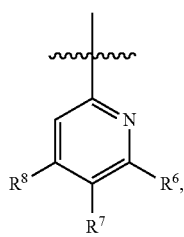

$R^6$ and $R^7$ are H and $R^8$ is $OCH_3$.

15. The compound of claim 1, wherein $R^b$ is

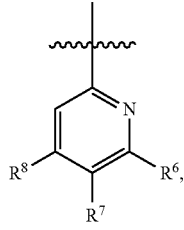

and $R^6$, $R^7$ and $R^8$ are H.

16. The compound of claim 1, wherein $R^b$ is

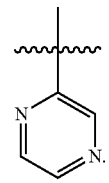 [SMILES: *c1cnccn1]

17. The compound of claim 1, wherein $R^b$ is

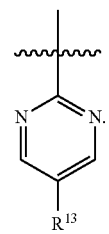

18. The compound of claim 1, wherein $R^d$ is $CH_3$.

19. The compound of claim 1, wherein $R^a$ is

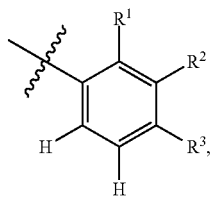

$R^1$ and $R^2$ are Cl, $R^c$ is $CH_3$, $R^b$ is

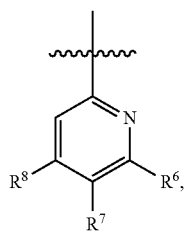

and $R^d$, $R^e$, $R^3$, $R^6$, $R^7$ and $R^8$ are H.

20. The compound of claim 1, wherein $R^a$ is

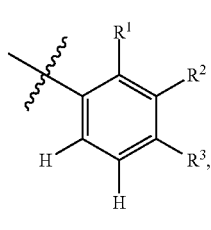

$R^1$ and $R^2$ are Cl, $R^d$ is $CH_3$, $R^b$ is

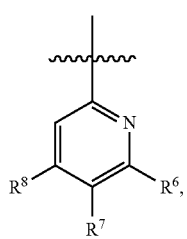

$R^8$ is $OCH_3$, and $R^c$, $R^e$, $R^3$, $R^6$, and $R^7$ are H.

21. A pharmaceutical composition, comprising:
(a) a compound of Formula (I):

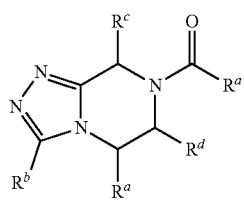
(I)

or an enantiomer or diastereomer thereof;
wherein:
$R^a$ is

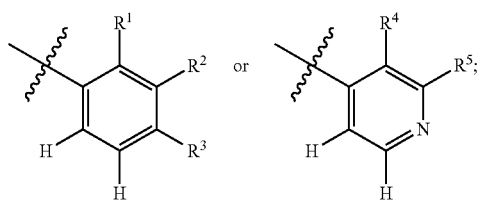

$R^1$ is halo or $C_1$-$C_3$alkyl;
$R^2$ is independently selected from the group consisting of: halo, and $C_1$-$C_3$perhaloalkyl;
$R^3$ is H;
$R^4$ is halo,
$R^5$ is halo or $C_1$-$C_3$perhaloalkyl;
$R^b$ is independently selected from the group consisting of:

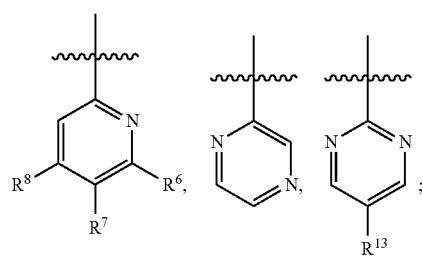

Wherein:
$R^6$ is H or halo;
$R^7$ is H or halo;
$R^{13}$ is independently selected from the group consisting of: H, halo and $OC_1$-$C_3$alkyl;
$R^8$ is independently selected from the group consisting of: H, halo, and $OC_1$-$C_3$alkyl;

$R^c$ is selected from the group consisting of:

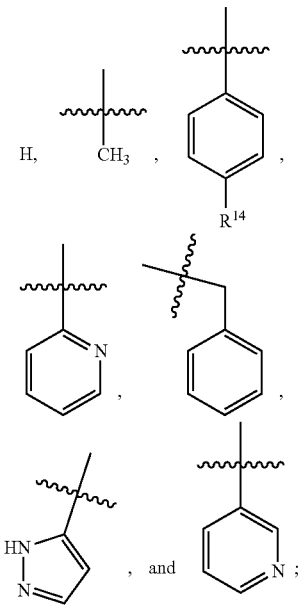

, and $R^{14}$ is H or halo;
$R^d$ is H or $C_1$-$C_3$alkyl, and
$R^e$ is H, provided that two of $R^c$, $R^d$ and $R^e$ are H and one of $R^c$, $R^d$ and $R^e$ is not H,
wherein the compound is a R enantiomer when $R^e$ is not H, and the compound is a S enantiomer when $R^d$ is not H,
or a pharmaceutically acceptable salt thereof; and
(b) at least one pharmaceutically acceptable excipient.

22. The compound of claim 1, wherein
$R^a$ is

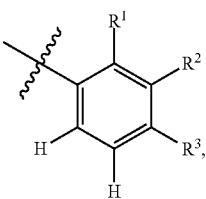

$R^1$ and $R^2$ are Cl,
$R^b$ is

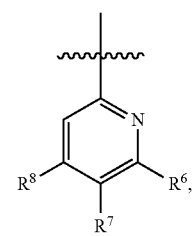

$R^e$ or $R^d$ is $CH_3$, $R^6$ and $R^7$ are H, and $R^8$ is H or $OCH_3$.

23. The compound of claim 1 selected from the group consisting of:

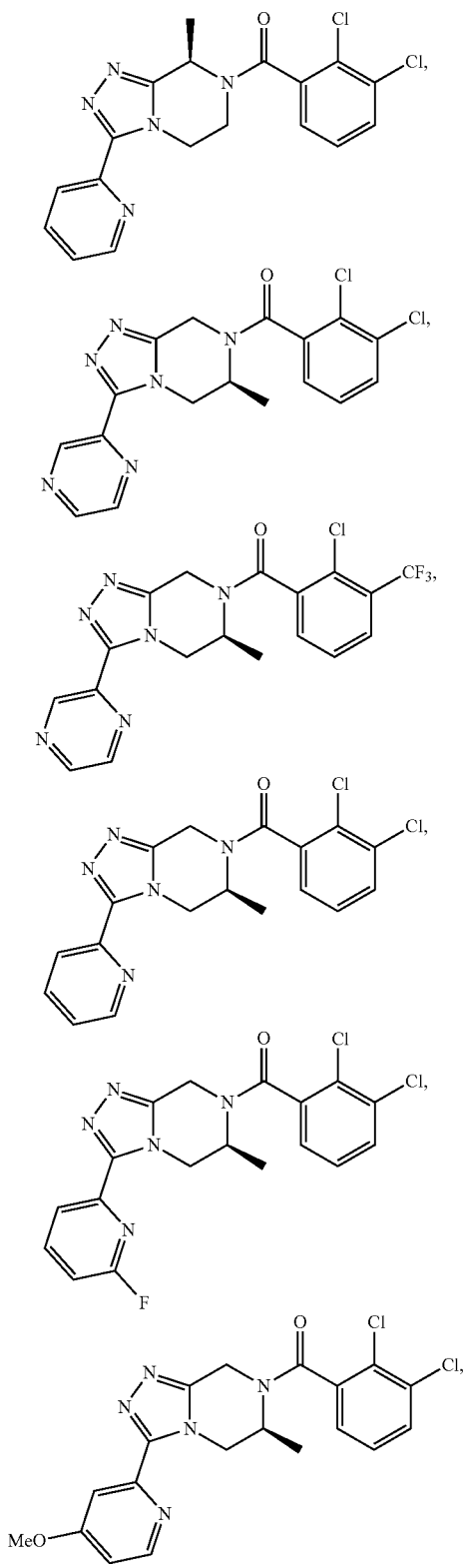
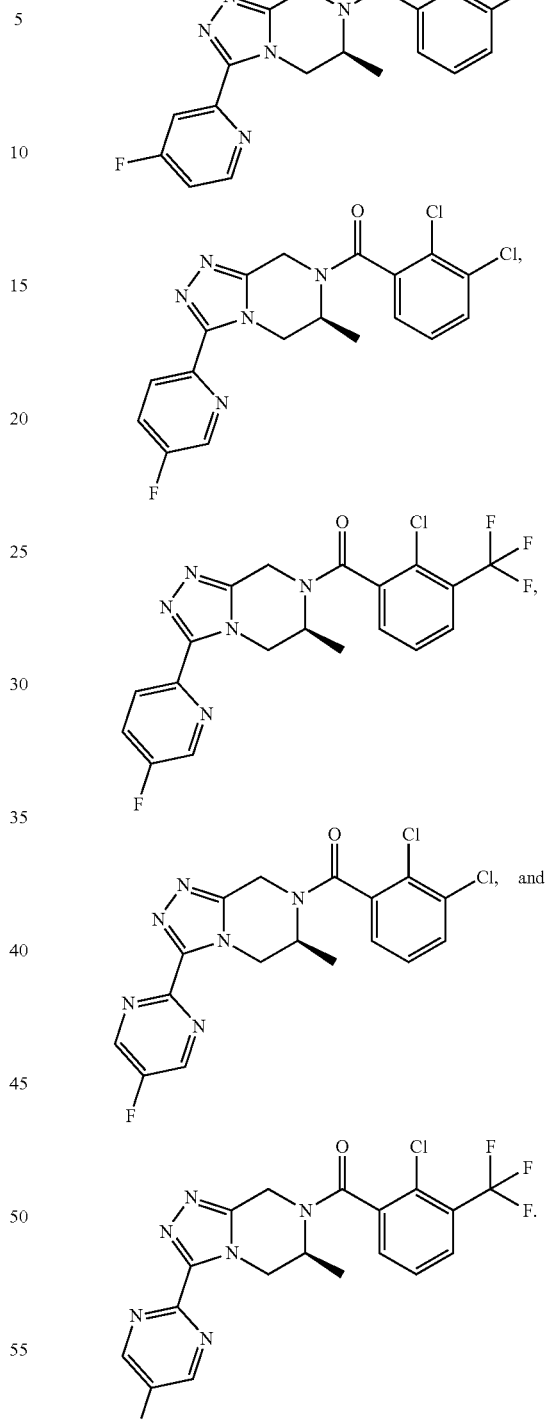
* * * * *